(12) United States Patent
Piferi et al.

(10) Patent No.: US 10,307,220 B2
(45) Date of Patent: *Jun. 4, 2019

(54) SURGICAL NAVIGATION DEVICES AND METHODS

(71) Applicant: MRI Interventions, Inc., Irvine, CA (US)

(72) Inventors: Peter Piferi, Orange, CA (US); Rajesh Pandey, Irvine, CA (US); Maxwell Jerad Daly, Redlands, CA (US); Kimble L. Jenkins, Memphis, TN (US)

(73) Assignee: MRI Interventions, Inc., Irvine, CA (US)

( * ) Notice: Subject to any disclaimer, the term of this patent is extended or adjusted under 35 U.S.C. 154(b) by 276 days.

This patent is subject to a terminal disclaimer.

(21) Appl. No.: 15/250,590

(22) Filed: Aug. 29, 2016

(65) Prior Publication Data

US 2016/0361132 A1   Dec. 15, 2016

Related U.S. Application Data

(63) Continuation of application No. 14/515,105, filed on Oct. 15, 2014, now Pat. No. 9,498,290, and a
(Continued)

(51) Int. Cl.
*A61B 90/11* (2016.01)
*A61N 1/05* (2006.01)
(Continued)

(52) U.S. Cl.
CPC .............. *A61B 90/11* (2016.02); *A61B 5/055* (2013.01); *A61B 6/032* (2013.01); *A61B 6/5258* (2013.01);
(Continued)

(58) Field of Classification Search
CPC ......... A61B 90/11; A61B 5/055; A61B 6/032; A61B 6/5258; A61B 17/00234;
(Continued)

(56) References Cited

U.S. PATENT DOCUMENTS 5,116,345 A   5/1992   Jewell et al.
5,507,742 A   4/1996   Long et al.
(Continued)

FOREIGN PATENT DOCUMENTS

WO   WO 2012/072112 A1   6/2012

OTHER PUBLICATIONS

Brainlab Airo® Mobile Intraoperative CT, Brochure, 10 pages (2014).
(Continued)

*Primary Examiner* — Tse W Chen
*Assistant Examiner* — Joanne M Hoffman
(74) *Attorney, Agent, or Firm* — Myers Bigel, P.A.

(57) ABSTRACT

A trajectory frame for use with surgical navigation systems includes a base having a patient access aperture formed therein. A yoke is mounted to the base and is rotatable about a roll axis. A platform is mounted to the yoke and is rotatable about a pitch axis. An elongated guide is secured to the platform and includes opposite proximal and distal end portions and a bore that extends from the proximal end portion to the distal end portion. The guide is configured to removably receive various devices therein for quick release therefrom, including an optical tracking probe (which may be a universal tracker) detectable by a camera-based tracking system or an EM probe detectable by an EM navigation system, a microelectrode probe driver adapter, a drill guide and drill bit, skull fixation device and driver, and a catheter guide.

22 Claims, 47 Drawing Sheets

Related U.S. Application Data continuation-in-part of application No. 13/781,049, filed on Feb. 28, 2013.

(60) Provisional application No. 61/891,661, filed on Oct. 16, 2013, provisional application No. 61/673,583, filed on Jul. 19, 2012.

(51) Int. Cl.

| | | |
|---|---|---|
| *A61B 17/17* | (2006.01) | |
| *A61B 17/16* | (2006.01) | |
| *A61M 25/02* | (2006.01) | |
| *A61B 17/00* | (2006.01) | |
| *A61B 6/03* | (2006.01) | |
| *G01R 33/28* | (2006.01) | |
| *G01R 33/48* | (2006.01) | |
| *G01R 33/565* | (2006.01) | |
| *A61B 6/00* | (2006.01) | |
| *A61B 5/055* | (2006.01) | |
| *A61N 1/372* | (2006.01) | |
| *A61B 90/00* | (2016.01) | |
| *A61B 34/20* | (2016.01) | |
| *A61B 90/10* | (2016.01) | |

(52) U.S. Cl.
CPC .... *A61B 17/00234* (2013.01); *A61B 17/1615* (2013.01); *A61B 17/1695* (2013.01); *A61B 17/1703* (2013.01); *A61B 17/1739* (2013.01); *A61M 25/02* (2013.01); *A61N 1/0534* (2013.01); *A61N 1/372* (2013.01); *G01R 33/286* (2013.01); *G01R 33/4812* (2013.01); *G01R 33/565* (2013.01); *A61B 2034/2051* (2016.02); *A61B 2034/2055* (2016.02); *A61B 2090/103* (2016.02); *A61B 2090/3983* (2016.02); *A61M 2025/028* (2013.01); *A61M 2210/0687* (2013.01); *A61M 2210/0693* (2013.01)

(58) Field of Classification Search
CPC ............ A61B 17/1615; A61B 17/1695; A61B 17/1702; A61B 17/1739; A61M 25/02; A61N 1/0534; A61N 1/372; G01R 33/286; G01R 33/4812; G01R 33/565
See application file for complete search history.

(56) References Cited

U.S. PATENT DOCUMENTS

| | | | |
|---|---|---|---|
| 5,592,939 A | 1/1997 | Martinelli et al. | |
| 5,913,820 A | 6/1999 | Bladen et al. | |
| 6,050,992 A | 4/2000 | Nichols | |
| 6,167,311 A | 12/2000 | Rezai | |
| 6,356,786 B1 | 3/2002 | Rezai et al. | |
| 6,405,079 B1 | 6/2002 | Ansarinia | |
| 6,438,423 B1 | 8/2002 | Rezai et al. | |
| 6,526,318 B1 | 2/2003 | Ansarinia | |
| 6,529,765 B1 | 3/2003 | Franck et al. | |
| 6,539,263 B1 | 3/2003 | Schiff et al. | |
| 6,609,030 B1 | 8/2003 | Rezai et al. | |
| 6,675,037 B1 | 1/2004 | Tsekos | |
| 6,708,064 B2 | 3/2004 | Rezai | |
| 6,799,074 B1 | 9/2004 | Thomas et al. | |
| 6,920,347 B2 | 7/2005 | Simon et al. | |
| 6,940,941 B2 | 9/2005 | Gregerson et al. | |
| 6,949,106 B2 | 9/2005 | Brock et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,491,198 B2 | 2/2009 | Kockro | |
| 7,658,879 B2 | 2/2010 | Solar | |
| 7,706,600 B2 | 4/2010 | Kreeger et al. | |
| 7,720,522 B2 | 5/2010 | Solar et al. | |
| 7,730,563 B1 | 6/2010 | Sklar et al. | |
| 7,751,865 B2 | 7/2010 | Jascob et al. | |
| 8,073,530 B2 | 12/2011 | Solar et al. | |
| 8,150,494 B2 | 4/2012 | Simon et al. | |
| 8,175,677 B2 | 5/2012 | Sayler et al. | |
| 8,195,272 B2 | 6/2012 | Piferi et al. | |
| 8,238,631 B2 | 8/2012 | Hartmann et al. | |
| 8,315,689 B2 | 11/2012 | Jenkins et al. | |
| 8,340,743 B2 | 12/2012 | Jenkins et al. | |
| 8,374,677 B2 | 2/2013 | Piferi et al. | |
| 8,543,189 B2 | 9/2013 | Paitel et al. | |
| 2001/0018584 A1 | 8/2001 | Bays | |
| 2003/0181810 A1 | 9/2003 | Murphy et al. | |
| 2004/0075768 A1 | 4/2004 | Law et al. | |
| 2004/0215071 A1 | 10/2004 | Frank et al. | |
| 2005/0242055 A1 | 11/2005 | Oh | |
| 2006/0282044 A1 | 12/2006 | Mohammed | |
| 2007/0129629 A1 | 6/2007 | Beauregard et al. | |
| 2008/0097193 A1 | 4/2008 | Karmarkar | |
| 2008/0214922 A1 | 9/2008 | Hartmann et al. | |
| 2008/0275466 A1 | 11/2008 | Skakoon | |
| 2009/0112084 A1 | 4/2009 | Piferi et al. | |
| 2009/0171184 A1 | 7/2009 | Jenkins et al. | |
| 2010/0125240 A1 | 5/2010 | Spedden et al. | |
| 2010/0160771 A1 | 6/2010 | Gielen et al. | |
| 2010/0229414 A1 | 9/2010 | Nonni et al. | |
| 2011/0083672 A1 | 4/2011 | Webster et al. | |
| 2011/0152860 A1 | 6/2011 | Morejohn et al. | |
| 2012/0046542 A1 | 2/2012 | Csavoy et al. | |
| 2012/0330135 A1 | 12/2012 | Millahn et al. | |
| 2013/0060146 A1 | 3/2013 | Yang et al. | |

OTHER PUBLICATIONS

Brainlab Buzz™ Digital O.R., Brochure, 12 pages (2012).
Brainlab Curve™ Image Guided Surgery, Brochure, 18 pages (2012).
Brainlab, Dash® Digital Cutting Block Alignment Tool, 1 page, Published on Apr. 24, 2014 at URL https://www.youtube.com/watch?v=9Q8iOXVW2P0.
Brainlab, Image-Guided Surgery Platforms, 2 Pages, Retrieved from the internet on Oct. 1, 2014 at URL https://www.brainlab.com/surgery-products/overview-platform-products/.
Brainlab Kick® Purely Navigation Using Optical Tracking, 4 pages, Retrieved from the internet on Jan. 16, 2015 at URL https://www.brainlab.com/en/surgery-products/overview-platform-products/kick-navigation/.
Image Guided Surgery for Brain Tumors, Published on Feb. 26, 2013 at URL http://www.youtube.com/watch?v=tJTR4ty0BW4.
International Search Report and the Written Opinion of the International Searching Authority corresponding to International Application No. PCT/US2014/060644 (14 pages) (dated Jan. 26, 2015).
Medtronic, Deep Brain Stimulation for Movement Disorders, 2 Pages, Retrieved from the internet on Sep. 22, 2014 at URL http://professional.medtronic.com/pt/neuro/dbs-md/prod/procedure-solutions/index.htm.
Medtronic Framelink™, Simplified Planning and Navigation for DBS Procedures, 2 pages (2009).
Medtronic Nexframe Stereotactic Image Guided System, 2 pages, Retrieved from the internet on Jan. 16, 2015 at URL http://professional.medtronic.com/pt/neuro/dbs-md/prod/procedure-solutions/features-specifications/#.VLk0N9LF_To.
Medtronic Stealth Station® Surgical Navigation Systems, Dec. 11, 2014, 2 pages, Retrieved from the internet at URL http://www.medtronic.com/for-healthcare-professionals/products-therapies/spinal/surgical-navigation-imaging/surgical-navigation-systems/.
Northern Digital Inc., NDI, Disposable Reflective Marker Spheres for Brainlab IGS Systems, 4 pages, Retrieved from the internet on Jan. 16, 2015 at URL http://spheres.ndigital.com/
Northern Digital Inc., The Original IGS Sphere, 7 Pages, Retrieved from the internet on Sep. 22, 2014 at URL http://spheres.ndigital.com/ndi-passive-spheres/.

(56) References Cited

OTHER PUBLICATIONS

Photographs obtained of commercial probe tracking devices, date photographs on internet first available unknown, but prior to filing the pending application on Oct. 15, 2014, 1 page.
Stryker eNlite Navigation System, 1 page, Retrieved from the internet on Jan. 16, 2015 from URL http://www.stryker.com/latm/products/OREquipmentConnectivity/SurgicalNavigation/SurgicalNavigationSystems/EnliteLaptop/index.htm.
Stryker Integrated NavSuite Operating Room, 2008, Brochure, 3 pages.
Stryker System II Navigation System, 2006, Brochure, 2 pages.

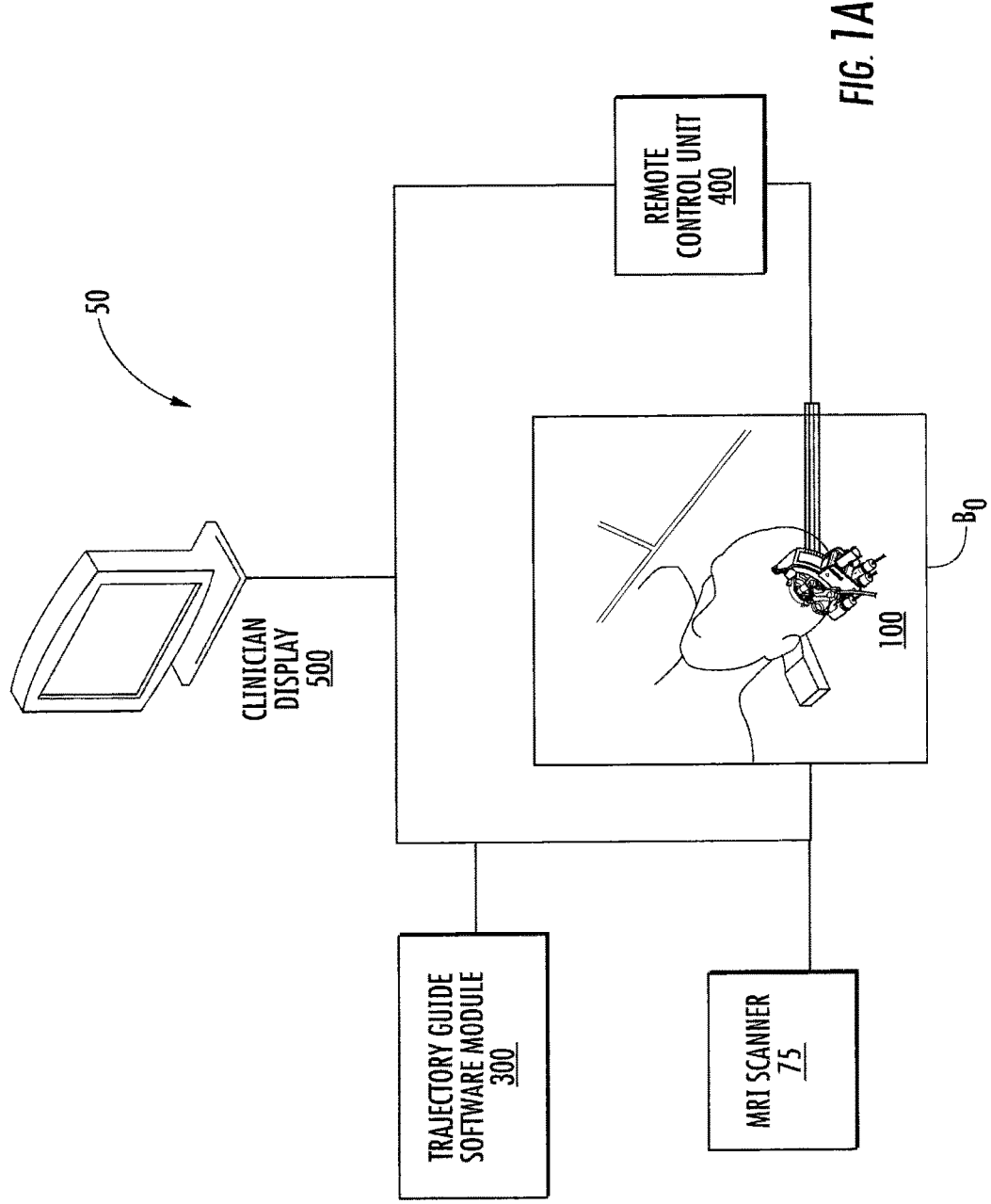

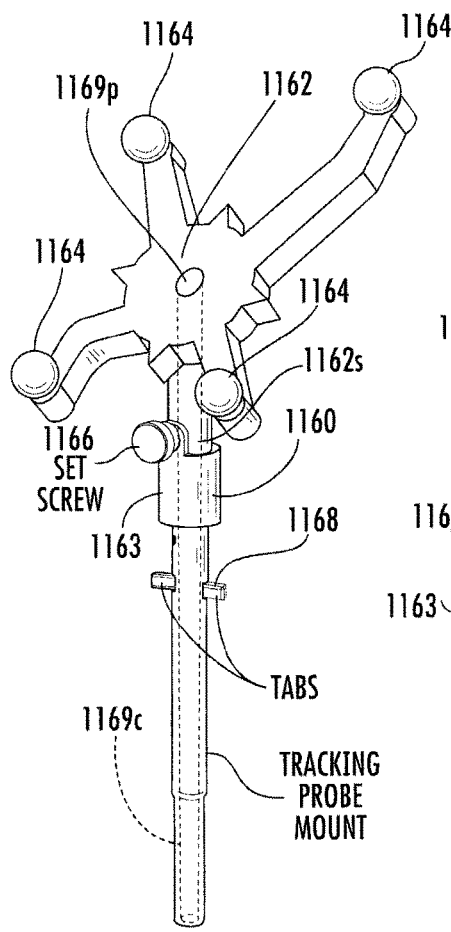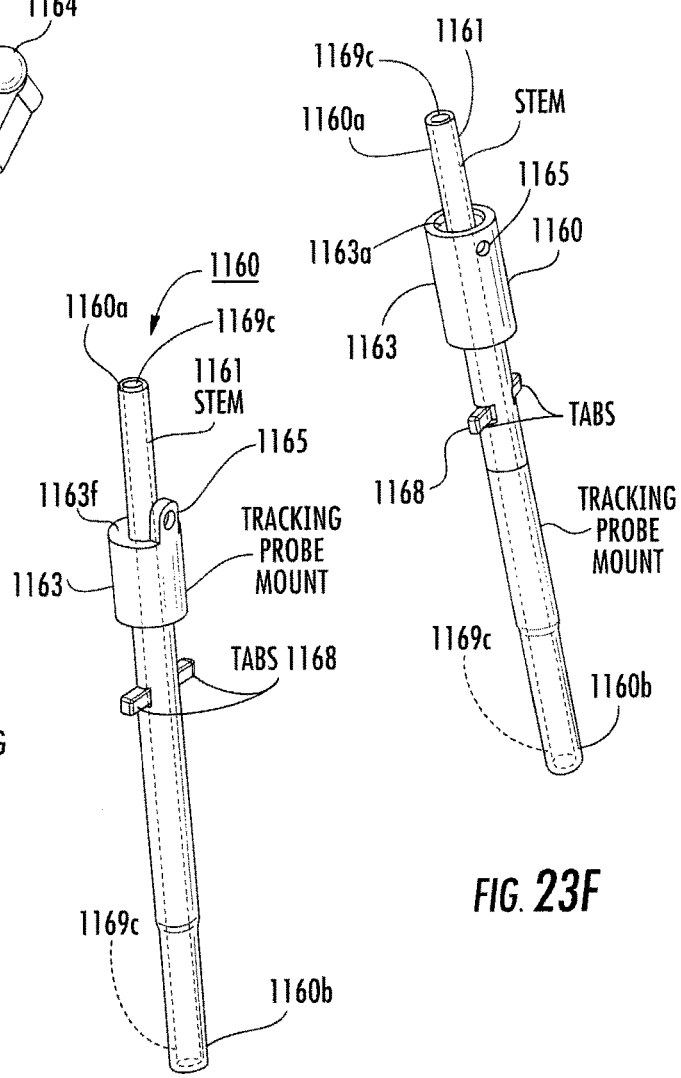
FIG. 23D
FIG. 23E
FIG. 23F

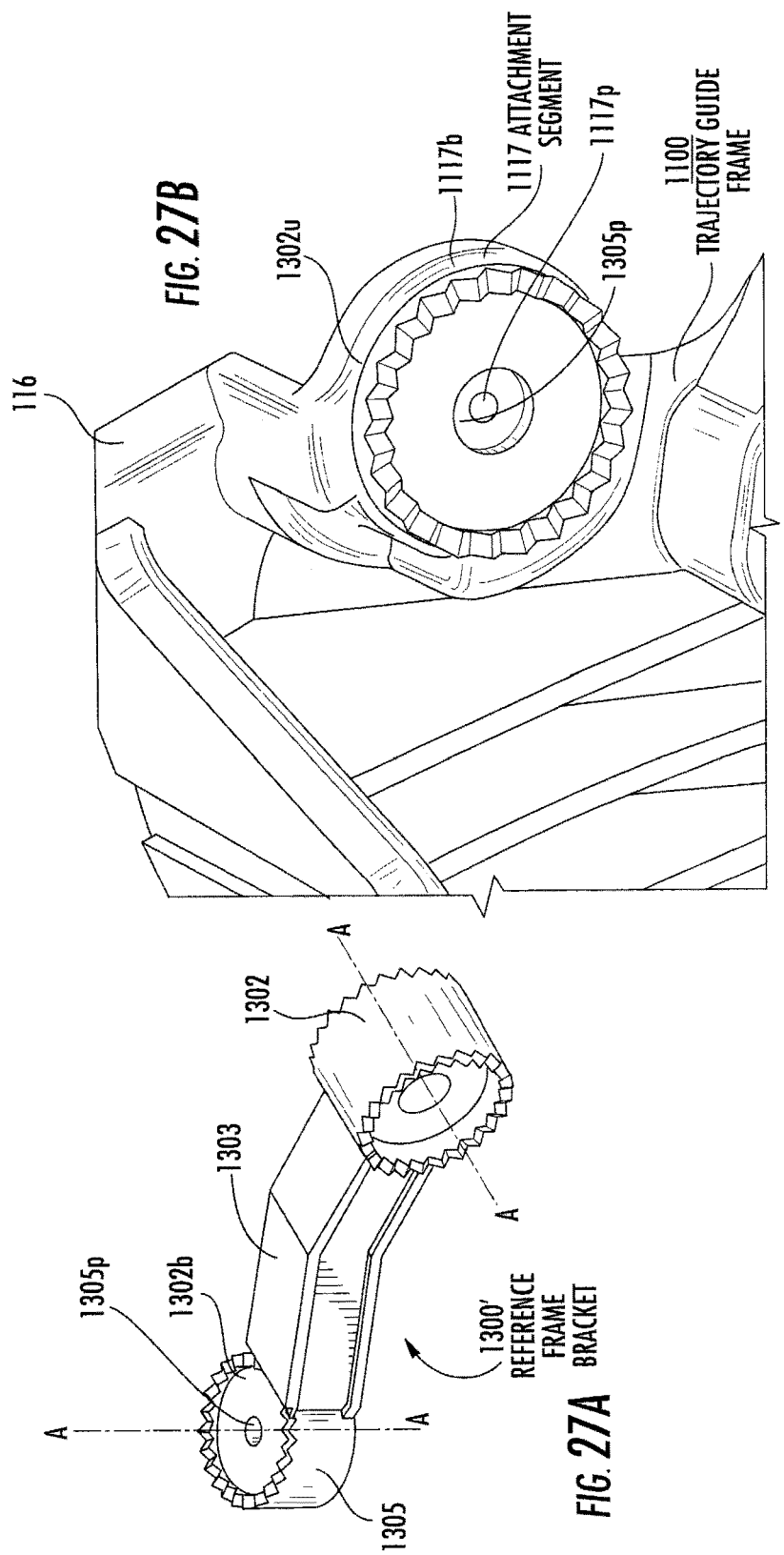

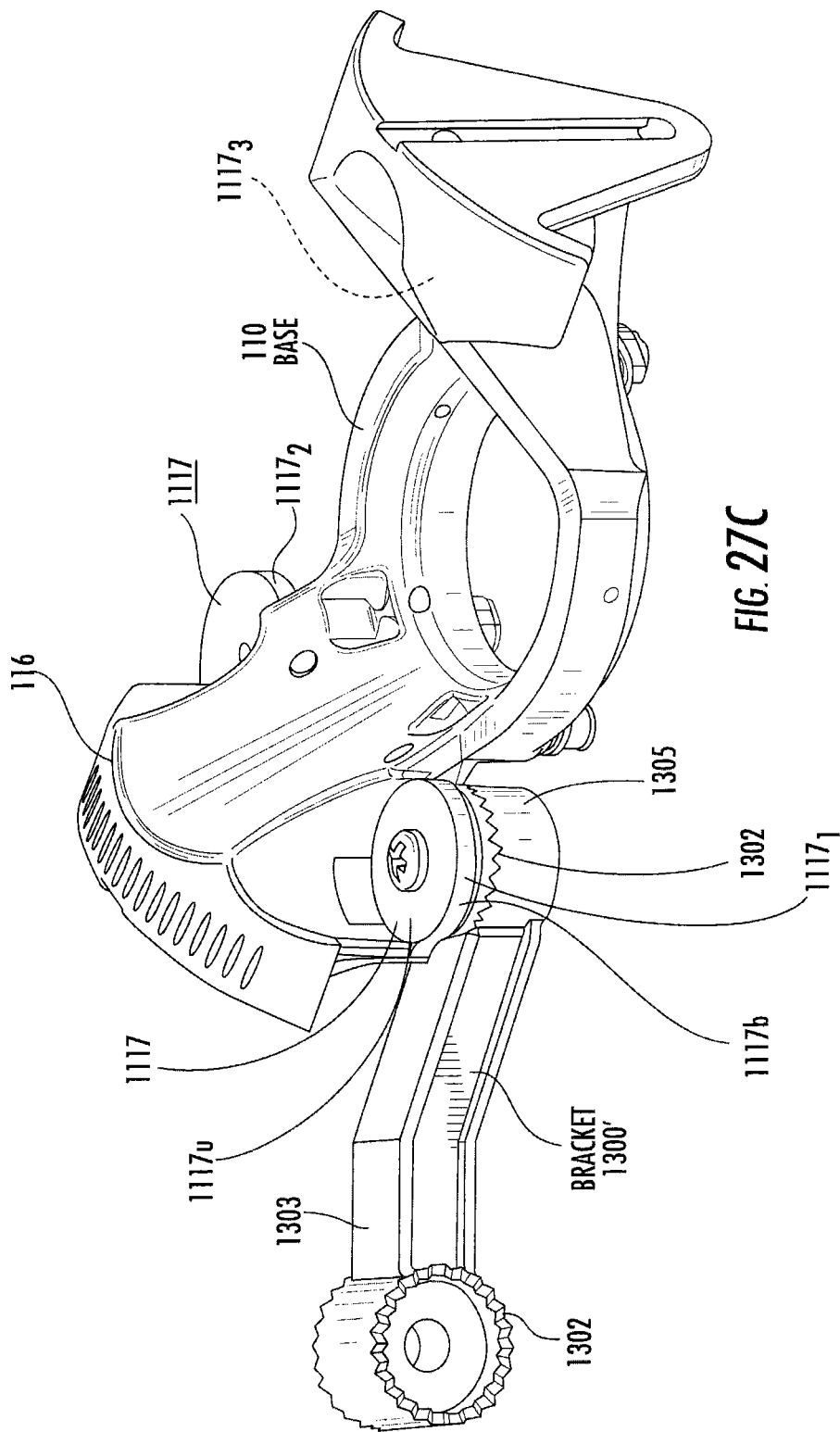

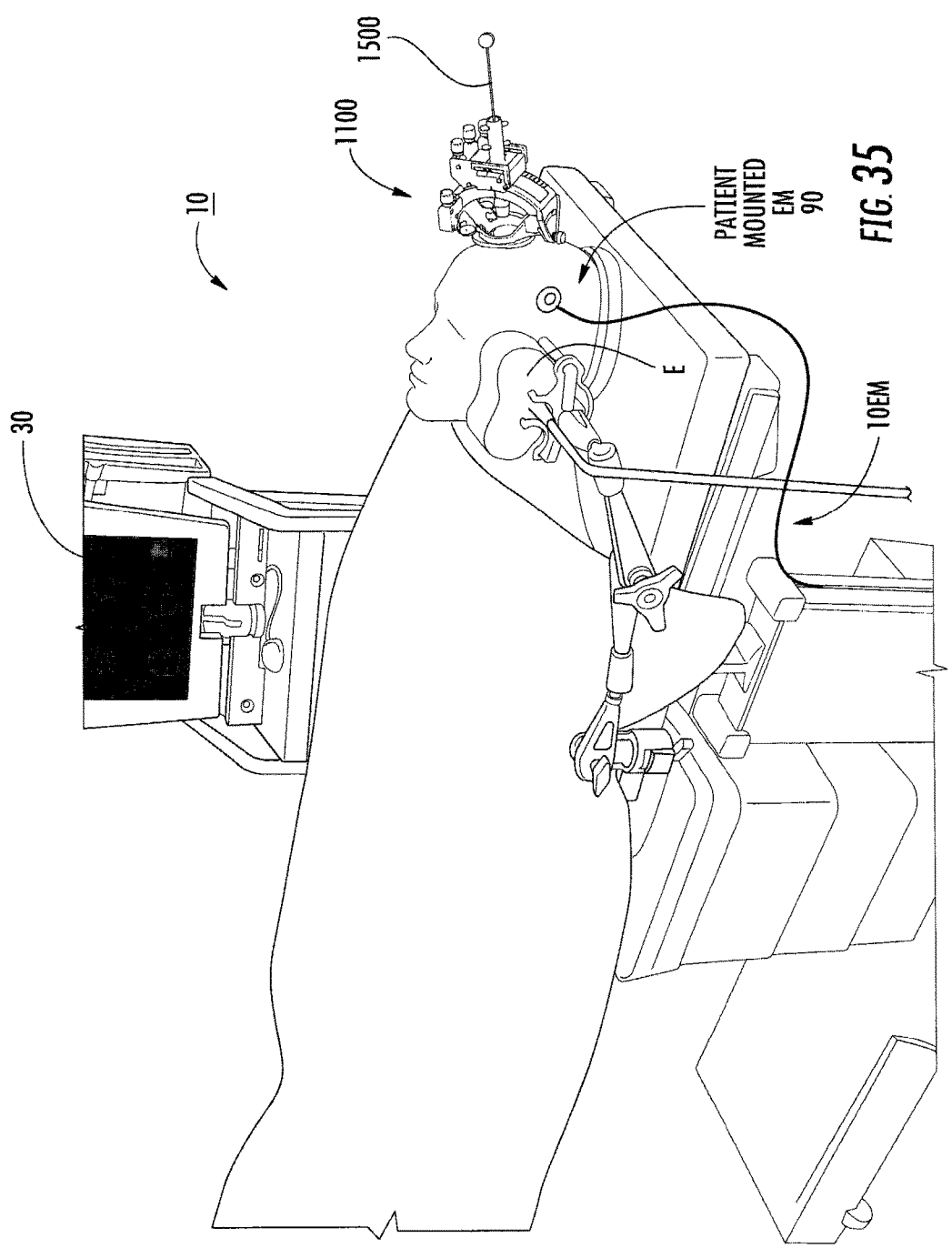

SURGICAL NAVIGATION DEVICES AND METHODS

RELATED APPLICATIONS

This application is a continuation of U.S. patent application Ser. No. 14/515,105, filed Oct. 15, 2014, which is a continuation-in-part of U.S. patent application Ser. No. 13/781,049, filed Feb. 28, 2013, which claims the benefit of and priority to U.S. Provisional Patent Application Ser. No. 61/673,583 filed Jul. 19, 2012. This application also claims the benefit of and priority to U.S. Provisional Patent Application Ser. No. 61/891,661, filed Oct. 16, 2013. The contents of the above documents are incorporated herein by reference as if set forth in their entirety.

FIELD OF THE INVENTION

The present invention relates generally to medical systems and methods and, more particularly, to in vivo medical systems and methods.

BACKGROUND

During image guided surgeries, it can be desired to drill through bone such as a skull to define a surgical path for passing medical interventional devices.

SUMMARY

Embodiments of the present invention provide methods, devices and systems for localized placement and/or delivery of diagnostic or therapeutic devices or substances.

According to embodiments of the present invention, an image guided interventional system includes a frame with a support column and a removable, cooperating tubular adapter. The base of the frame is configured to be secured to the body of a patient, and is configured to translate and rotate such that the support column can be oriented to a desired intrabody trajectory.

Embodiments of the present invention may be particularly suitable for placing neuro-modulation leads, such as Deep Brain Stimulation ("DBS") leads, implantable parasympathetic or sympathetic nerve chain leads and/or CNS stimulation leads, as well as other devices within the brain.

Embodiments of the present invention may be suitable for a number of interventional procedures in many locations inside the body including, but not limited to, brain, cardiac, spinal, urethral, and the like.

Embodiments of the present invention may be suitable for a number of image guided drug delivery procedures to intra-brain or other intra-body targeted locations.

Embodiments of the present invention may be suitable for a number of image-guided tumor removal procedures.

A plurality of user-activatable actuators can be operably connected to the frame and configured to translate and rotate the frame relative to the body of a patient so as to position the support column to define a desired intrabody trajectory. In some embodiments, the actuators are dials or thumbscrew-type devices that allow manual manipulation thereof. In other embodiments, the actuators are manipulated remotely using remote controls and cables.

The support column can include an axially-extending guide bore therethrough that is configured to guide placement of an interventional device in vivo. Various instrumentation and equipment (e.g., stimulation leads, ablation probes or catheters, injection or fluid delivery devices, biopsy needles, extraction tools, etc.) can be inserted through the support column to execute diagnostic and/or surgical procedures.

According to some embodiments of the present invention, the frame includes a base, a yoke movably mounted to the base and that is rotatable about a roll axis, and a platform movably mounted to the yoke and that is rotatable about a pitch axis. The platform includes an X-Y support table that is configured to move in an X-direction and Y-direction relative to the platform. The base has a patient access aperture formed therein, and is configured to be secured to the body of a patient such that the aperture overlies an opening in the body. A roll actuator is operably connected to the yoke and is configured to rotate the yoke about the roll axis. A pitch actuator is operably connected to the platform and is configured to rotate the platform about the pitch axis. An X-direction actuator is operably connected to the platform and is configured to move the X-Y support table in the X-direction. A Y-direction actuator is operably connected to the platform and is configured to move the X-Y support table in the Y-direction.

The base may include a plurality of locations for attachment to a body of a patient via fasteners. In some embodiments, one or more attachment locations may include multiple adjacent apertures configured to receive a fastener therethrough. For embodiments where the frame is configured to be attached to the skull of a patient, the base can be configured to be secured to the skull of a patient such that the patient access aperture overlies a burr hole formed in the patient skull.

According to some embodiments of the present invention, the yoke includes a pair of spaced apart arcuate arms. The platform engages and moves along the yoke arcuate arms when rotated about the pitch axis. The base includes at least one arcuate arm. The yoke engages and moves along the base arcuate arm when rotated about the roll axis.

According to some embodiments of the present invention, at least one of the yoke arcuate arms includes a thread pattern formed in a surface thereof. The pitch actuator includes a rotatable worm with teeth configured to engage the thread pattern. Rotation of the worm causes the platform to rotate about the pitch axis. Similarly, at least one of the base arcuate arms includes a thread pattern formed in a surface thereof. The roll actuator includes a rotatable worm with teeth configured to engage the thread pattern, and wherein rotation of the worm causes the yoke to rotate about the roll axis.

In some embodiments, the actuators are color-coded such that each different actuator has a respective different color. This allows a user to quickly determine which actuator is the correct one for a particular desired movement of the frame.

An elongated tubular guide extends through the platform and yoke along a Z-direction and includes opposite proximal and distal end portions. The guide distal end portion is positioned proximate the patient access aperture. The guide includes a bore therethrough that extends from the proximal end portion to the distal end portion, and the guide is configured to removably receive different devices within the bore. The devices may have different sizes and configuration. Exemplary devices include a tracking device with an array of optical fiducials, a microelectrode drive, a catheter guide, etc.

In some embodiments of the present invention, the guide proximal end portion includes threads formed therein that are configured to threadingly engage a portion of a device inserted within the guide for quick release therefrom. In other embodiments of the present invention, the guide proximal end portion is configured to removably retain a portion of a device inserted within the guide for quick release therefrom, without the use of threads. For example, the guide proximal end portion may include a detent, or other type of structure (shape and/or component), formed therein, and a device includes a portion having a protrusion configured to engage the detent so as to removably secure the device to the guide via a snap fit. Alternatively, the guide proximal end portion may include a protrusion and the device may include a portion having a detent formed therein that is configured to engage the protrusion so as to removably secure the device to the guide via a snap fit. The term "quick release," as used herein, means that a technician or other user can quickly (e.g., typically in under about 1 minute or under about 30 seconds) remove a device from the guide with little effort and without requiring tools.

According to some embodiments of the present invention, a medical assembly includes a trajectory frame and a plurality of devices that are releasably and serially inserted within the frame so as to be positioned adjacent to a body of a patient. Exemplary devices include a tracking device with an array of optical fiducials, a microelectrode drive, a catheter guide, a targeting cannula, a drill guide and drill bit, a skull fixation device and driver, and the like.

The frame includes a base configured to be secured to the body of a patient and having a patient access aperture formed therein, a yoke movably mounted to the base and rotatable about a roll axis, and a platform movably mounted to the yoke and rotatable about a pitch axis. The platform may include an X-Y support table movably mounted thereto that is configured to move in an X-direction and Y-direction relative to the platform. An elongated guide is secured to the X-Y support table and includes opposite proximal and distal end portions, and a bore therethrough that extends from the proximal end portion to the distal end portion. The guide distal end portion is positioned proximate the patient access aperture. A device is inserted within the bore, and includes opposite proximal and distal end portions. The device distal end portion is positioned proximate the patient access aperture, and the device proximal end portion is removably secured to the guide proximal end portion.

In some embodiments, the guide proximal end portion includes threads formed therein, and the device comprises a portion configured to threadingly engage the guide proximal end portion. In other embodiments, the device may include a portion configured to be removably secured to the guide proximal end portion via a snap fit. In yet further embodiments, the guide proximal end portion includes at least one slot and the device is removably secured within the guide bore via at least one member extending outwardly from the device that cooperates with the at least one slot.

In some embodiments, the guide is removably secured to the X-Y support table such that the guide can be removed and replaced with another guide of a different size/configuration.

According to some embodiments of the present invention, an interventional method includes affixing a frame with a cooperating guide to the skull of a patient, inserting an adapter holding a tracking probe with an array of optical fiducials within the guide, tracking the fiducials using a camera system, and removing the adapter from the guide.

The method may be carried out in a conventional operating room using off-the-shelf image guided systems without requiring modification to operational software.

The method may be carried out in an operating room using a camera based tracking system.

The method may be carried out using images acquired from a CT scanner during the procedure and/or using pre-acquired MRI images (typically, for neuro-using both pre-acquired MRI brain images and CT images at one or times during the procedure).

The method may optionally be carried out in an MRI suite.

The method may further include removably securing a drill guide within the guide, inserting a drill bit within the lumen of the drill guide, and drilling a hole within the skull of the patient at the incision via the drill bit. The method may further include removing the drill guide and drill bit from the targeting cannula, removably securing a skull (and/or scalp) fixation device to a distal end of the targeting cannula guide, removably inserting a skull (and/or scalp) fixation device driver within the targeting cannula guide, wherein the fixation device driver is configured to cooperate with the skull and/or scalp fixation device, and rotating the skull fixation device driver to cause the fixation device to be inserted within the hole in the skull of the patient. The fixation device driver is removed from the guide, a catheter guide is removably secured within the guide, and a catheter is advanced through the catheter guide.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIG. 1A is a block diagram of an MRI-guided interventional system, according to some embodiments of the present invention.

FIG. 23D is a side perspective view of a tracking probe mount holding the tracking probe for releasable attachment to the support column of the trajectory frame shown in FIG. 22B according to embodiments of the present invention.

FIGS. 23E and 23F are side perspective views of exemplary tracking probe mounts, shown without the tracking probe, according to embodiments of the present invention.

FIG. 27A is a side perspective view of another exemplary attachment bracket according to embodiments of the present invention.

FIG. 27B is an enlarged partial assembly view of a portion of a connector attached to the reference frame bracket shown in FIG. 27A, assembled to an attachment segment of the trajectory frame according to embodiments of the present invention.

FIG. 27C is an enlarged partial assembly view of the reference frame attachment bracket shown in FIG. 27A according to embodiments of the present invention.

FIG. 35 is a schematic illustration of an EM-based navigation system according to embodiments of the present invention.

DETAILED DESCRIPTION

Figure 1B:
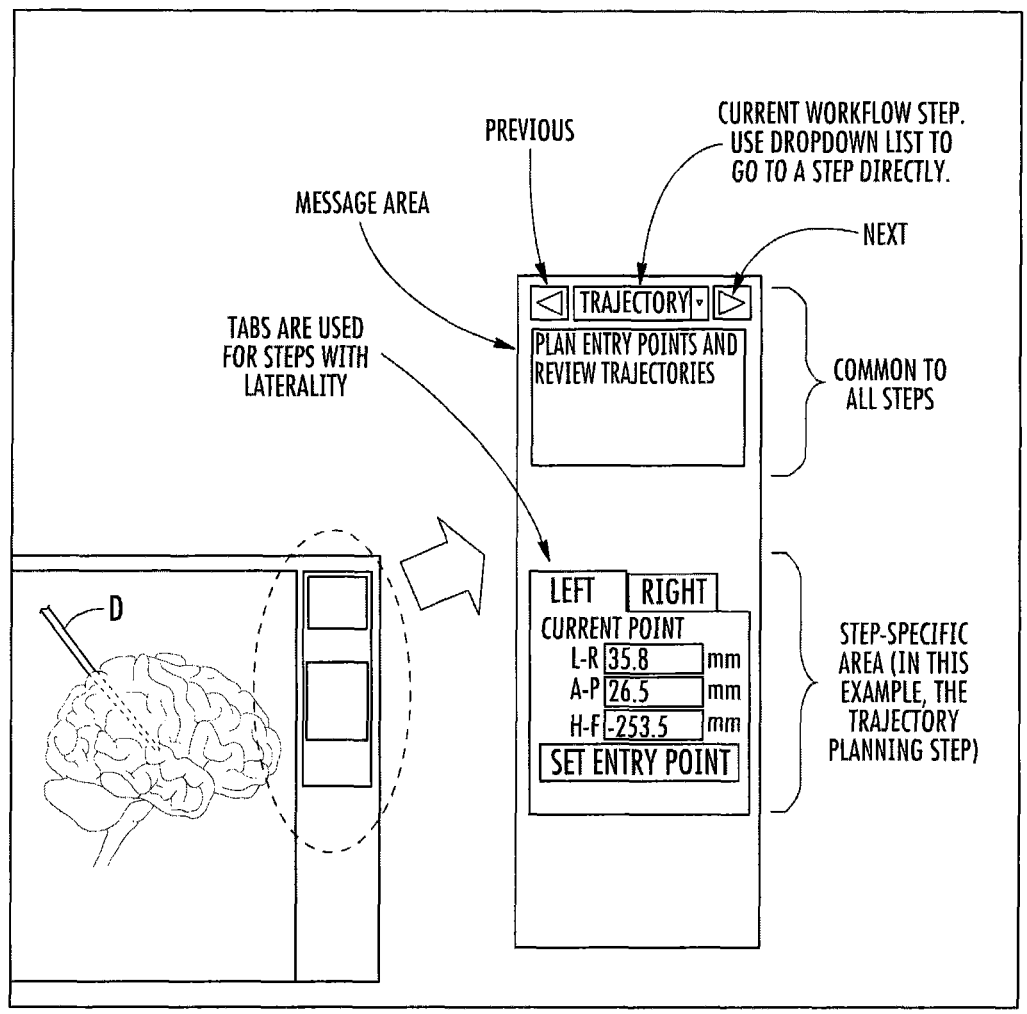
FIG. 1B illustrates a user interface that displays, and that allows a user to adjust, the trajectory of a targeting cannula, according to some embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about", as used herein with respect to a value or number, means that the value or number can vary by +/−twenty percent (20%).

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "high-magnetic field" refers to field strengths above about 0.5 T (Tesla), typically above 1.0 T, and more typically between about 1.5 T and 10 T.

The term "targeting cannula" refers to an elongate device, typically having a substantially tubular body that can be oriented to provide positional data relevant to a target treatment site and/or define a desired access path orientation or trajectory. At least portions of a targeting cannula contemplated by embodiments of the invention can be configured to be visible in an MRI image, thereby allowing a clinician to visualize the location and orientation of the targeting cannula in vivo relative to fiducial and/or internal tissue landscape features.

The term "cannula" refers to an elongate device that can be associated with a trajectory frame that attaches to a patient, but does not necessarily enter the body of a patient.

The term "imaging coils" refers to a device that is configured to operate as an MRI receive antenna. The term "coil" with respect to imaging coils is not limited to a coil shape but is used generically to refer to MRI antenna configurations, loopless, looped, etc., as are known to those of skill in the art. The term "fluid-filled" means that the component includes an amount of the fluid but does not require that the fluid totally, or even substantially, fill the component or a space associated with the component. The fluid may be an aqueous solution, MR contrast agent, or any material that generates MRI signal.

The term "two degrees of freedom" means that a trajectory frame described herein allows for at least translational (swivel or tilt) and rotational movement over a fixed site, which may be referred to as a Remote Center of Motion (RCM).

The terms "ACPC coordinate space" or "AC-PC orientation" refers to a right-handed coordinate system defined by anterior and posterior commissures (AC, PC) and Mid-Sagittal plane points, with positive directions corresponding to a patient's anatomical Right, Anterior and Head directions with origin at the mid-commissure point.

Embodiments of the present invention can be configured to guide and/or place diagnostic or interventional devices and/or therapies to any desired internal region of the body or object using MRI and/or in an MRI scanner or MRI interventional suite or using other image guided systems not requiring an MRI system or suite.

The object can be any object, and may be particularly suitable for animal and/or human subjects. Some embodiments can be sized and configured to place implantable DBS leads for brain stimulation, typically deep brain stimulation. Some embodiments can be configured to deliver tools or therapies that stimulate a desired region of the sympathetic nerve chain. Other uses inside or outside the brain include stem cell placement, gene therapy or drug delivery for treating physiological conditions. Some embodiments can be used to treat tumors. Some embodiments can be used for RF ablation, laser ablation, cryogenic ablation, etc.

In some embodiments, the trajectory frame and/or interventional tools can be configured to facilitate high resolution imaging via integral intrabody imaging coils (receive antennas), high intensity focused ultrasound (HIFU), and/or the interventional tools can be configured to stimulate local tissue, which can facilitate confirmation of proper location by generating a physiologic feedback (observed physical reaction or via fMRI).

Some embodiments can be used to deliver bions, stem cells or other target cells to site-specific regions in the body, such as neurological target sites and the like. In some embodiments, the systems deliver stem cells and/or other cardio-rebuilding cells or products into cardiac tissue, such as a heart wall via a minimally invasive image guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

Generally stated, some embodiments of the invention are directed to interventional procedures and provide interventional tools and/or therapies that may be used to locally place interventional tools or therapies in vivo to site-specific regions using an image guided system. The interventional tools can be used to define a trajectory or access path to an in vivo treatment site. Some embodiments of the invention provide interventional tools that can provide positional data regarding location and orientation of a tool in 3-D space with a visual confirmation on an image. Embodiments of the invention may provide an integrated system or trajectory frames and components that can be used with one or more of commercially available conventional image guided systems that may allow physicians to place interventional devices/leads and/or therapies accurately.

Some embodiments configure devices so that they are compatible with several imaging modalities and/or image-guided systems.

For MRI uses, the systems may allow for shorter duration procedures over conventional systems (typically under six hours for DBS implantation procedures, such as between about 1-5 hours).

In some embodiments, a pre-operative image such as an MRI image can be used to visualize (and/or locate) a therapeutic region of interest inside the brain or other body locations. During surgery, the MRI or other pre-operative image can be used to visualize (and/or locate) an interventional tool or tools that will be used to deliver therapy and/or to place a chronically implanted device that will deliver therapy.

In some embodiments, the three-dimensional data produced by an MRI-guided interventional system regarding the location of the therapeutic region of interest and the location of the interventional tool can allow the system and/or physician can make positional adjustments to the interventional tool so as to align the trajectory of the interventional tool with the region of interest, so that when inserted into the body, the interventional tool will intersect with the therapeutic region of interest.

In some embodiments, a camera based tracking system can be used.

The IGS systems can have a hardware component and a software component. In some embodiments, the hardware component includes a camera and workstation that can be used for many applications such as cranial, spine, orthopedic, ENT. There can be different software packages or modules for each system for each application.

When the MRI system and/or the camera based image guided system confirms alignment is proper, the interventional tool aligned with the therapeutic region of interest, an interventional probe can be advanced, such as through an open lumen inside of the interventional tool, so that the interventional probe follows the trajectory of the interventional tool and proceeds to the therapeutic region of interest. It should be noted that the interventional tool and the interventional probe may be part of the same component or structure. A sheath may optionally form the interventional tool or be used with an interventional probe or tool.

In particular embodiments, using MRI in combination with local or internal imaging coils and/or MRI contrast material that may be contained at least partially in and/or on the interventional probe or sheath, the location of the interventional probe within the therapeutic region of interest can be visualized on a display or image and allow the physician to either confirm that the probe is properly placed for delivery of the therapy (and/or placement of the implantable device that will deliver the therapy) or determine that the probe is in the incorrect or a non-optimal location. Assuming that the interventional probe is in the proper desired location, the therapy can be delivered and/or the interventional probe can be removed and replaced with a permanently implanted therapeutic device at the same location.

In some embodiments, in the event that the physician determines from the MRI image produced by the MRI and the imaging coils, which may optionally be contained in or on the interventional probe, that the interventional probe is not in the proper location, a new therapeutic target region can be determined from the MRI images, and the system can be updated to note the coordinates of the new target region. The interventional probe is typically removed (e.g., from the brain) and the interventional tool can be repositioned so that it is aligned with the new target area. The interventional probe can be reinserted on a trajectory to intersect with the new target region. Although described and illustrated herein with respect to the brain and the insertion of deep brain stimulation leads, it is understood that embodiments of the present invention may be utilized at other portions of the body and for various other types of procedures.

Embodiments of the present invention will now be described in detail below with reference to the figures. FIG. 1A is a block diagram of an MRI-guided interventional system 50, according to some embodiments of the present invention. The illustrated system 50 includes an MRI scanner 75, a trajectory frame 100 attached to the body of a patient positioned within a magnetic field $B_0$ of the MRI scanner 75, a remote control unit 400, a trajectory guide software module 300, and a clinician display 500. The trajectory frame 100 is configured to support various devices including a targeting cannula through which various interventional devices may be inserted into the body of a patient. The frame 100 is adjustable such that the targeting cannula is rotatable about a pitch axis, about a roll axis, and such that the targeting cannula can translate in X-Y directions relative to a Z-direction defined by a guide configured to support devices such as a targeting cannula. The frame 100 may be attached to the body of a patient directly or indirectly and may be configured to be attached to various parts of the body.

Figure 33:
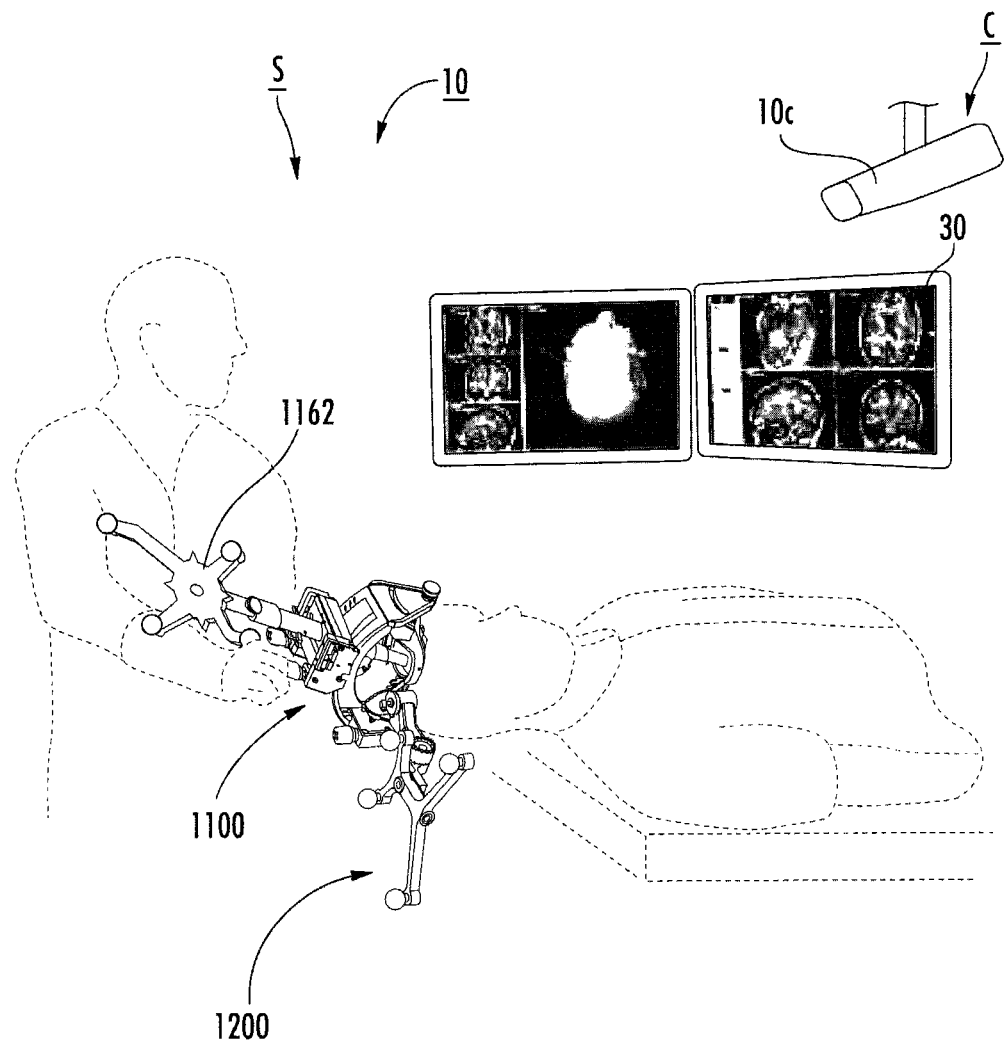
FIG. 33 is a schematic illustration of a camera-based navigation system according to embodiments of the present invention.
Figure 34A:
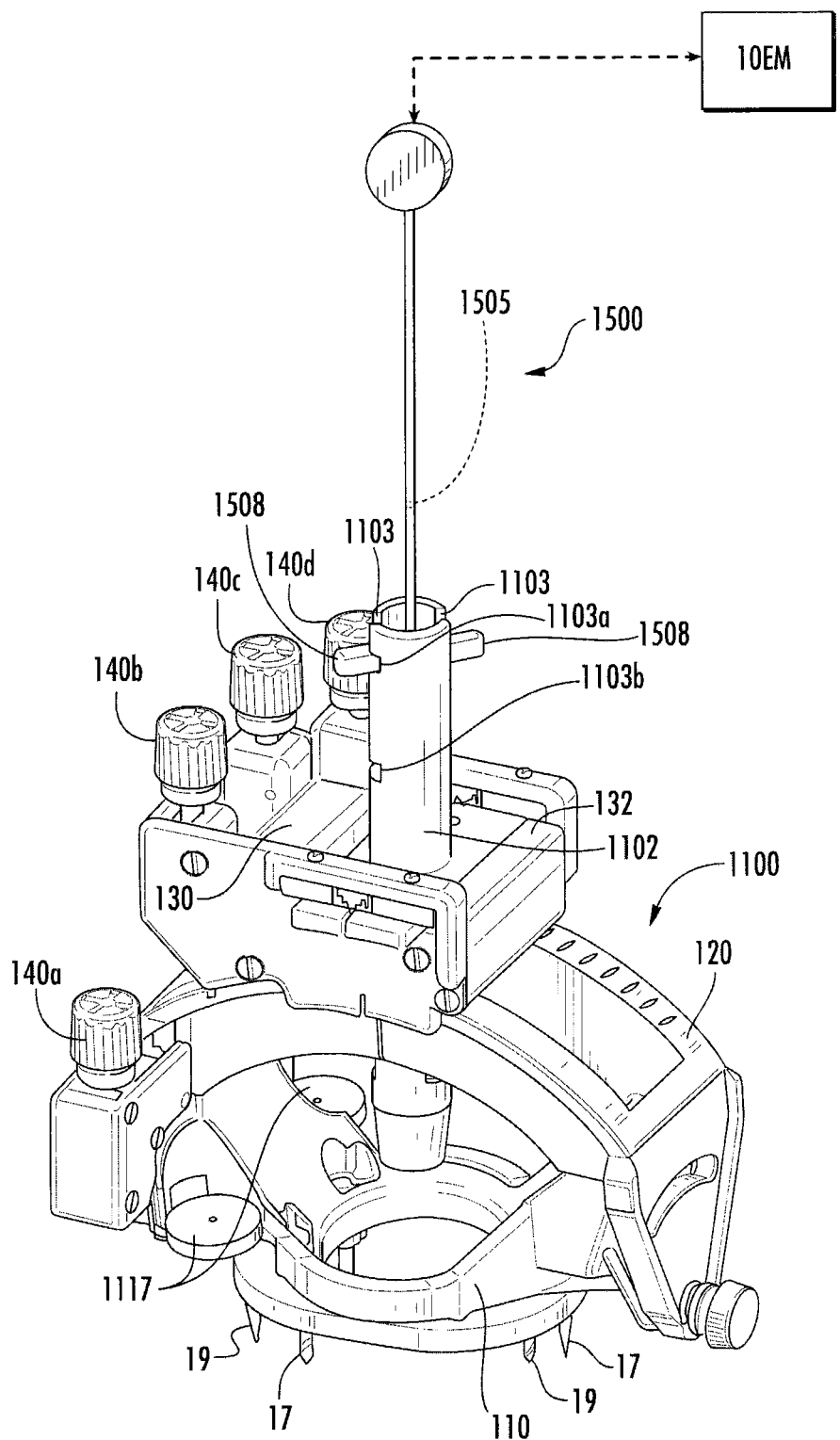
FIG. 34A is a schematic illustration of a trajectory frame with an EM tracking probe according to embodiments of the present invention.

FIG. 33 illustrates an image-guided system that can be used for non-MRI image guided systems. The trajectory frame 1100 and some or all of its cooperating components may be configured to be compatible for use in MRI and CT and/or camera C based image guided systems "S." In some embodiments, separate versions of the trajectory frame 1100 and some or all cooperating components may be provided as CT and/or camera based configurations that may use different materials or components. For example, a camera guided system C does not require a targeting cannula 200 but instead can use a tracking probe, e.g., 1162 (FIG. 21) or universal tracker 1190 (FIG. 31A) or an EM navigation system 10EM with an EM probe 1500 (FIG. 34A/35).

To be clear, the term "image guided system" is used generally to refer to surgical navigation systems that include displays with patient images (which may be acquired before a surgery and/or at defined points during a surgery to confirm location) but does not require a continuous series of images from an imaging modality, such as a CT or MRI scanner, during the surgery.

Figure 11:
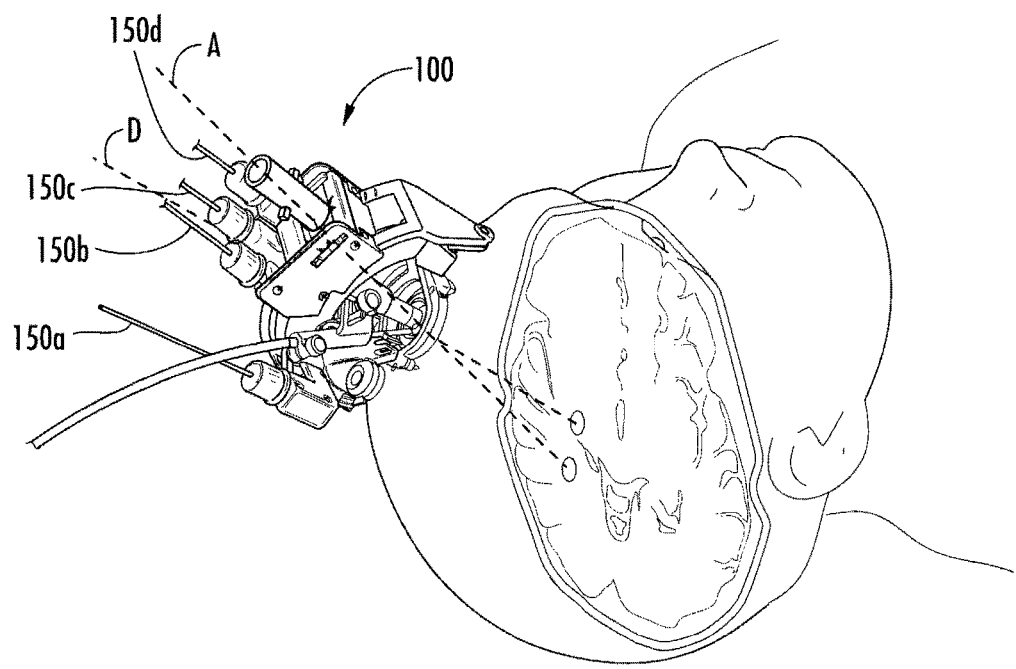
FIG. 11 illustrates the trajectory frame of FIG. 3A secured to the skull of a patient and illustrates a desired trajectory for an interventional device, and also illustrates the actual trajectory of the interventional device as oriented by the frame.
Figure 12:
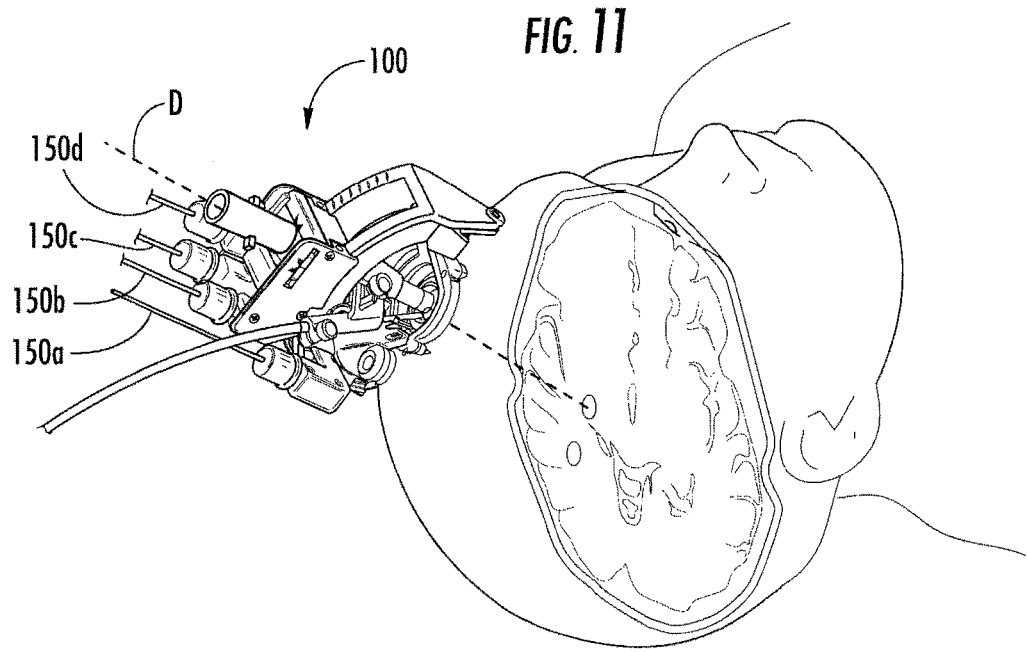
FIG. 12 illustrates the frame of FIG. 11 after reorientation via manipulation of one or more trajectory frame actuators such that the actual trajectory is adjusted to be in alignment with the desired trajectory.

In some embodiments, a remote control unit 400 is provided to allow a user to remotely adjust the position of the targeting cannula or other devices supported by the trajectory frame 100. The system 50 can include a trajectory guide software module 300 that allows a user to define and visualize, via display 500, a desired trajectory (D, FIGS. 1B, 11-12) into the body of a patient of an interventional device extending through the targeting cannula. The trajectory guide software module 300 also allows the user to visualize and display, via display 500, an actual trajectory (A, FIG. 11) into the body of an interventional device extending through the targeting cannula. The trajectory guide software module 300 displays to the user positional adjustments (FIG. 1B) (e.g., pitch axis rotation, roll axis rotation, X-Y translation) needed to align the actual trajectory of the targeting cannula with the desired trajectory path. In addition, the user can view, via display 500, the actual trajectory changing as he/she adjusts the position of the targeting cannula. The trajectory guide software module 300 can be configured to indicate and display when an actual trajectory is aligned with a desired trajectory.

In some embodiments, the trajectory guide software module can be an off-the-shelf module provided with conventional image guided systems that does not require any (or insignificant) modification. That is, the trajectory frame 1100 (FIG. 21) can be configured to accommodate defined, conventional shapes of optical fiducial components, e.g., 4 spheres or 3 spheres in a defined array orientation 1204a, 1164a, 1194a, of reference tracking frames 1200 (FIG. 22) and/or tracking probes 1162, 1190 (FIG. 22, 31A). Examples of known commercial systems with trajectory guide software modules for camera based image guided systems that can be used with configurations of the trajectory frames and cooperating components include, for example systems from Brainlab, Inc., Stryker Medical and Medtronic Inc.

The IGS systems have a hardware and software component. The hardware component includes a camera and workstation can be used for many applications such as cranial, spine, orthopedic, ENT. There can be different software packages or modules for each system for each application. For example, one Medtronic system includes the Stealth Station as a hardware component and the software is called Framelink®. Medtronic, Inc. (Minneapolis, Minn.) also has a Nexframe® stereotactic image guided system.

Examples of Stryker's navigation systems include the Navigation System II, the eNlite Navigation System, and a seamlessly integrated NavSuite Operating Room. Brainlab systems include the Curve™ Image Guided Surgery system is a command and control system for information-guided surgery. Brainlab also offers Kick® Purely Navigation software control with either optical or electromagnetic (EM) tracking as well as Dash® Digital Cutting Block Alignment as a software-guided cutting block alignment tool, Airo® Mobile Intraoperative CT intended for the O.R. and Buzz™ Digital O.R. which displays and enhances DICOM images.

Figure 2A:
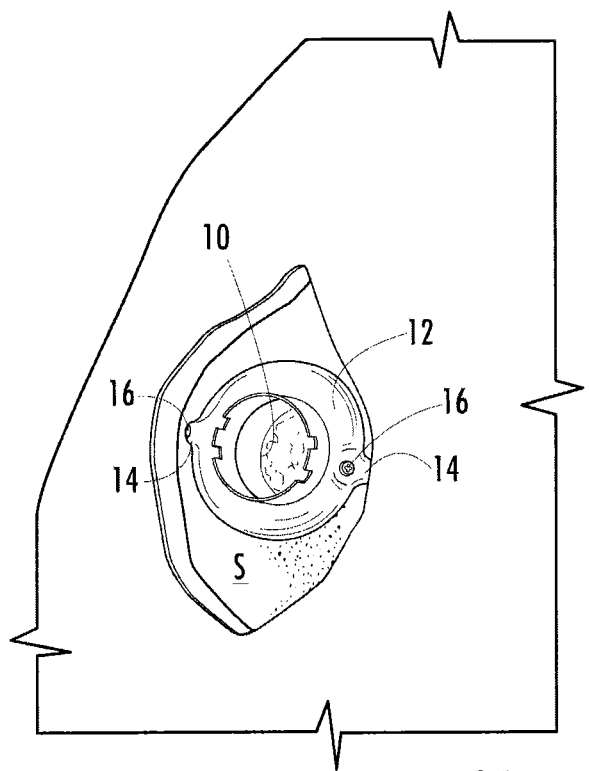
FIG. 2A is a top perspective view of a burr hole formed in the skull of a patient, and a burr hole ring overlying the burr hole and secured to the skull.

FIG. 2A illustrates a burr hole 10 formed in the skull S of a patient. A burr hole ring 12 overlies the burr hole 10 and is secured to the skull S. The illustrated burr hole ring 12 has at least one pair of ears 14, each ear configured to receive a respective fastener (e.g., screw) therethrough for securing the burr hole ring 12 to the skull. In the illustrated embodiment, the burr hole ring 12 is secured to the skull S via screws 16.

Figure 2B:
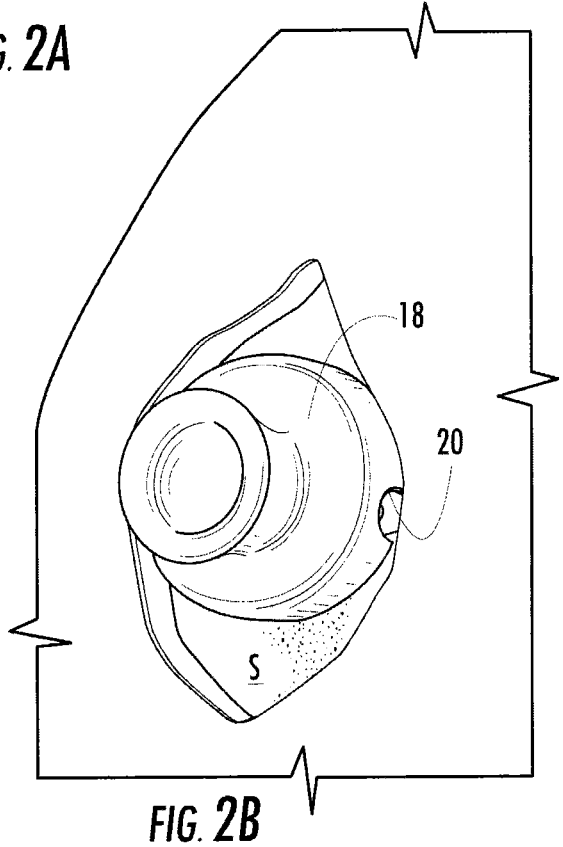
FIG. 2B is a top perspective view of a removable centering device positioned on the burr hole ring of FIG. 1A.

FIG. 2B illustrates an optional removable centering device 18 positioned on the burr hole ring 12. The centering device 18 includes slots, channels, or other recessed or cut out portions 20 that fit over the ears 14 of the burr hole ring 12. The function of the centering device 18 is to facilitate centering a trajectory frame 100, described below, over the burr hole 10. After the trajectory frame 100 is attached to the skull of a patient, the centering device 18 is removed.

Figure 3A:
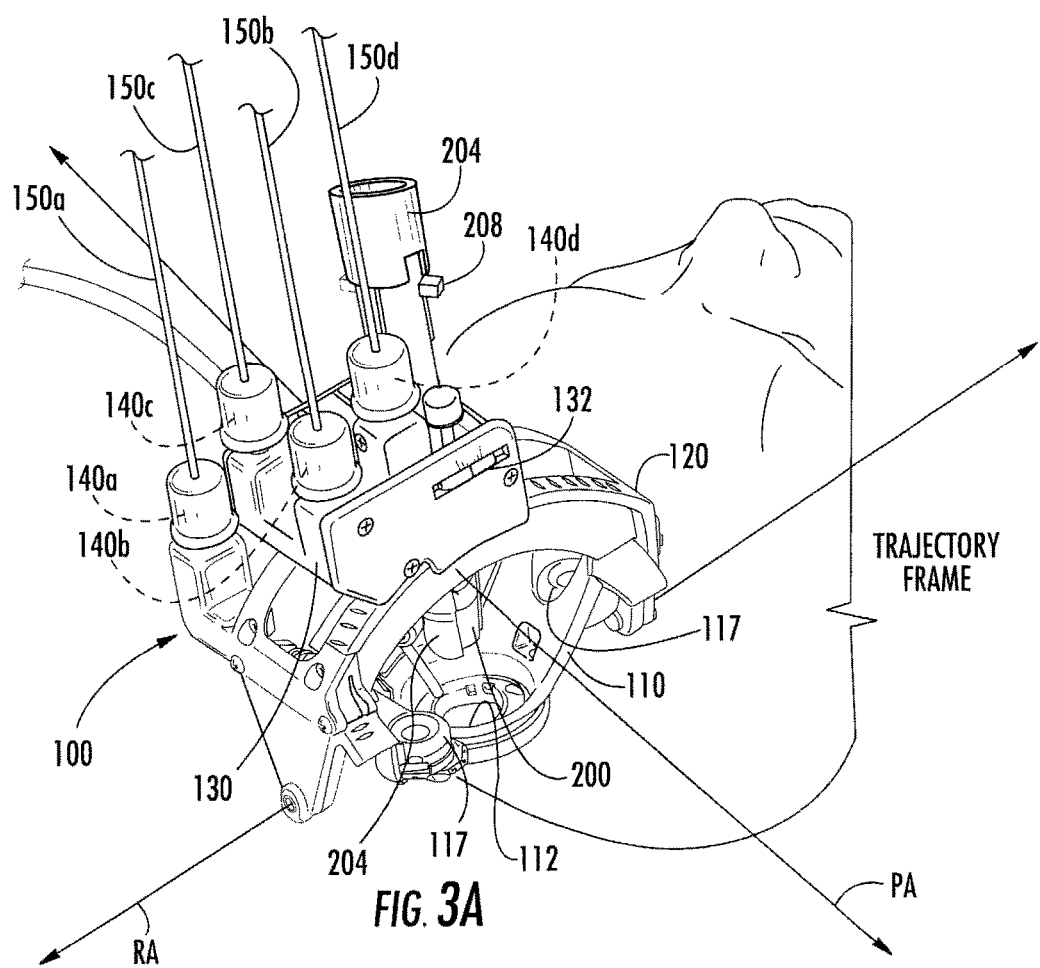
FIG. 3A is a top, side perspective view of a trajectory frame utilized in a MRI-guided interventional system, according to some embodiments of the present invention.

Referring to FIG. 3A, a trajectory frame 100 (which can also be described interchangeably as a "trajectory guide") is shown. The trajectory frame 100 may be configured to releasably hold a targeting cannula 200 as illustrated. The trajectory frame 100 includes a guide 204 (shown in partial view for ease of illustration), such as a support column, that removably receives the targeting cannula 200 (and/or other components) therein. The guide 204 (or guide/support column 1102 (e.g., FIG. 21 et seq.) can be secured to the X-Y support table 132 of the trajectory frame 100 (or 1100, FIG. 21, et seq.). The guide 204/1102 defines a Z-direction along its longitudinal axis relative to the X-Y plane of the X-Y support table 132. The trajectory frame 100 allows for the adjustability (typically at least two degrees of freedom, including rotational and translational) and/or calibration/fixation of the trajectory of a device held therein (e.g., as shown, in FIG. 3A, the targeting cannula 200 and/or probe or tool inserted through the targeting cannula 200).

Figure 8A:
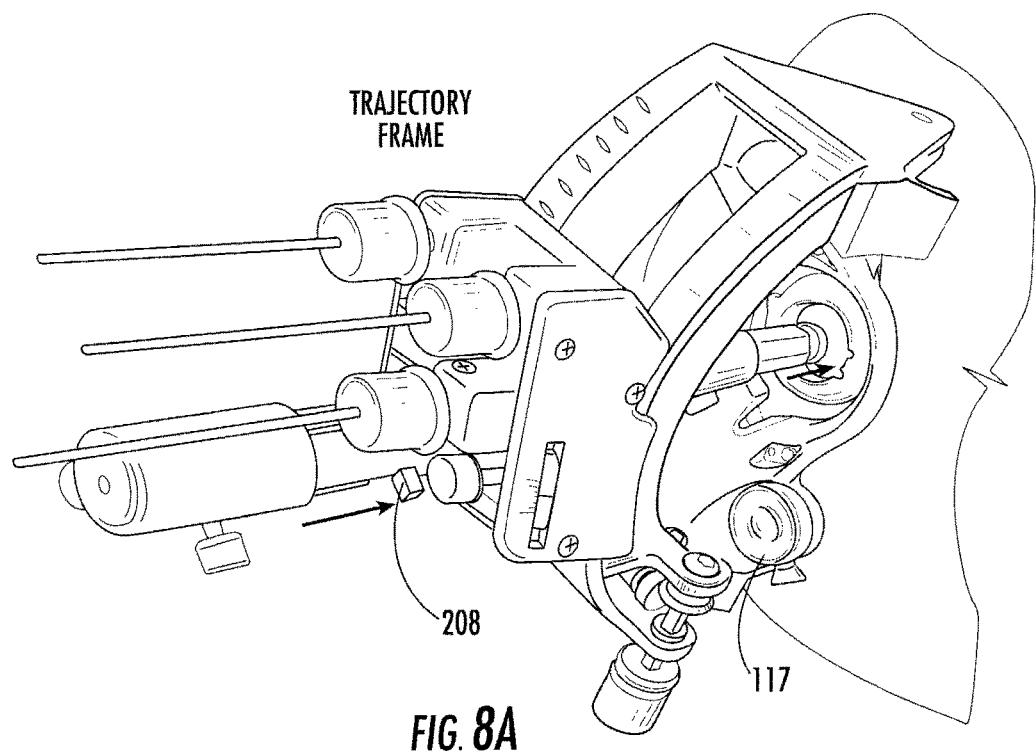
FIG. 8A is a perspective view of the trajectory frame of FIG. 3A secured to the body (e.g., skull) of a patient, and with the targeting cannula in an extended position.
Figure 8B:
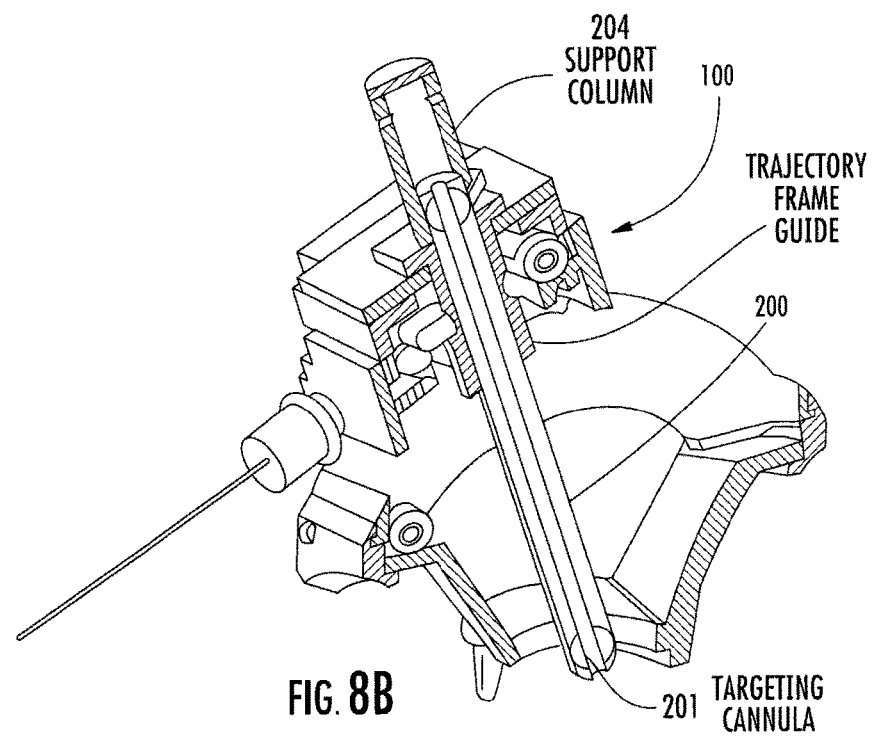
FIG. 8B is a cut-away perspective view of the trajectory frame of FIG. 3A, illustrating a guide with a targeting cannula therein according to some embodiments of the present invention.

For MRI-image guided versions of the system, the targeting cannula 200 can include an axially-extending guide bore 201 (FIG. 8B) therethrough that is configured to guide the desired therapeutic or diagnostic tool, e.g., intra-brain placement of a stimulation lead (or other type of device) in vivo, as will be described below. Intra-brain placement of devices may include chronically placed devices and acutely placed devices. Again, for MRI-image guided systems, the trajectory frame 100 may include fiducial markers 117 that can be detected in an MRI to facilitate registration of position in an image. For non-MRI uses, the MRI-type fiducial markers 117 are not required.

The illustrated trajectory frame 100 is configured to be mounted to a patient's skull around a burr hole ring (12, FIG. 1A) and over a burr hole (10, FIG. 1A), to provide a stable platform for advancing surgical devices, leads, etc. in the brain. The trajectory frame 100 includes a base 110, a yoke 120, a platform 130, and a plurality of actuators 140a-140d. The base 110 has a patient access aperture 112 formed therein, as illustrated. The base 110 is configured to be secured (directly or indirectly) to the skull of a patient such that the patient access aperture 112 overlies the burr hole 10 in the patient skull. The patient access aperture 112 can be centered over the burr hole 10 via the removable centering device 18.

The yoke 120 is movably mounted to the base 110 and is rotatable about a roll axis RA. A roll actuator 140a is operably connected to the yoke 120 and is configured to rotate the yoke 120 about the roll axis RA, as will be described in detail below. In some embodiments, the yoke 120 has a range of motion about the roll axis RA of about seventy degrees (70°). However, other ranges, greater and lesser than 70°, are possible, e.g., any suitable angle typically between about 10°-90°, 30°-90°, etc. The illustrated platform 130 is movably mounted to the yoke 120 and is rotatable about a pitch axis PA. A pitch actuator 140b is operably connected to the platform 130 and is configured to rotate the platform 130 about the pitch axis PA. In some embodiments, the platform 130 has a range of motion about the pitch axis PA of about seventy degrees (70°). However, other ranges, greater and lesser than 70°, are possible, e.g., any suitable angle typically between about 10°-90°, 30°-90°, etc.

The illustrated platform 130 includes an X-Y support table 132 that is movably mounted to the platform 130. The X-Y support table 132 is configured to move in an X-direction and Y-direction relative to the platform 130 and relative to a Z-direction defined by the longitudinal axis of the guide 204 and/or 1102. An X-direction actuator 140c is operably connected to the platform 130 and is configured to move the X-Y support table 132 in the X-direction. A Y-direction actuator 140d is operably connected to the platform 130 and is configured to move the X-Y support table 132 in the Y-direction. A pitch actuator 140b is operably connected to the platform 130 and is configured to rotate the platform 130 about the pitch axis PA.

The actuators 140a-140d are configured to translate and/or rotate portions of the trajectory frame 100. The targeting cannula 200 and/or tracking probe 1162/1194 (FIGS. 21, 31A) can be configured to translate in response to translational movement of the X-Y support table 132 and to rotate in response to rotational movement of the yoke 120 and platform 130 to define different axial intrabody trajectories extending through the patient access aperture 112 in the frame base 110.

The actuators 140a-140d may be manually-operated devices, such as thumbscrews, in some embodiments. The thumbscrews can be mounted on the frame 100 or may reside remotely from the frame 100. A user may turn the actuators 140a-140d by hand to adjust the position of the frame 100 and, thereby, a trajectory of the targeting cannula 200. In other embodiments, the actuators 140a-140d are operably connected to a remote control unit 400 (FIG. 1A) via a respective plurality of (optionally non-ferromagnetic when used for non-MRI systems), flexible drive shafts or control cables 150a-150d (FIG. 3A). The remote control unit 400 (FIG. 1A) includes a plurality of position controls, and each cable 150a-150d is operably connected to a respective position control and to a respective actuator 140a-140d. Movement of a position control operates a respective actuator 140a-140d via a respective control cable 150a-150d. The cables 150a-150d may extend a suitable distance (e.g., between about 1-4 feet, etc.) to allow a clinician to adjust the settings on the trajectory frame 100 without moving a patient and from a position outside the bore of a magnet (where a closed bore magnet type is used or where an MRI image guided system is used) associated with an MRI scanner.

Figures 3B, 3C:
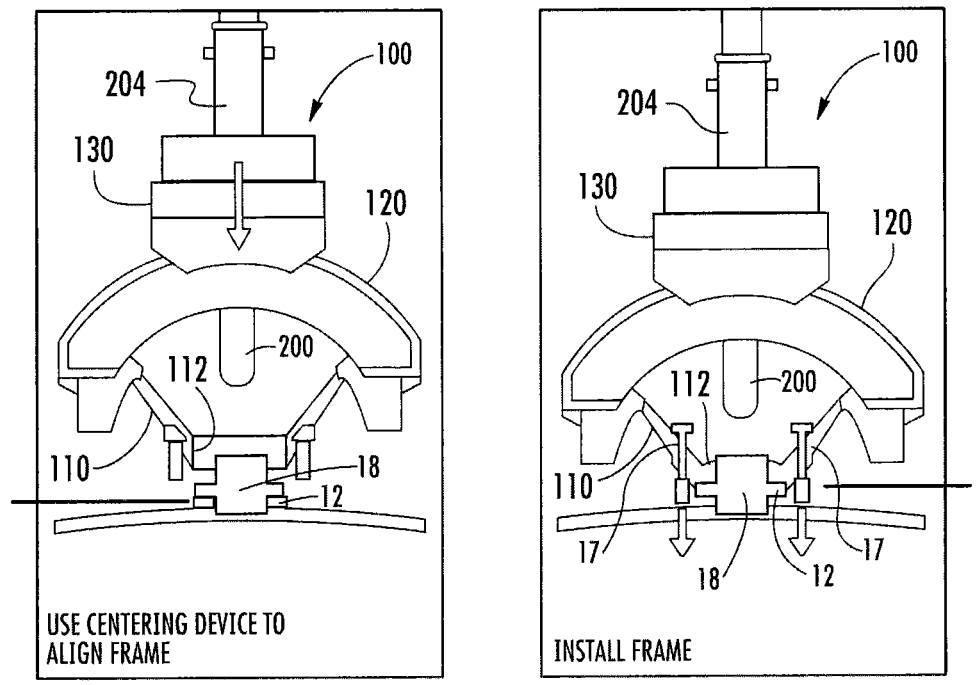
FIGS. 3B-3E are side view, schematic, sequential illustrations of a trajectory frame being secured to the skull of a patient.
Figure 3D:
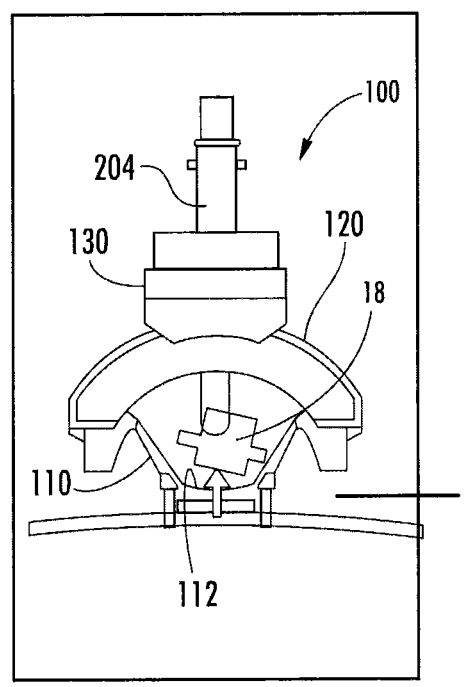
Figure 3E:
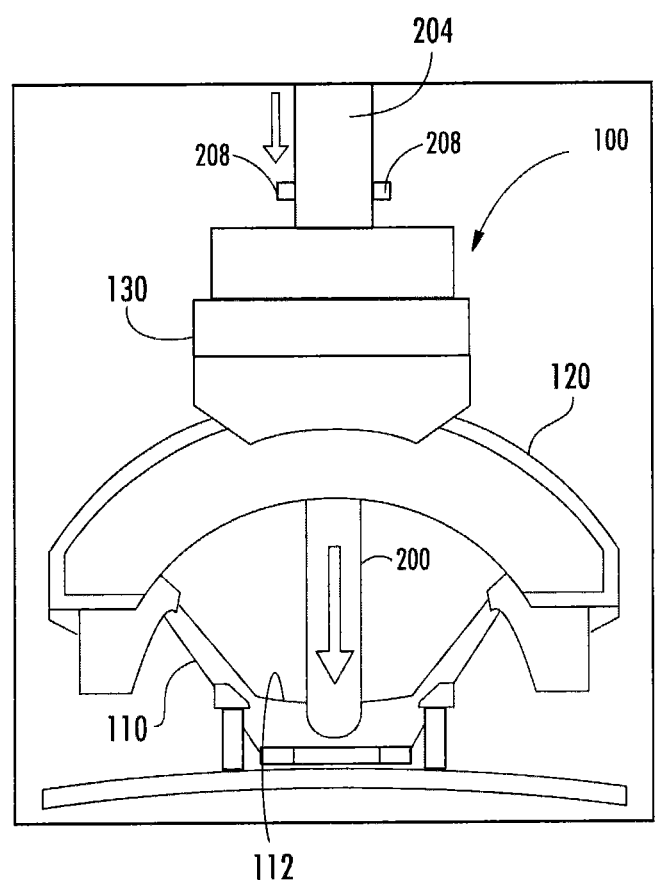
Figure 21:
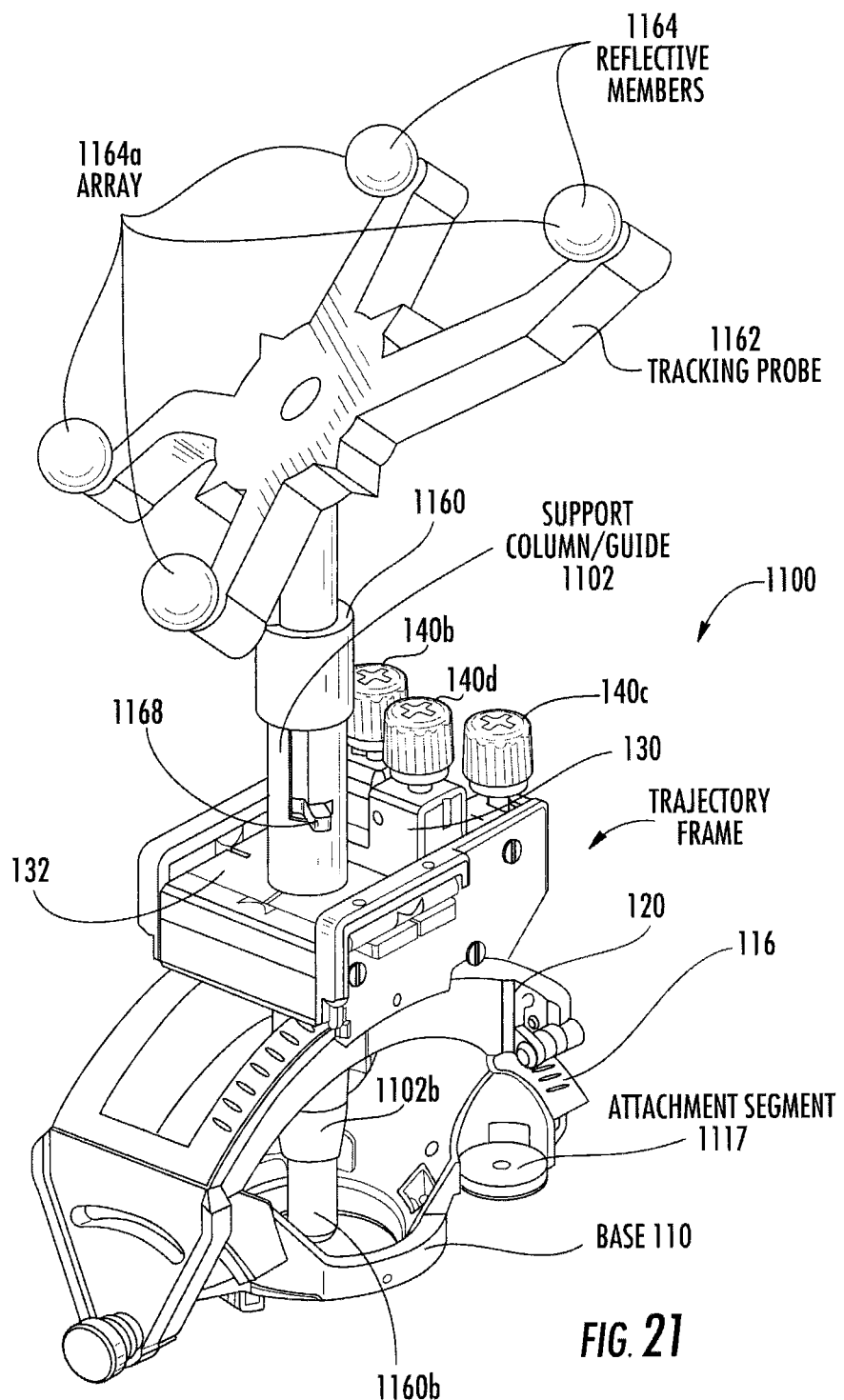
FIG. 21 is a side perspective view of a trajectory frame with an optical tracking probe according to embodiments of the present invention.

FIGS. 3B-3E are schematic side view sequential illustrations of the trajectory frame 100 being secured to the skull of a patient. FIG. 3B illustrates use of the centering device 18 to align the frame 100 relative to the burr hole 10. In FIG. 3C, the frame 100 is secured to the skull with fasteners and such that the patient access aperture 112 in the base 110 is centered around the centering device 18. In FIG. 3D, the yoke 120 is rotated out of the way such that the centering device 18 can be removed. In FIG. 3E, the targeting cannula 200 is moved to an extended position and locked in the extended position via prongs 208 that engage slots 1103 in the guide 204. FIG. 21 illustrates a similar extended configuration for the tracking probe 1160 for image guided systems that are not required to use (and typically do not use) the targeting cannula 200.

Figure 6:
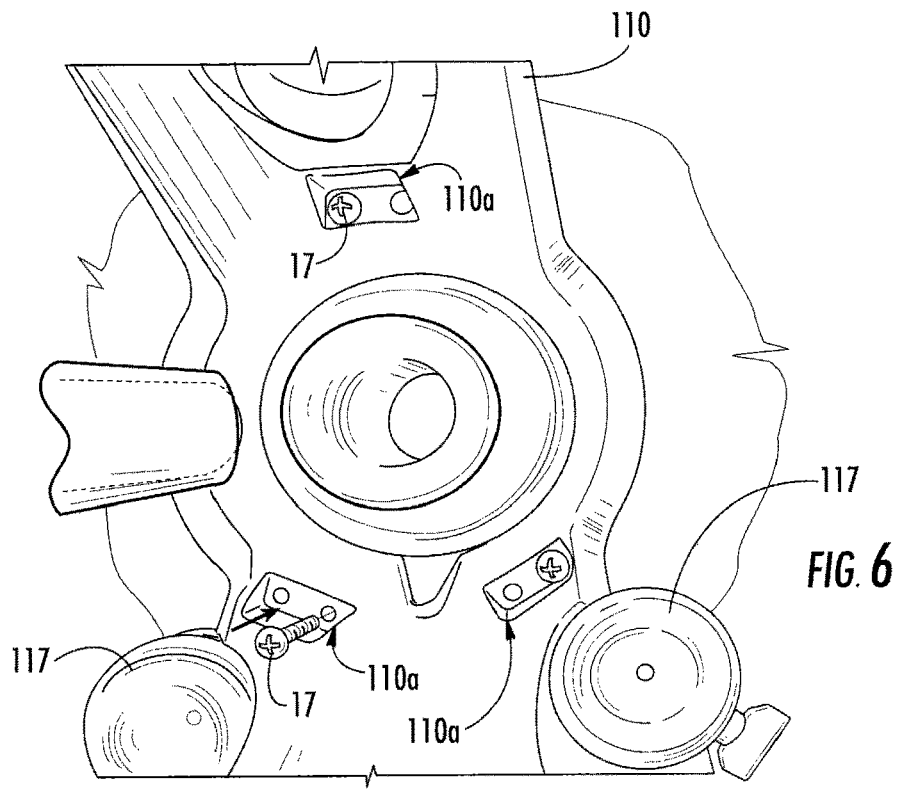
FIG. 6 illustrates the base of the trajectory frame of FIG. 3A secured to the skull of a patient.
Figure 7:
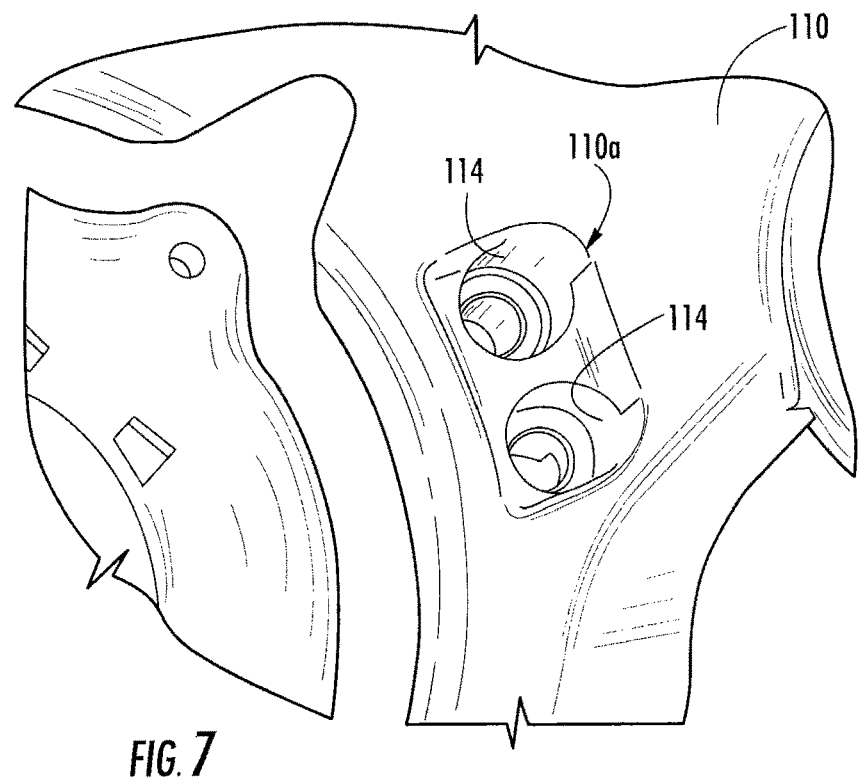
FIG. 7 is an enlarged partial perspective view of the base of the trajectory frame of FIG. 3A illustrating an attachment location with a pair of adjacent apertures for receiving fasteners therethrough, according to some embodiments of the present invention.

Referring to FIGS. 6-7, the base 110 includes a plurality of locations 110a for attaching the base 110 to a skull of a patient via fasteners 17. Each location 110a may include two or more adjacent apertures 114. Each aperture 114 is configured to receive a fastener 17 (e.g., a screw, rod, pin, etc.) therethrough that is configured to secure the base 110 to the skull of a patient. The base can be a scalp mount or skull mount type base 110.

The base 110 can includes MRI-visible fiducial markers 117 that allow the location/orientation of the trajectory frame 100 to be determined within an MRI image during an MRI-guided procedure. In the illustrated embodiment, the fiducial markers 117 have a torus or "doughnut" shape and are spaced apart. However, fiducial markers having various shapes and positioned at various locations on the trajectory frame 100 may be utilized. For non-MRI uses, the fiducials 117 can be omitted.

Figure 4:
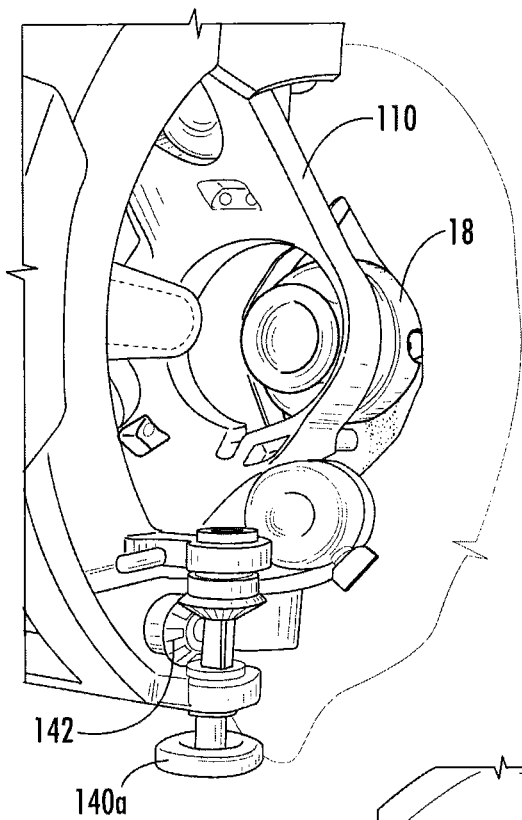
FIGS. 4-5 are partial top perspective views of the trajectory frame of FIG. 3A illustrating the base of the trajectory frame being positioned on the skull of a patient with the centering device of FIG. 2B extending through the patient access aperture.
Figure 5:
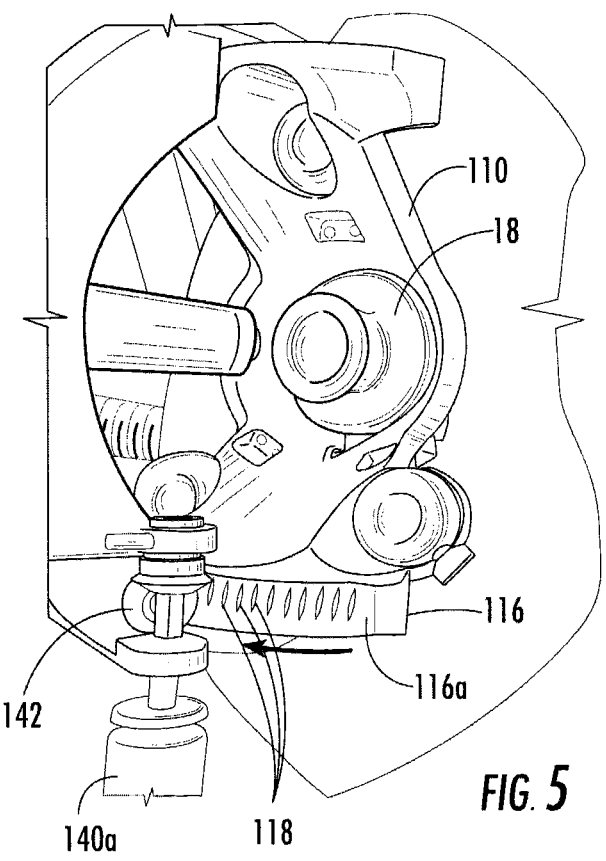
Figure 9:
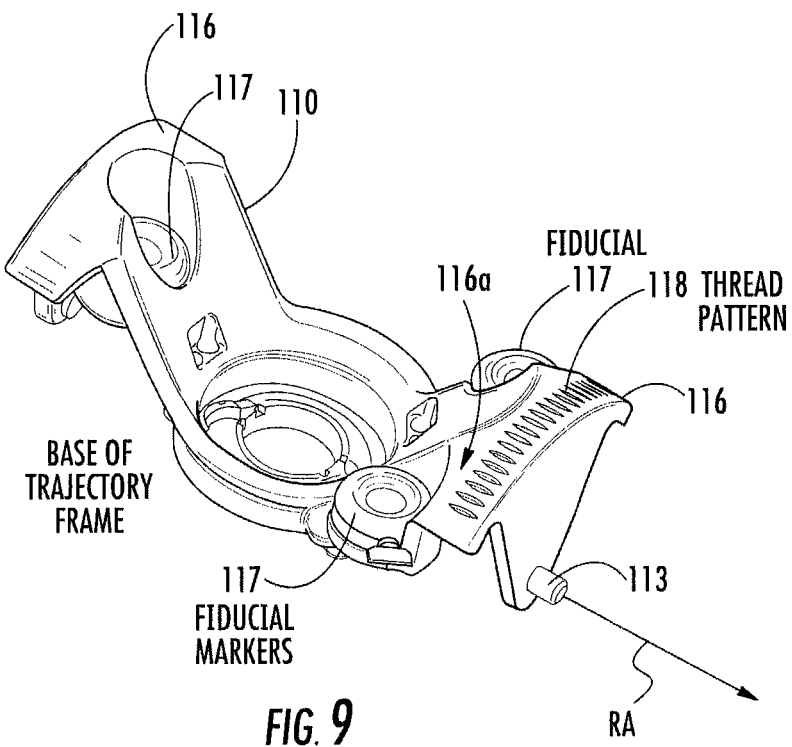
FIG. 9 is a perspective view of the base of the trajectory frame of FIG. 3A illustrating fiducial markers associated therewith and illustrating an arcuate arm with a thread pattern formed in a surface thereof that is configured to be engaged by a roll axis actuator, according to some embodiments of the present invention.

The base 110 also includes a pair of spaced apart arcuate arms 116, as illustrated in FIG. 9. The yoke 120 (FIG. 3A) is pivotally attached to pivot points 113 (FIG. 9) for rotation about the roll axis RA. The yoke 120 engages and moves along the base arcuate arms 116 when rotated about the roll axis RA. In the illustrated embodiment, one of the base arcuate arms 116 includes a thread pattern 118 formed in (e.g., embossed within, machined within, etc.) a surface 116a thereof. However, in other embodiments, both arms 116 may include respective thread patterns. The roll actuator 140a includes a rotatable worm 142 with teeth that are configured to engage the thread pattern 118, as illustrated in FIG. 5. As the worm 142 is rotated, the teeth travel along the thread pattern 118 in the arcuate arm surface 116a. Because the base 110 is fixed to a patient's skull, rotation of the roll actuator worm 142 causes the yoke 120 to rotate about the roll axis RA relative to the fixed base 110. Rotation about roll axis RA is illustrated in FIGS. 4-5. For example, in FIG. 5, the yoke 120 is rotated about the roll axis RA sufficiently to allow access to and removal of the optional centering device 18.

Figure 10:
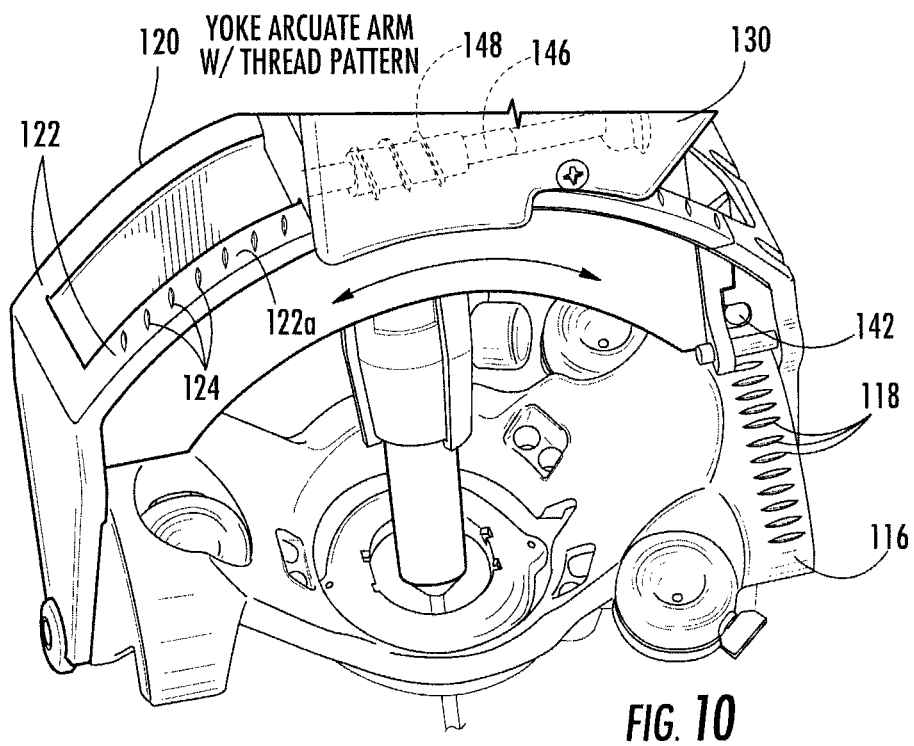
FIG. 10 is a partial perspective view of the trajectory frame of FIG. 3A illustrating a yoke arcuate arm with a thread pattern formed in a surface thereof that is configured to be engaged by a pitch axis actuator, according to some embodiments of the present invention.

Referring to FIG. 10, the yoke 120 includes a pair of spaced apart upwardly extending, arcuate arms 122. The platform 130 engages and moves along the yoke arcuate arms 122 when rotated about the pitch axis PA. In the illustrated embodiment, one of the yoke arcuate arms 122 includes a thread pattern 124 formed in (e.g., embossed within, machined within, etc.) a surface 122a thereof. However, in other embodiments, both arms 122 may include respective thread patterns. The pitch actuator 140b includes a rotatable worm 146 with teeth 148 that are configured to engage the thread pattern 124. As the worm 146 is rotated, the teeth 148 travel along the thread pattern 124 in the arcuate arm surface 122a. Because the base 110 is fixed to a patient's skull, rotation of the pitch actuator worm 146 causes the platform 130 to rotate about the pitch axis PA relative to the fixed base 110.

As illustrated in FIG. 3A, the roll actuator 140a, pitch actuator 140b, X-direction actuator 140c, and Y-direction actuator 140d each extend outwardly from the frame 100 along substantially the same direction (e.g., upwardly from the platform 130). This configuration facilitates easy connection of the control cables 150a-150d to the actuators 140a-140d (where used) and also facilitates bundling of the cables 150a-150d to reduce clutter or provide ease of handling and set-up. Embodiments of the present invention are not limited to the orientation/arrangement of the actuators 140a-140d and cables 150a-150d, however. The actuators 140a-140d may extend in various directions and these directions may be different from each other. In addition, the actuators 140a-140d may extend along the same direction from the frame, but in a different direction than that illustrated in FIG. 3A.

Operations associated with a typical MRI-image guided surgical procedure using the trajectory frame 100, according to some embodiments of the present invention, will now be described. These operations relate to deep brain stimulation procedures. Embodiments of the present invention are not limited to use with deep brain stimulation procedures, however, nor are the devices limited to MRI-image guided procedures.

Initially, a patient is placed within an MR scanner and MR images are obtained of the patient's head that visualize the patient's skull, brain, fiducial markers and ROI (region of interest or target therapeutic site). The MR images can include volumetric high-resolution images of the brain. To identify the target ROI, certain known anatomical landmarks can be used, i.e., reference to the AC, PC and MCP points (brain atlases give the location of different anatomies in the brain with respect to these points) and other anatomical landmarks. The location of a burr hole 10 (FIG. 2A) may optionally be determined manually by placing fiducial markers on the surface of the head or programmatically by projecting the location in an image.

Images in the planned plane of trajectory are obtained to confirm that the trajectory is viable, i.e., that no complications with anatomically sensitive areas should occur. The patient's skull is optically or manually marked in one or more desired locations to drill the burr hole. The burr hole 10 is drilled and a burr hole ring 12 is affixed to the skull overlying the burr hole.

The trajectory frame 100 is then fixed to the skull of the patient and the targeting cannula 200 is properly fitted thereto. A localization scan can be obtained to determine/register the location of the targeting cannula 200, in direct orientation of the trajectory frame 100. The settings to which the trajectory frame 100 should be adjusted are electronically determined so that the targeting cannula 200 is in the desired trajectory plane. Frame adjustment calculations are provided to a clinician who can manually or electronically adjust the orientation of the trajectory frame 100. The desired trajectory plane is confirmed by imaging in one or more planes orthogonal to the desired trajectory plane.

Once the targeting cannula 200 has the desired trajectory plane, a multipurpose probe (not shown) and delivery sheath (not shown) can be advanced through the targeting cannula 200. The advancement of the probe can be monitored by imaging to verify that the probe will reach the target accurately. If the probe and delivery sheath are at the desired target, the sheath is left in place and the probe is removed. The sheath can now act as the delivery cannula for an implantable lead (not shown).

If the probe and delivery sheath are not at the desired/optimal location, a decision is made as to where the probe and delivery sheath need to be. The trajectory frame 100 is adjusted accordingly via the actuators 140a-140d and the probe and delivery sheath are re-advanced into the brain. Once the probe and delivery sheath are at the desired location, the probe is removed and the delivery sheath is left in place. A lead is then advanced to the target location using the sheath as a guide. The location of the lead is confirmed by reviewing an image, acoustic recording and/or stimulation. The sheath is then removed, leaving the lead in place.

It is contemplated that embodiments of the invention can provide an integrated system 50 that may allow the physician to place the interventional device/leads accurately and in short duration of time. In some embodiments, once the burr hole is drilled, and the trajectory frame is fixed to the skull; the trajectory frame is oriented such that the interventional device advanced using the trajectory frame follows the desired trajectory and reaches the target as planned in preoperative setup imaging plans. As described herein, the system 50 can employ hardware and software components to facilitate an automated or semiautomated operation to carry out this objective.

Referring now to FIGS. 13-19, a trajectory frame 1100, according to embodiments of the present invention, is illustrated. The trajectory frame 1100 is similar to the trajectory frame 100 described above with respect to FIGS. 1A-12, but is configured to removably receive a devices of various sizes and configurations within a support column or guide 1102 (similar to guide 204), as described below. The illustrated trajectory frame 1100 is configured to be mounted to a patient's skull around a burr hole ring (12, FIG. 1) and over a burr hole (10, FIG. 1), to provide a stable platform for advancing surgical devices, leads, etc., in the brain, as described above. However, a trajectory frame 1100 according to embodiments of the present invention can be configured to be mounted to various portions of the body of a patient.

Again, as for the similar trajectory frame 100 described above, the illustrated trajectory frame 1100 includes a base 110, a yoke, 120, a platform 130, and a plurality of actuators 140*a*-140*d*. The base 110 has a patient access aperture 112 formed therein, as illustrated. The base 110 is configured to be secured (directly or indirectly) to the skull or scalp of a patient such that the patient access aperture 112 overlies the burr hole 10 in the patient skull. The base 110 can include a plurality of narrow, tapered members 19 that can be driven into the skull of a patient to prevent the base 110 from moving. Fasteners 17, such as screws, can then used to secure the base to the skull of the patient, as described above.

The patient access aperture 112 is configured to be centered over a burr hole 10 optionally via a removable centering device 18, as described above. The yoke 120 is movably mounted to the base 110 and is rotatable about a roll axis RA, as described above. The platform 130 is movably mounted to the yoke 120 and is rotatable about a pitch axis PA, as described above.

The illustrated platform 130 includes an X-Y support table 132 that is movably mounted to the platform 130. The X-Y support table 132 is configured to move in an X-direction and Y-direction relative to the platform 130 and to a Z-direction defined by the longitudinal axis of the guide 1102. An X-direction actuator 140*c* is operably connected to the platform 130 and is configured to move the X-Y support table 132 in the X-direction. A Y-direction actuator 140*d* is operably connected to the platform 130 and is configured to move the X-Y support table 132 in the Y-direction. A pitch actuator 140*b* is operably connected to the platform 130 and is configured to rotate the platform 130 about the pitch axis PA.

The actuators 140*a*-140*d* are configured to translate and/or rotate the frame. When inserted within the guide 1102, the targeting cannula 200, tracking probe 1160 or 1190 (FIG. 21, 31A) and other devices inserted within the guide 1102, are configured to translate in response to translational movement of the X-Y support table 132 and to rotate in response to rotational movement of the yoke 120 and platform 130 to define different axial intrabody trajectories extending through the patient access aperture 112 in the frame base 110.

The trajectory frame guide 1102 is configured to removably receive various probes and/or tools, as described below. For example, the guide 1102 may have a larger diameter than conventional targeting cannula guides which, thereby allows for various devices to be utilized with the frame 1100 that otherwise would not be able to do so.

In addition, guides 1102 having different size internal diameters may be provided for receiving various devices of different sizes or a single guide 1102 can be integral to the frame 1100 and configured to receive different tools having different diameters. If the former, for example, a guide 1102 may have an internal diameter sized to receive a particular device therein. Another guide 1102 may have a larger or smaller internal diameter also sized to receive a particular device therein. To facilitate replacing one size guide 1102 with another, each guide 1102 may be removably and interchangeable secured to the X-Y support table 132. For example, each guide may be threadingly secured to the X-Y support table 132. However, other means for removably securing a guide 1102 to the X-Y support table 132 can be utilized.

The trajectory frame 1100 allows for the adjustability (typically at least two degrees of freedom, including rotational and translational) and calibration/fixation of the trajectory of at least one of, and typically all of, a targeting cannula 200, and a tracking probe 1160, 1190 (FIG. 21, 31A) and/or other probe or tool inserted through the or a respective guide 1102.

The removable targeting cannula 200 has a proximal end portion 200*a*, an opposite distal end portion 200*b*, and an axially-extending guide bore 201 extending from the proximal end portion 200*a* to the distal end portion 200*b* that is configured to guide a therapeutic or diagnostic tool, e.g., intra-brain placement of a stimulation lead (or other type of device) in vivo. Intra-brain placement of devices may include chronically placed devices and acutely placed devices. The trajectory frame 1100 may optionally include fiducial markers 117 (MRI detectable fiducials when used for MRI-image guided systems) that can be detected in an MRI to facilitate registration of position in an image. Lugs 208 extend outwardly from the proximal end portion 200*a* of the targeting cannula 200. These lugs 208 are configured to removably secure the targeting cannula 200 to the guide 1102. Other cooperating devices for the trajectory frame 1100 may also have lugs, e.g., 1168 (FIG. 21, 23A-C), 1178 (FIGS. 29A-C) and 1198 (FIGS. 31A-C), for attachment to the guide 1102 or an interchangeable respective guide 1102 held by the platform 130, and are not required to be MRI-compatible as they may be used for non-MRI surgical image/camera tracking and/or guided systems.

The guide 1102 has opposite proximal and distal end portions 1102*a*, 1102*b*. In some embodiments, the proximal end portion 1102*a* contains threads 1104, as illustrated. These threads 1104 can be molded or machined into the guide 1102, as would be understood by those skilled in the art of the present invention.

Figure 14:
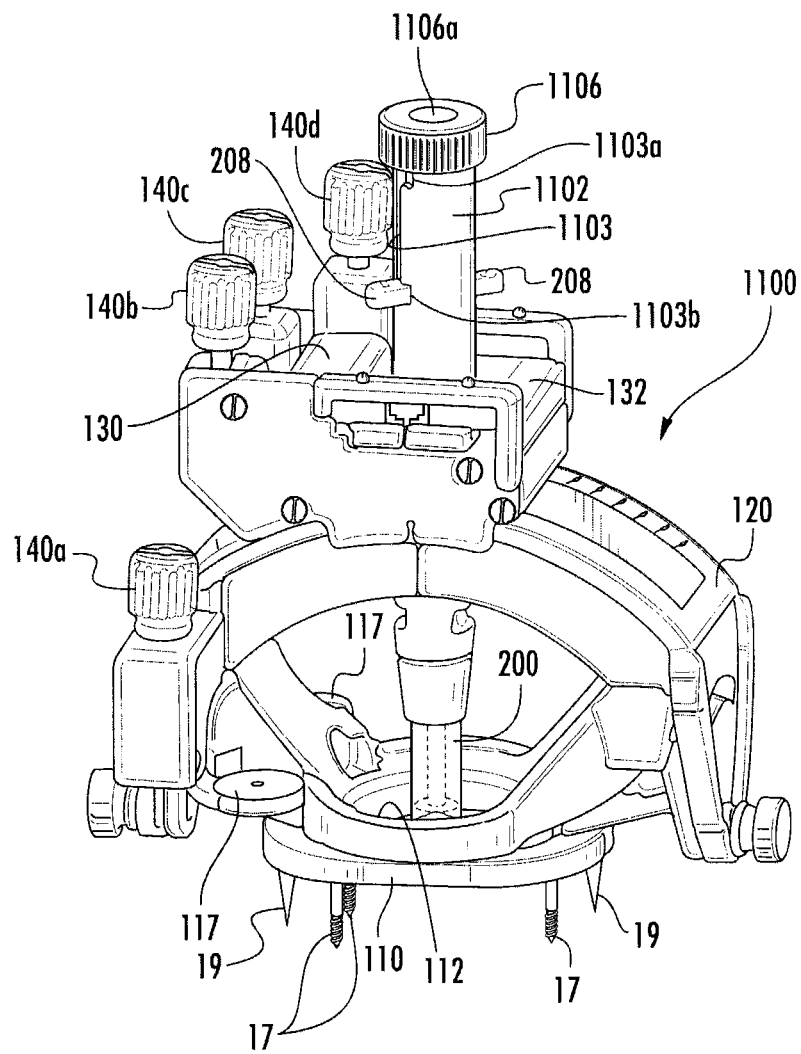
FIG. 14 illustrates the targeting cannula of FIG. 13 inserted within the guide and the cap removably secured to the guide proximal end portion.

The threads 1104 can be configured to threadingly engage a correspondingly threaded cap 1106 to secure a targeting cannula 200 and other devices within the guide 1102, and to allow for quick removal. FIG. 14 illustrates the targeting cannula 200 within the guide 1102 and the cap 1106 threadingly secured to the threads 1104 of the guide proximal end portion 1102*a*. The illustrated cap 1106 includes an opening 1106*a* to facilitate insertion of a probe or other device into and through the lumen 201 of the targeting cannula 200.

In other embodiments, the guide proximal end portion 1102*a* may include a detent (not shown) or similar structure formed therein and the cap 1106 may include a protrusion (not shown) configured to engage the detent so as to removably secure the cap 1106 and targeting cannula 200 to the guide 1102 (i.e., create a "snap fit") and to allow for quick removal. Alternatively, the guide proximal end portion 1102a may include a protrusion extending therefrom and the cap 1106 may include a detent formed therein that is configured to engage the protrusion so as to removably secure the cap and targeting cannula 200 to the guide 1102. In addition, various other ways of causing frictional engagement (e.g., an interference fit) may be utilized for removably securing the cap 1106 and targeting cannula 200 to the guide 1102 and to allow for quick removal, without limitation. Various shapes and/or components that allow for quick removal may be utilized, without limitation.

In some embodiments, the targeting cannula 200 and cap 1106 can be a preassembled unit.

The guide 1102 includes downwardly extending slots 1103, shown as a pair of opposing slots 1103, formed in the proximal end portion 1102a, thereof, as illustrated. Each slot 1103 includes an upper ledge portion 1103a and a lower ledge portion 1103b that are configured to engage the targeting cannula lugs 208. The lugs 208 cooperate with the slots 1103 to allow the targeting cannula 200 to be inserted within the guide 1102. By rotating the targeting cannula 200 such that the lugs 208 cooperate with the upper ledge portions 1103a, the targeting cannula 200 can be positioned at a first or upper position. By inserting the targeting cannula 200 further within the guide 1102 and then rotating the targeting cannula 200 such that the lugs 208 cooperate with the lower ledge portions 1103a, the targeting cannula 200 can be securely held at a second or lower position.

Typically after the trajectory frame 1100 is aligned, a center punch (not shown) can be placed down the targeting cannula lumen 201 and pushed or tapped into the skull of a patient. This will create an incision in the scalp and provide a starting point for a drill bit. Alternately, an incision can be made in a patient's scalp first. In some instances, a center punch may not be required.

Figure 13:
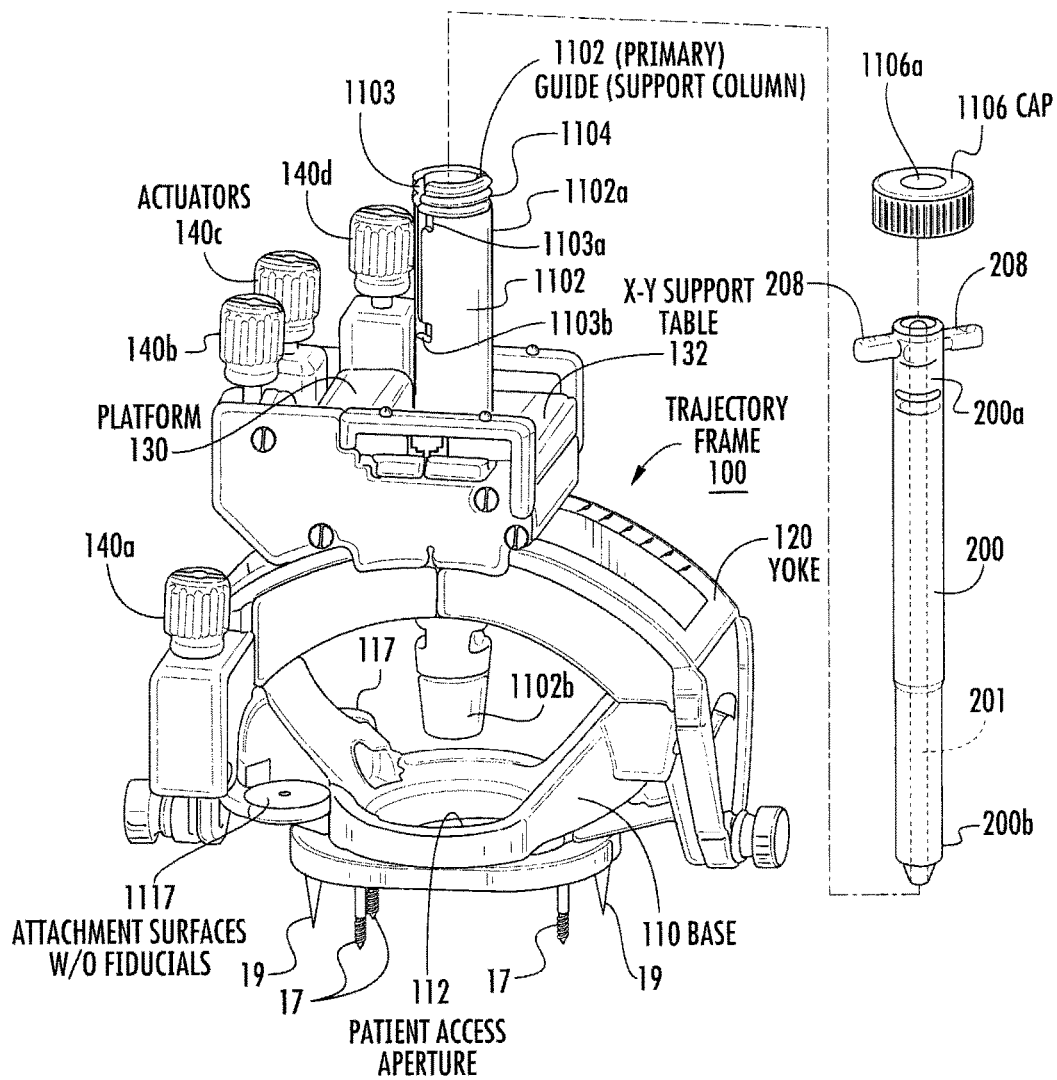
FIG. 13 is a partial exploded perspective view of a trajectory frame utilized in an MRI-guided interventional system, according to some embodiments of the present invention, wherein a guide includes a threaded proximal end portion for removably retaining a cap thereon that is configured to cover a targeting cannula and other devices inserted within the guide.
Figure 15A:
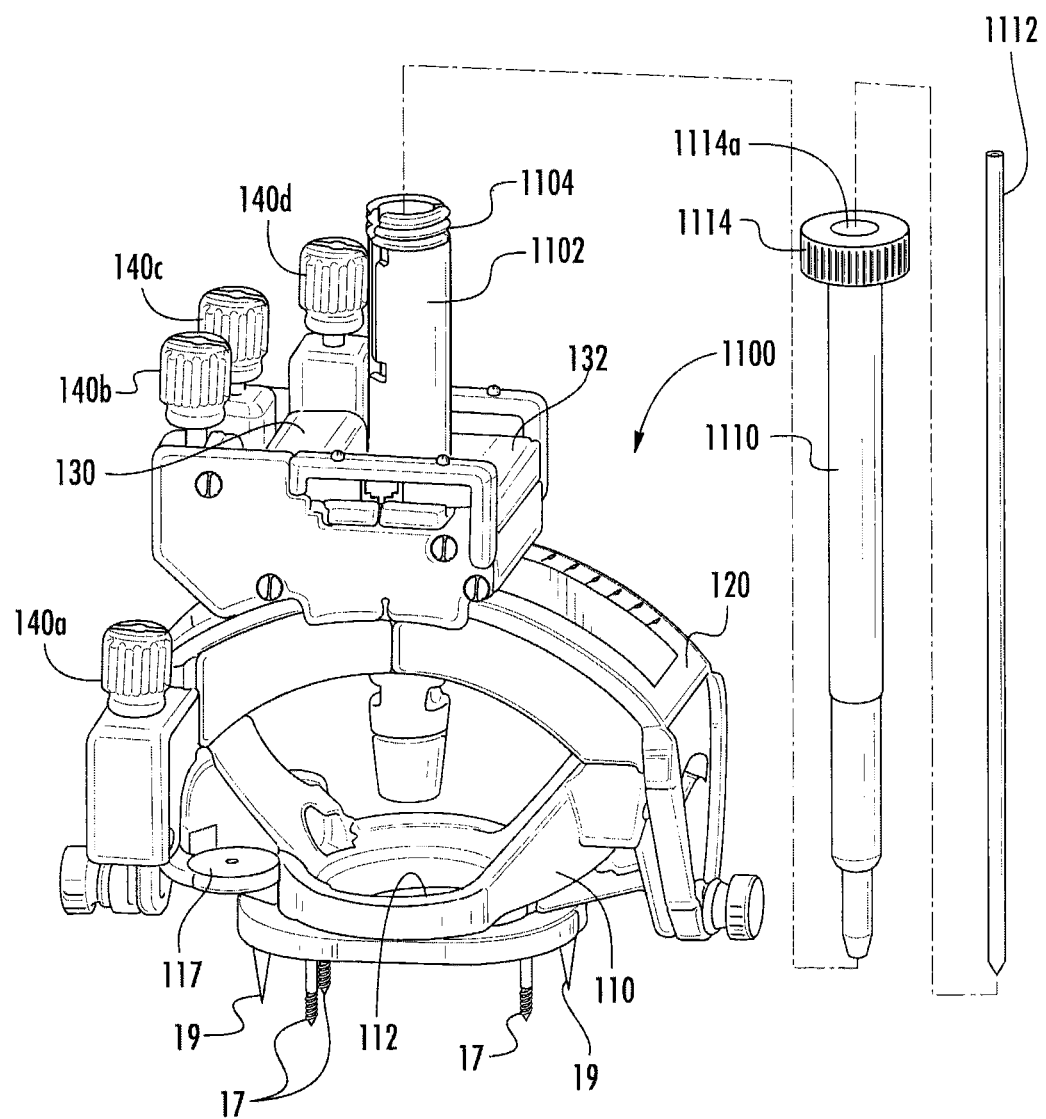
FIG. 15A is a partial exploded perspective view of a trajectory frame utilized in an MRI-guided interventional system, according to some embodiments of the present invention, wherein a guide includes a threaded proximal end portion for removably retaining a drill guide inserted within the guide.
Figure 15B:
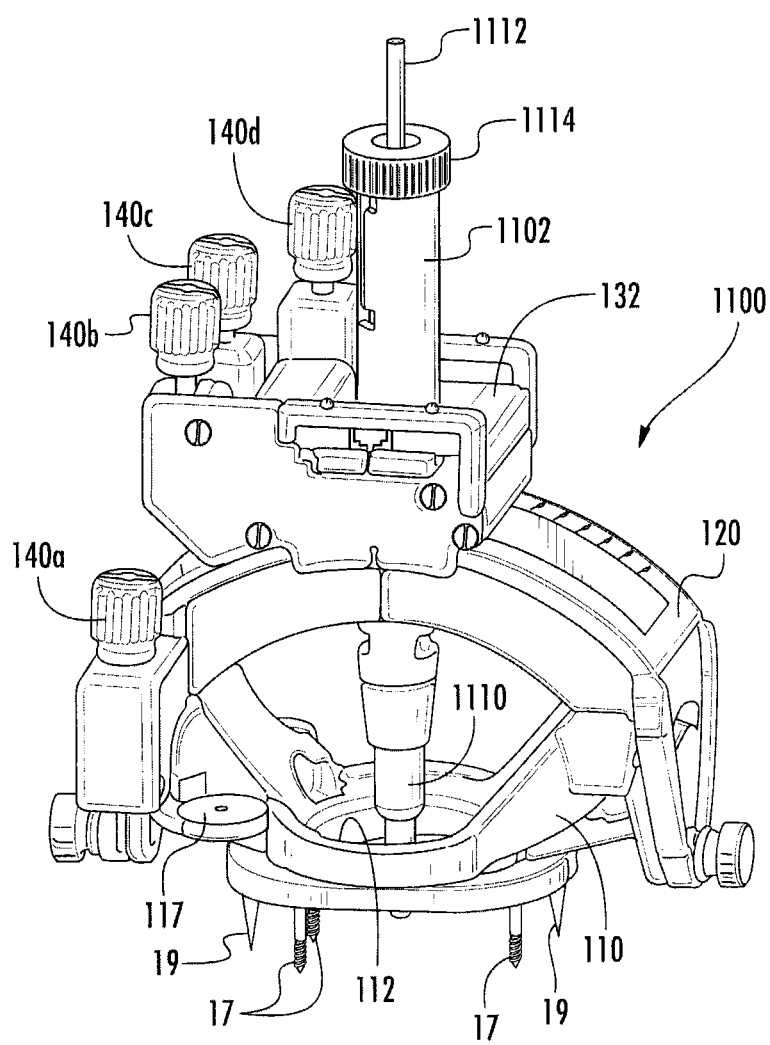
FIG. 15B illustrates the drill guide of FIG. 15A inserted within the guide and the threaded end of the drill guide threadingly secured to the threaded proximal end portion of the guide.

FIG. 15A illustrates the trajectory frame 1100 of FIG. 13 with the targeting cannula 200 removed from the guide 1102 and wherein the guide 1102 is configured to removably receive a drill guide 1110 and long drill bit 1112 inserted therewithin. FIG. 15B illustrates the drill guide 1110 of FIG. 15A inserted within the guide 1102 and a threaded cap 1114, having an opening 1114a, of the drill guide threadingly secured to the threads 1104 at the proximal end portion 1102a of the guide 1102. Alternatively, the cap 1114 of the drill guide may be attached to the guide proximal end 1102a via a detent or other similar structure, as described above. Once a hole is drilled in the skull of a patient via the drill bit 1112, the drill bit 1112 and drill guide 1110 are removed. Note that a drill guide 1110 and drill bit 1112 may not be required if an access (burr) hole is already made within the skull.

Figure 16A:
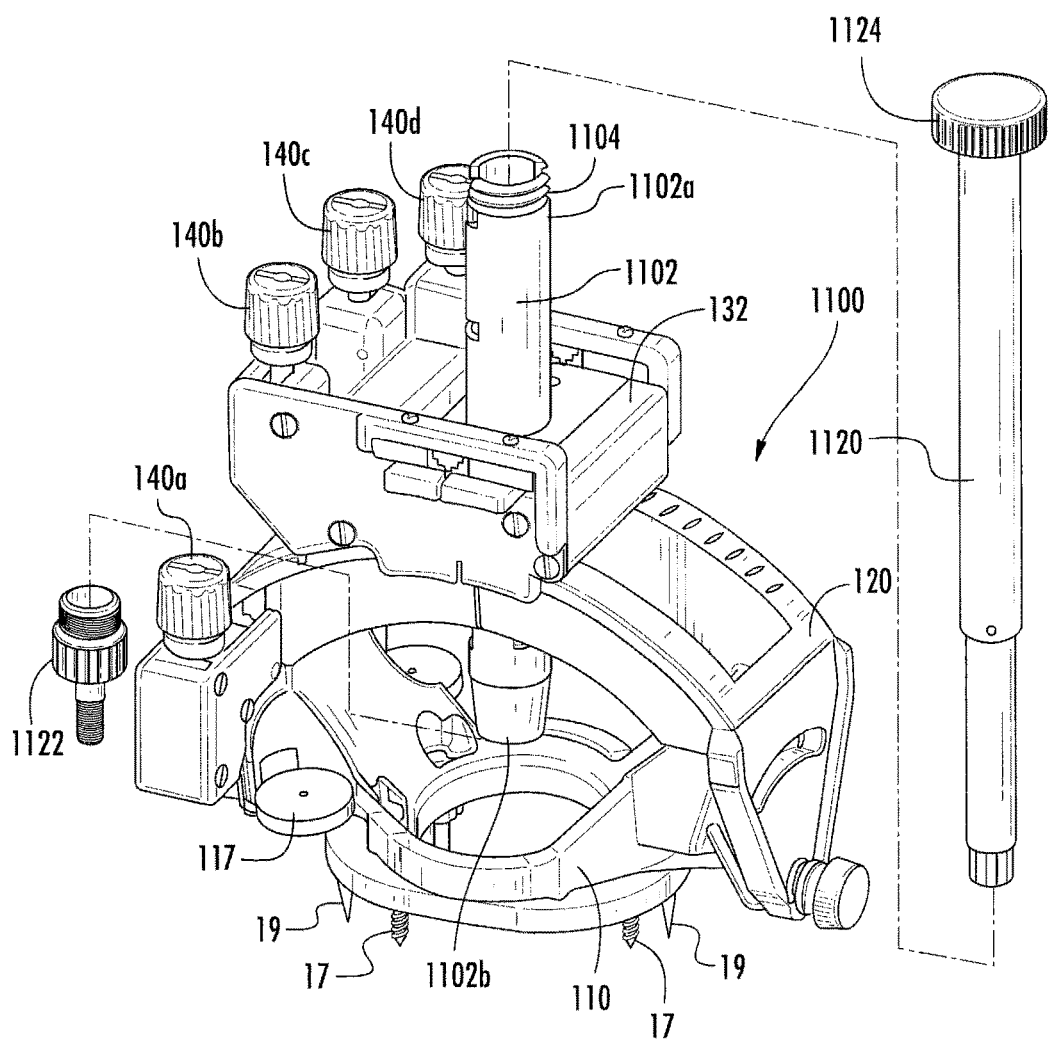
FIG. 16A is a partial exploded perspective view of a trajectory frame utilized in an MRI-guided interventional system, according to some embodiments of the present invention, and configured to removably receive a skull fixation device driver within the guide and a skull fixation device at the guide distal end.
Figure 16B:
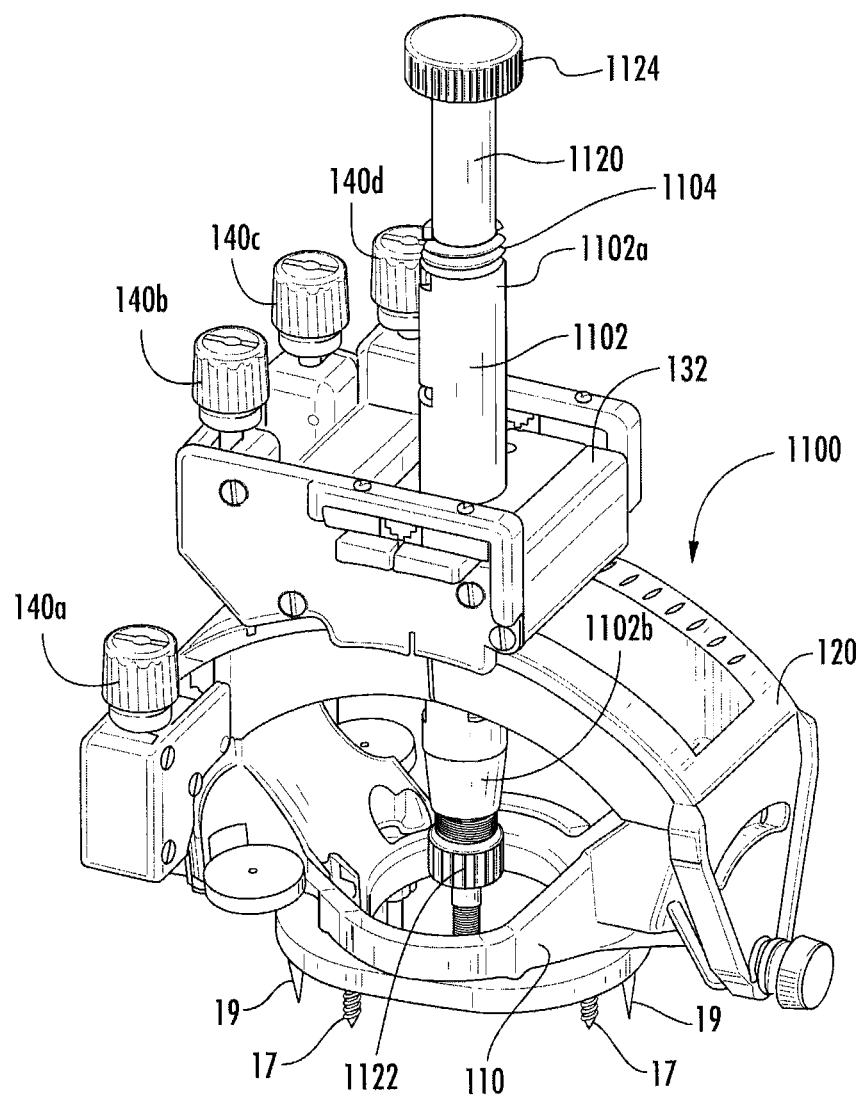
FIG. 16B illustrates the skull fixation device driver inserted within the guide via the proximal end portion thereof and the skull fixation device removably secured to the guide distal end.
Figure 17:
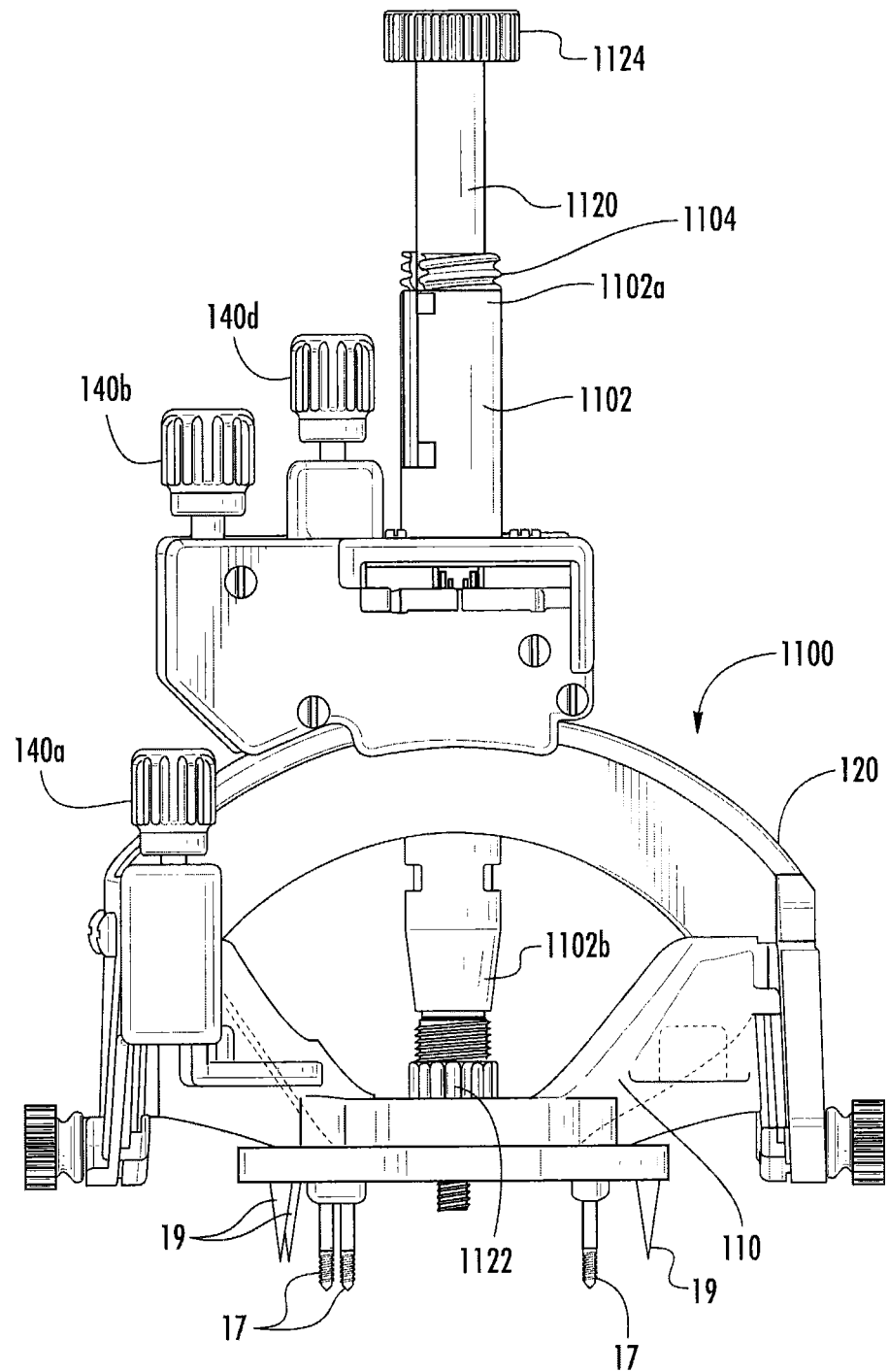
FIG. 17 is a side view of the trajectory frame of FIG. 16B.

FIGS. 16A-16B and 17 illustrate the trajectory frame 1100 of FIG. 13 with the targeting cannula 200 removed from the guide 1102 and wherein the guide 1102 is configured to removably receive a skull fixation device driver 1120 inserted through the proximal end portion 1102a thereof. A skull fixation device 1122 is inserted in the guide distal end 1102b. The skull fixation device 1122 and the skull fixation device driver 1120 are configured to be engaged such that the skull fixation device 1122 can be screwed into the skull of a patient by rotating and advancing the skull fixation device driver 1120 from the proximal end 1102a of the guide 1102. The illustrated skull fixation device driver 1120 is provided with a knob or handle 1124 that facilitates rotation of the skull fixation device driver 1120 by hand.

Figure 18A:
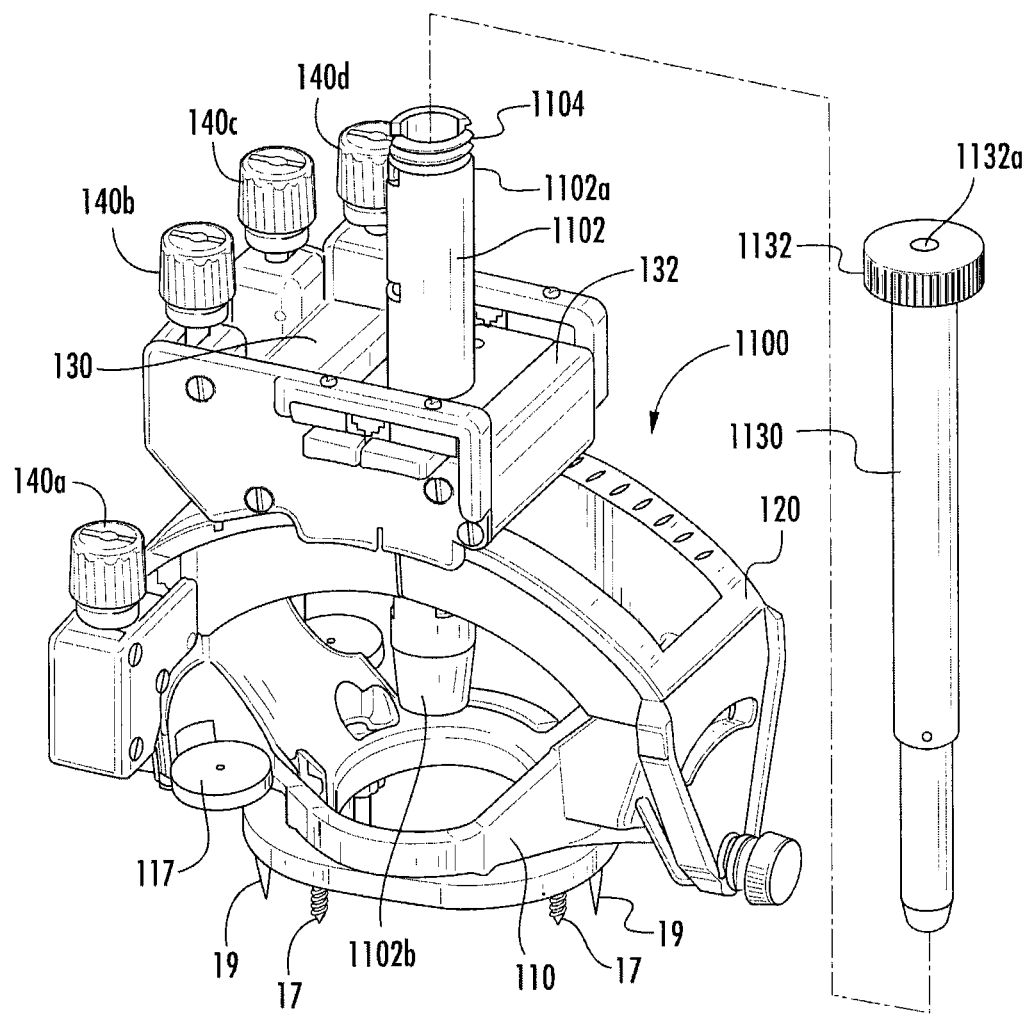
FIG. 18A is a partial exploded perspective view of a trajectory frame utilized in an MRI-guided interventional system, according to some embodiments of the present invention, and configured to removably receive a catheter guide within the guide.
Figure 18B:
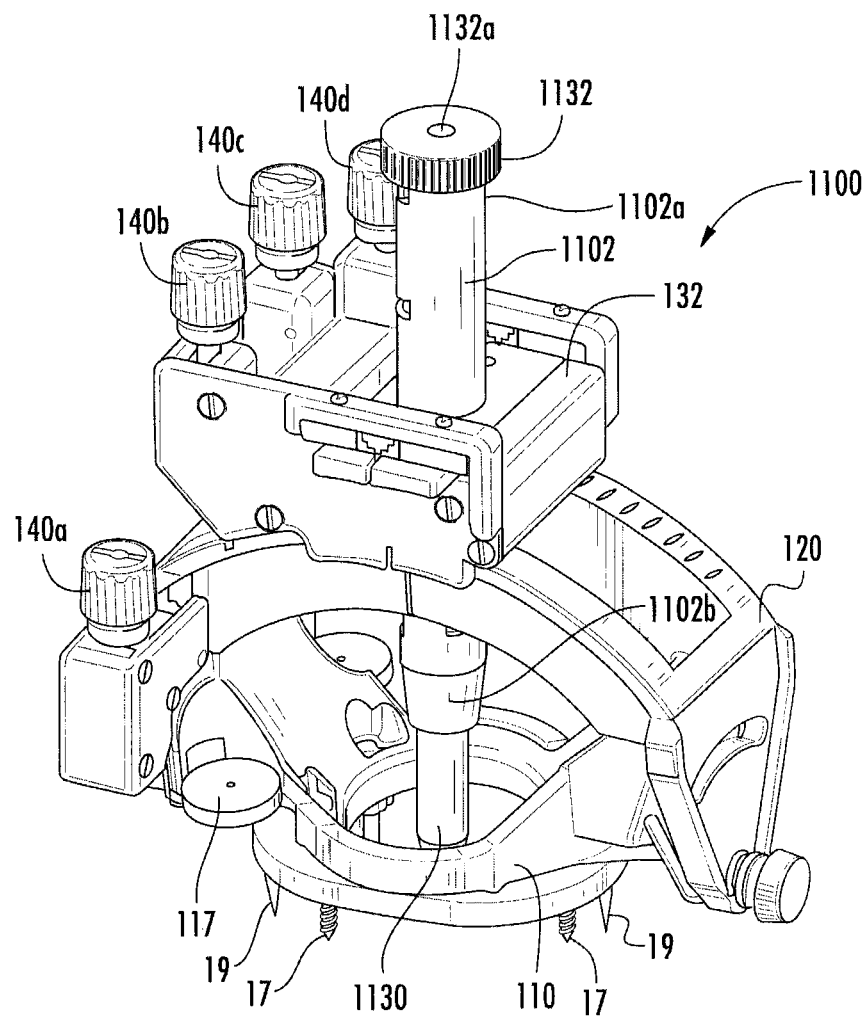
FIG. 18B is a perspective view of the trajectory frame of FIG. 18A and illustrating the catheter guide inserted within the guide and with a cap of the catheter guide secured to the proximal end portion of the guide.

As shown in FIGS. 18A-18B, after the skull fixation device 1122 is attached to the skull of a patient, the skull fixation device driver 1120 is removed from the guide 1102 and a catheter guide 1130 may be inserted within the guide 1102 through the proximal end 1102a thereof. The catheter guide 1130 includes a cap 1132 secured to a proximal end 1130a thereof that is threaded and configured to be threadingly secured to the threaded proximal end portion 1102a of the guide 1102. Alternatively, the cap 1132 of the catheter guide 1130 may be attached to the guide proximal end 1102a via a detent, interference fit, or via various other types of frictional engagement, and via various shapes and/or components that allow for quick removal, without limitation.

Figure 19:
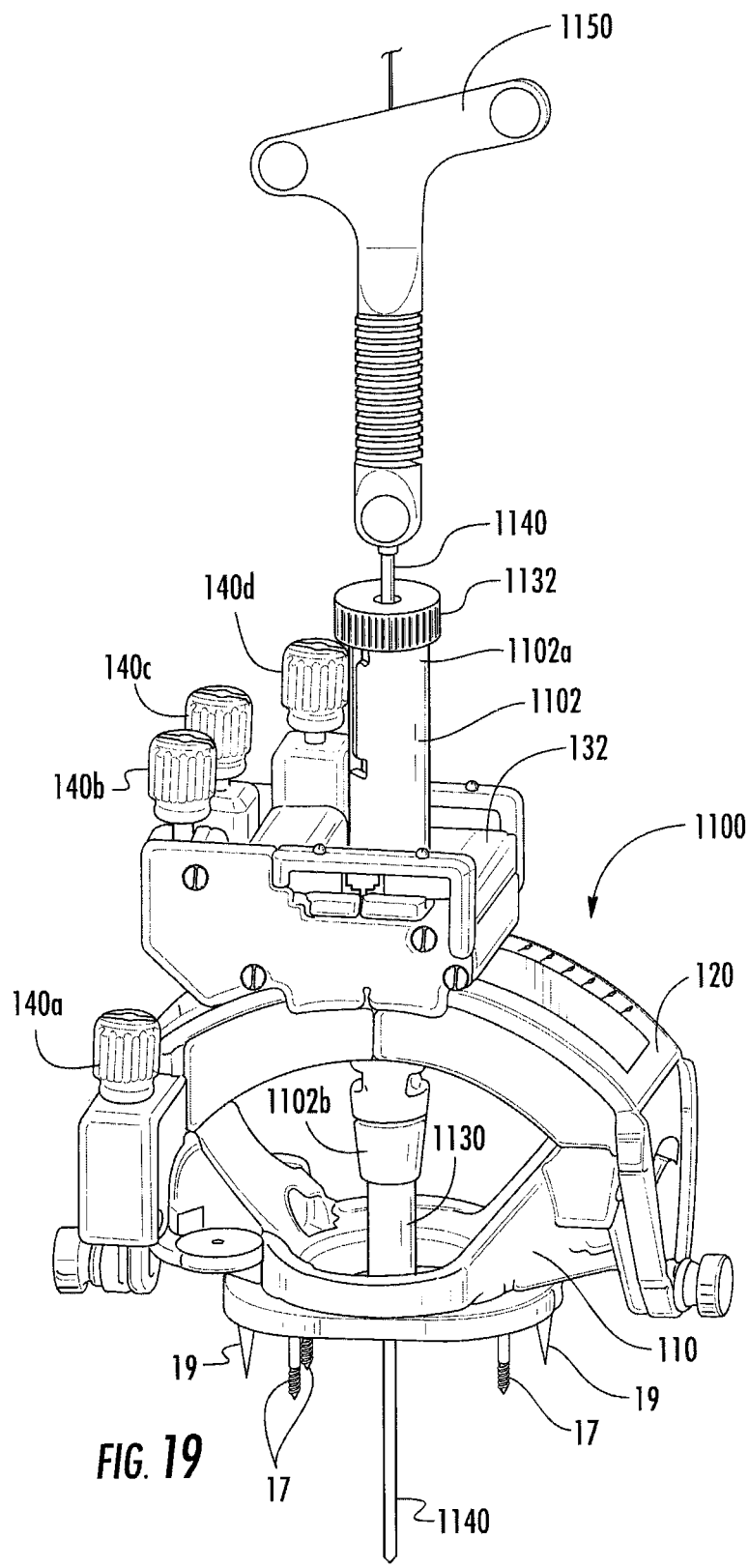
FIG. 19 is a perspective view of the trajectory frame of FIG. 18B and illustrating a catheter or other device advanced through the catheter guide of FIG. 18B.

The illustrated cap 1132 includes an opening 1132a to facilitate insertion of a probe or other device into and through the lumen 201 of the targeting cannula 200. FIG. 19 illustrates a catheter 1140 or other device advanced through the catheter guide 1130 via a tool 1150.

Figure 20A:
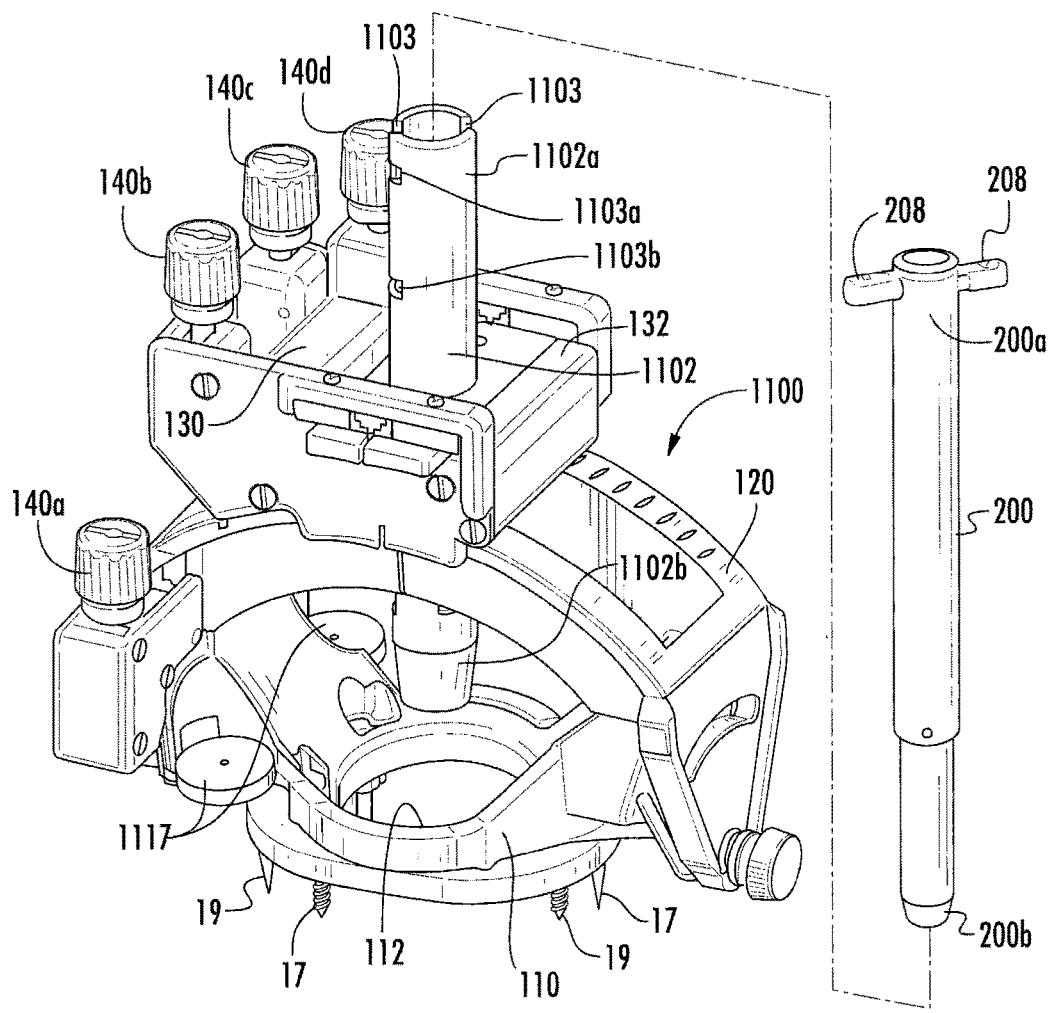
FIG. 20A is a partial exploded perspective view of a trajectory frame, according to some embodiments of the present invention, wherein the trajectory frame includes a guide for removably receiving and securing a targeting cannula or other device therewithin.
Figure 20B:
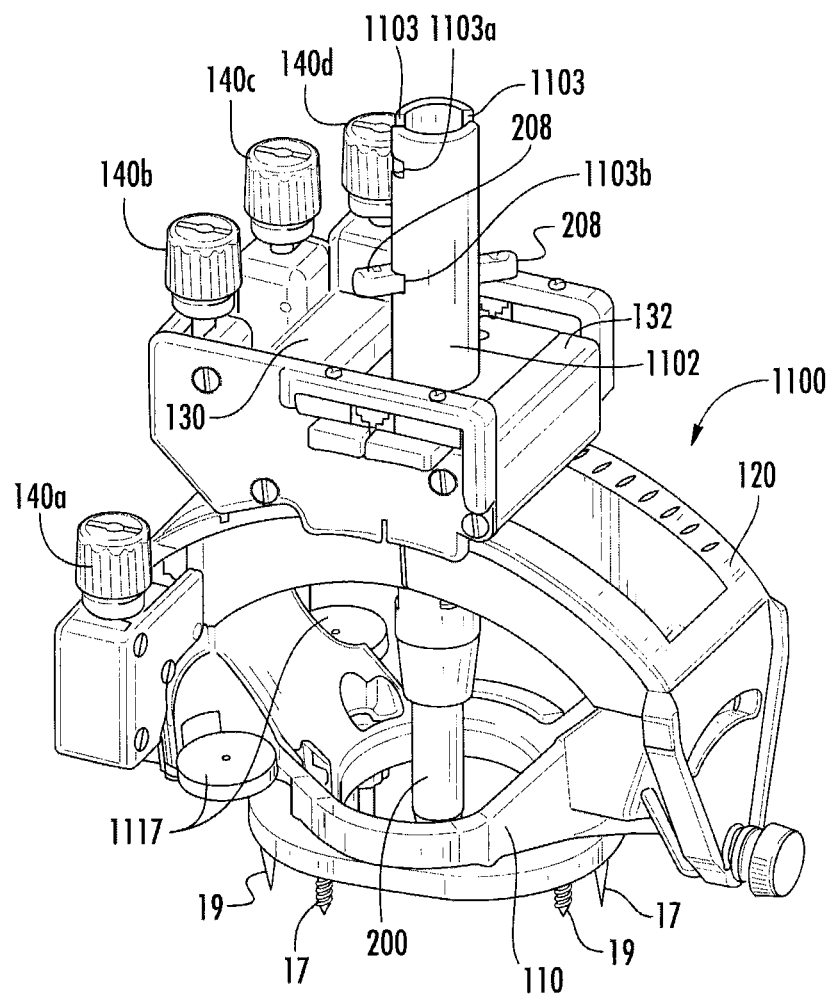
FIG. 20B illustrates the targeting cannula of FIG. 20A inserted within and secured to the guide.

Referring now to FIGS. 20A-20B, as shown, the trajectory frame 1100 has a proximal end portion 1102a that does not include a threaded proximal end portion 1102a. Various devices inserted within the guide 1102, such as the illustrated targeting cannula 200 can be removably secured to the guide via lugs, such as targeting cannula lugs 208, that cooperate with elongated slots 1103 in the guide 1102. The elongated slots 1103 merge into spaced-apart transversely extending upper ledge portions (e.g., slots) 1103a and transversely extending lower ledge portions (e.g., slots) 1103b. The distance between the upper ledge portions 1103a and the lower edge portions 1103b is typically between about 0.25 inches and about 5.0 inches.

By rotating a device within the guide 1102 such that the lugs, for example the targeting cannula lugs 208, cooperate with the upper ledge portions 1103a, a device can be securely held at a first or upper position. By inserting the device further within the guide 1102 and then rotating the device such that the lugs cooperate with the lower ledge portions 1103a, the device can be securely held at a second or lower position.

Referring now to FIGS. 21-33, the trajectory frame 1100 described above, modified to not require (but can include) the use of MRI and/or CT visible fiducials 117 and a targeting cannula 200 and to now include other cooperating components, are shown which can be used for non-MRI image guided systems such as camera-guided systems C, FIG. 33. The trajectory frame 1100 and components may be configured for use with "asleep" or "awake" neurological (e.g., brain) surgical systems. The frame 1100 and cooperating components can be sterile so as to comply with medical use requirements (and are typically held in a clean or sterile state in packaging prior to surgical use).

FIG. 21 illustrates the trajectory frame 1100 (e.g., also known as a trajectory guide) with the guide 1102 (e.g., also known as a support column) holding an optical tracking probe 1162 according to embodiments of the present invention. This tracking probe 1162 includes a plurality of spaced apart fiducials 1164, typically reflective elements that may comprise spherical shaped reflective members. The reflective members 1164 can be arranged as an array of fiducials 1164a in a fixed geometric pattern relative to one another that may be positionally adjusted as a group. The array can include four (or more) reflective members that can be of any shape, e.g., reflective spheres, dots or tape. The array can be configured to allow the navigation/tracking system to generate AC-PC image views. The reflective elements can have a reflective coating and may be passive spheres such as those available from Northern Digital Inc. (ndigital.com) as NDI passive spheres that attach via snap-on posts.

The tracking probe 1162 is held in an elongate tracking probe mount 1160 that can include lugs 1168 that releasably attach to the guide 1102 that is attached to the X-Y support table 132. The tracking probe mount 1160 includes upper and lower ends, 1160*a*, 1160*b*, respectively. The lower end 1160*b* is typically held in the guide 1102 so that it is positioned to extend below the bottom or distal end of the guide 1102*b* to be able to bottom out or contact the skull or scalp of the patient to define a desired trajectory. The optical tracking probe 1162 can be held above the top end 1160*a* of the mount 1160.

Figures 23A, 23B, 23C:
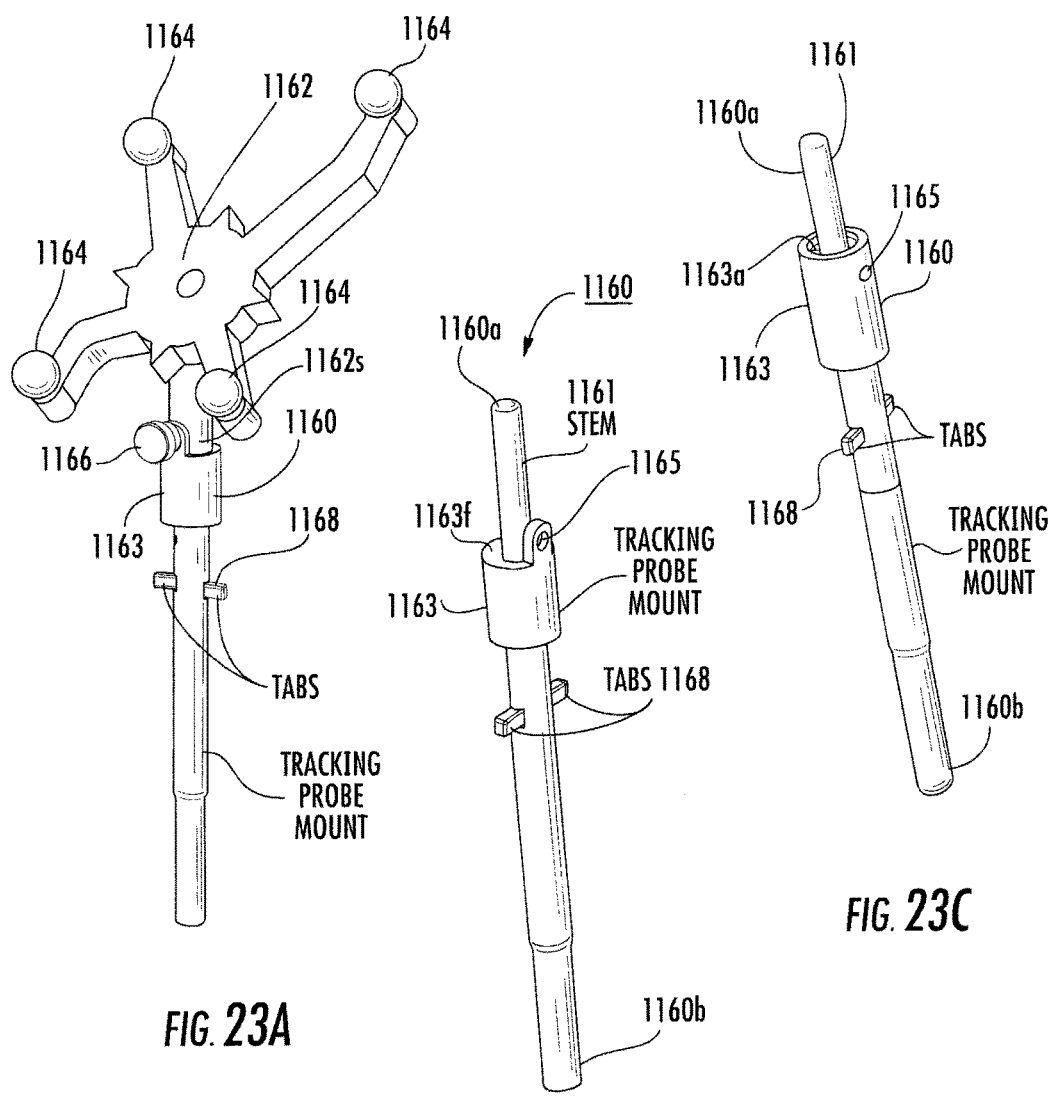
FIG. 23A is a side perspective view of a tracking probe mount holding the tracking probe for releasable attachment to the support column of the trajectory frame shown in FIGS. 21 and 22A according to embodiments of the present invention.
FIGS. 23B and 23C are side perspective views of exemplary tracking probe mounts, shown without the tracking probe, according to embodiments of the present invention.
Figure 23G:
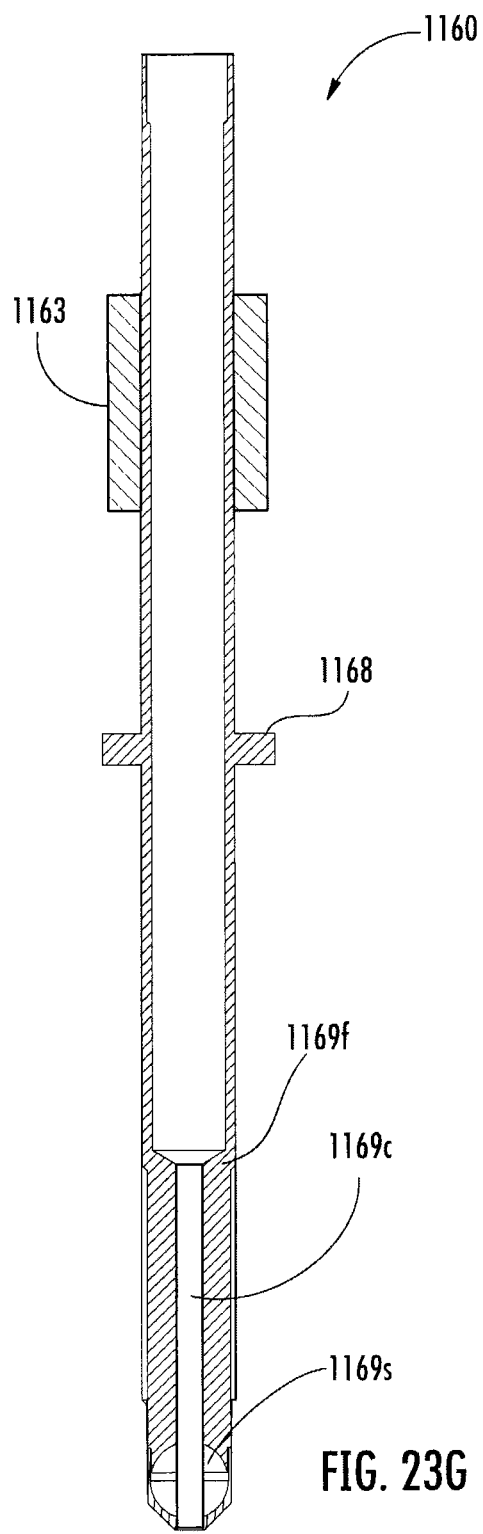
FIG. 23G is a section view of an exemplary tracking probe mount shown in FIGS. 23E/23F according to embodiments of the present invention.

FIG. 23A shows the optical array 1162 with an exemplary mount 1160. FIGS. 23B and 23C illustrate two alternate configurations of the mount 1160, each having laterally extending lugs 1168 and a collar 1163 that surrounds an upwardly extending stem 1161 that slidably extends into a bore in a downwardly extending support member 1162*s* of the optical array 1162. FIG. 23B illustrates a flat closed upper surface 1163*f* of the collar 1163 that can abut a flat lower surface of the optical array support member 1162*s*. FIG. 23C illustrates that the collar 1163 can have an open annular channel that receives a lower end of the optical array support member 1162*s*. The lower portion of the collar 1163 can engage the top of the guide 1102*a*.

FIGS. 23A-23C illustrate that the collar 1163 can include at least one aperture 1165 that allows for a fixation member 1166 to extend therethrough to lockingly engage the lower end portion of the optical array support member 1162*s*. Although shown as one fixation member and aperture, a plurality of circumferentially spaced apart members/apertures may be used. Also, other fixation configurations may be used including, for example, clamps, frictional engagement grips, bayonet fittings or other configurations that lock the device 1162 in position on or in the mount 1160 so that the optical array 1162 does not flex or move other than with the mount 1160 in the guide 1102.

FIGS. 23D-23G illustrate another embodiment of the tracking probe 1162 and tracking probe mount 1160. In this embodiment, the tracking probe mount 1160 can optionally include a through channel 1169*c* and the tracking probe 1162 can include an aligned port 1169*p*. One or more different devices can optionally be guided down through the channel 1169*c* for a desired trajectory provided by the tracking probe mount 1160. The tracking probe mount 1160 can include image fiducials 50F (FIG. 9A) that may include MRI and/or CT visible segments, such as fluid-filled segments, which may optionally comprise a wall with an enclosed space comprising fluid 1169*f* surrounding all or part of the open channel 1169*c*. The MRI/CT visible segments (image fiducials) can comprise a fluid-filled spherical member 1169*s* at a distal end portion of the tracking probe mount 1160. The trajectory frame 100 may include fluid-filled fiducials 50F about a perimeter of an aperture formed by the base 110 (FIG. 22B).

Figure 22A:
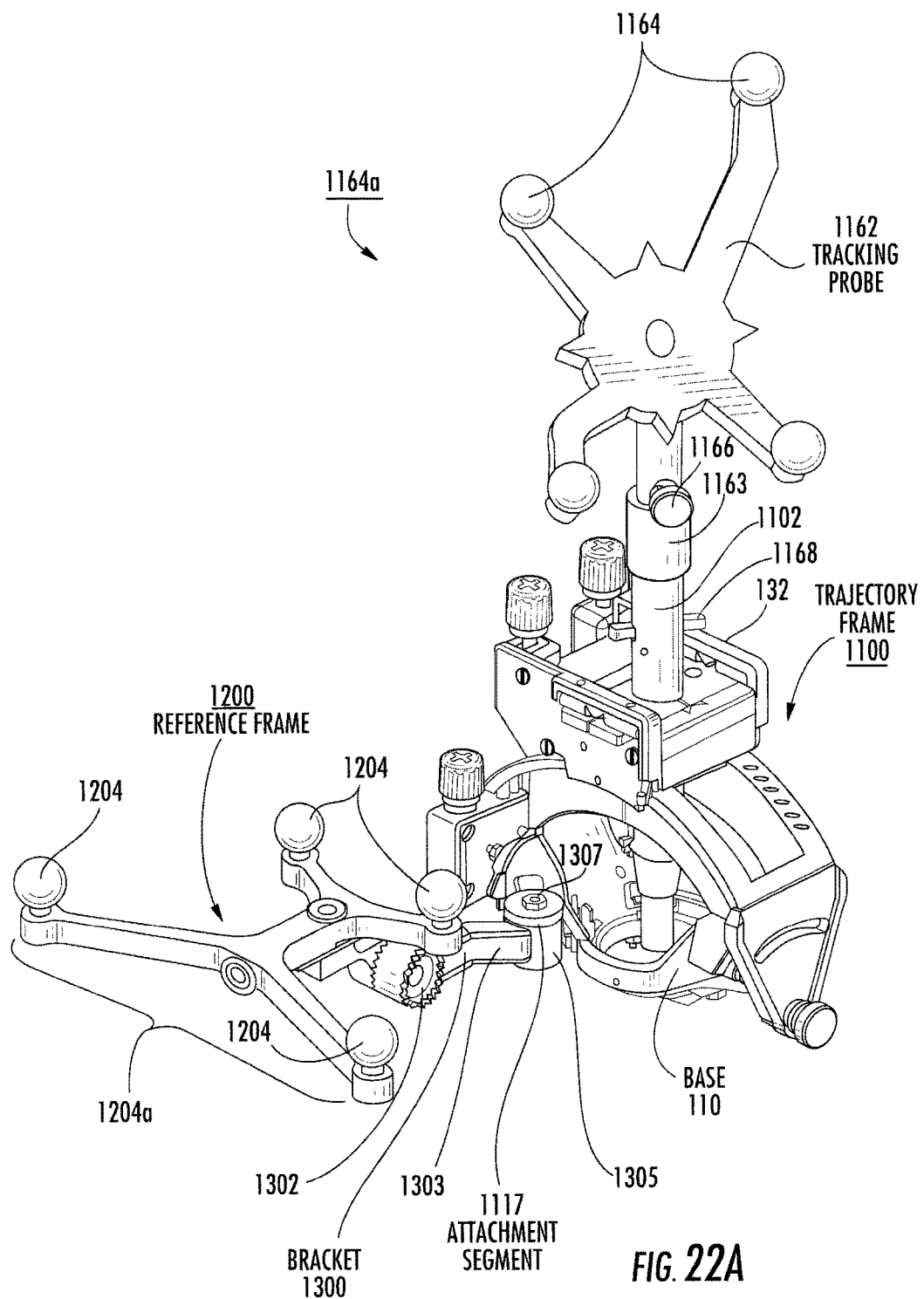
FIG. 22A is a side perspective view of a trajectory frame with both an optical tracking probe and an optical reference frame attached to the trajectory frame according to embodiments of the present invention.
Figure 22B:
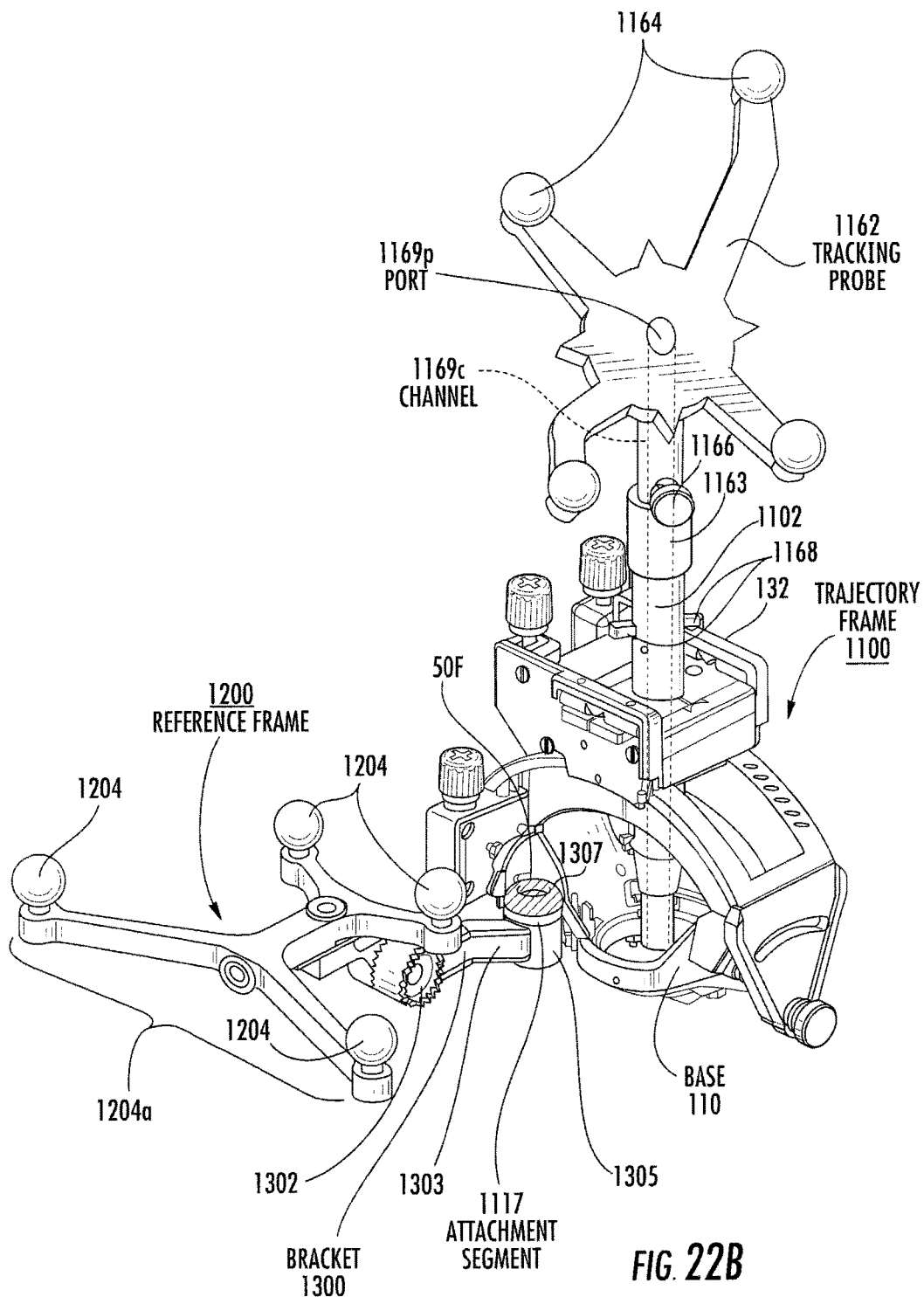
FIG. 22B is a side perspective view of a trajectory frame with an optical tracking probe with a through channel with image fiducials (e.g., fluid-filled segments detectable in MRI and/or CT images) and an optional optical reference frame attached to the trajectory frame according to embodiments of the present invention.

FIGS. 22A and 22B illustrate that the trajectory frame 1100 can also optionally be configured to hold both the optical tracking probe 1162 and an optical reference frame 1200. The optical reference frame 1200, where used, can include an array of reflective members 1204*a*, typically four spherical reflective members but other shapes can be used such as those discussed above with respect to the tracking probe 1162.

In some embodiments, a first planned trajectory can be generated using a camera-based or EM based navigation/tracking system with a corresponding tracking probe 1162 or 1500 (FIG. 34A), for example. A confirmation or concordance trajectory can be calculated (or fine adjustments made) using the CT and/or MRI image fiducials 50F which can be on the optical tracking probe mount 1160 or the EM tracking probe mount 1510 (FIG. 34B) and/or trajectory frame 1100. In other embodiments, a targeting cannula 200 (FIG. 8B) can be interchangeably placed in the bore of the guide 1102 after removing the tracking probe 1162, alone, or the tracking probe 1162 with the tracking probe mount 1160, (or EM probe 1500 or EM probe mount 1510, FIGS. 34A, 34B) and used for the concordance or confirmation/adjustment review trajectory evaluation. In any event, using the CT or MRI Scanner to supplement or confirm the trajectory can reduce any required imaging time from an MRI and/or CT Scanner and yet provide a precise trajectory.

The reference frame 1200 can be held by a bracket 1300 that is attached to the trajectory frame 1100. The reference frame 1200 can extend a distance beyond an outer surface of the platform 130 with the fiducials 1204 in a fixed geometric pattern that may extend along a common plane or at different planes and can allow for AC-PC image views. The reference frame 1300, when attached to the trajectory frame 1100, may be particularly suitable for "awake" brain surgical procedures to track patient movement. For "asleep" neuro surgeries, the reference frame 1200 may be attached to the trajectory frame 1100 and/or a head fixation frame (not shown).

The reference frame 1200 can be configured to extend from a defined one of a left side or right side or can be configured to be able to extend from a selected either side of the trajectory frame 1100, when looking from a front of a patient. The bracket 1300 can have a dedicated left side attachment configuration, a dedicated right side configuration or a configuration that can be used to extend off either side of the trajectory frame 1100. Two trajectory frames may be used for bilateral procedures, each with a respective reference frame 1200 (not shown).

Figure 24:
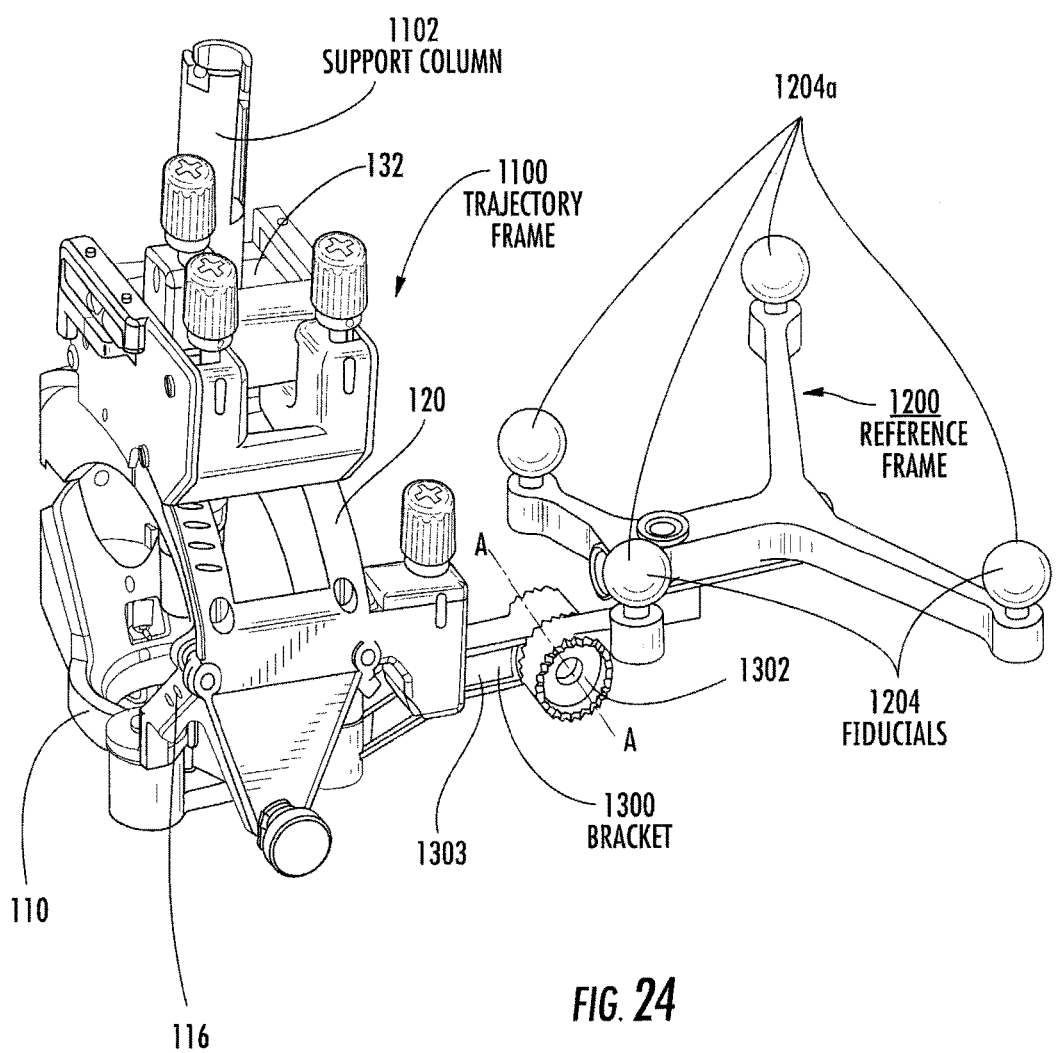
FIG. 24 is a side perspective view of the trajectory frame shown in FIG. 21, but shown without the tracking probe according to embodiments of the present invention.
Figure 25A:
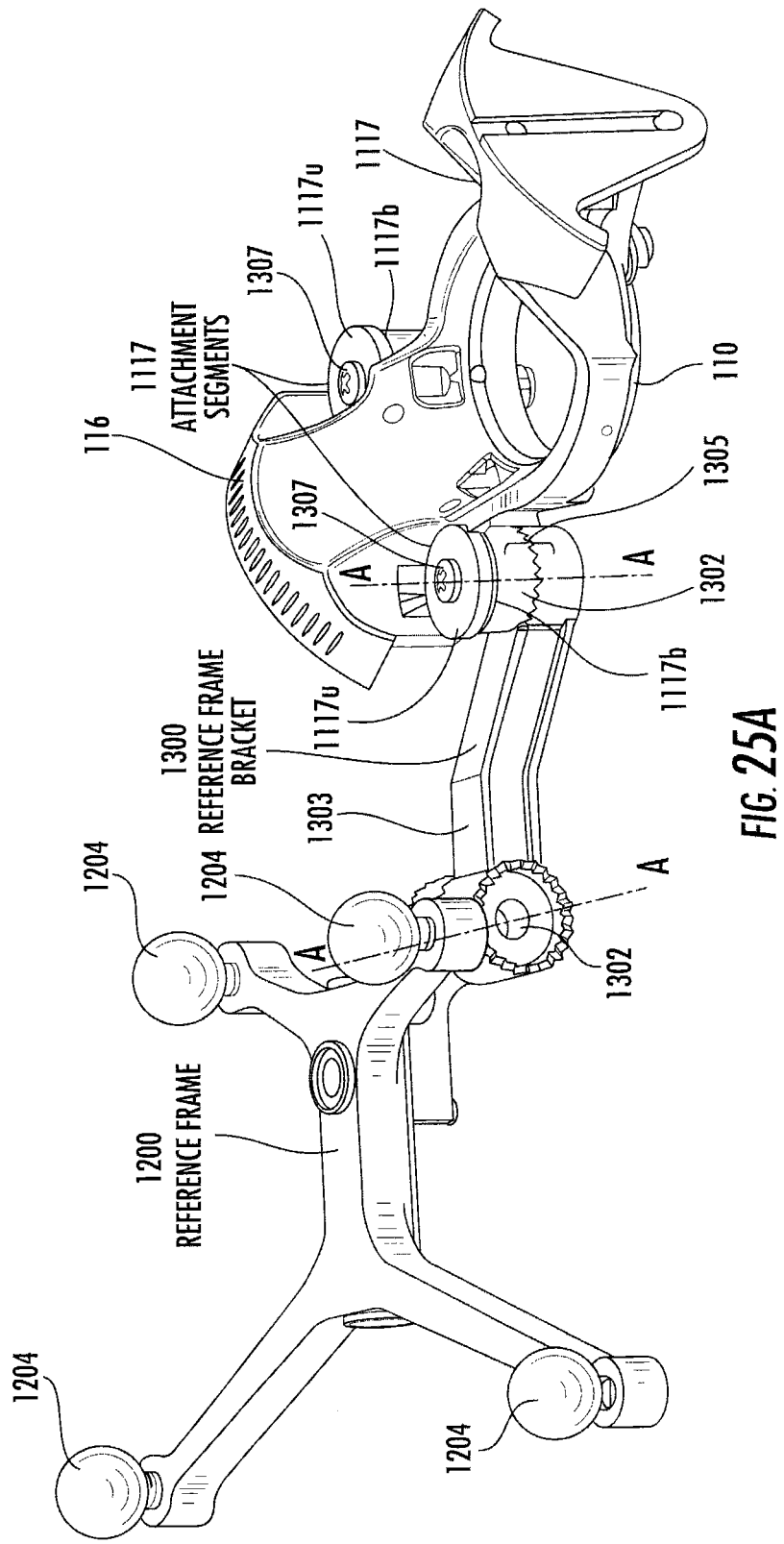
FIG. 25A is an enlarged side perspective view of a bottom portion of the trajectory frame shown in FIG. 21 illustrating exemplary attachment configurations according to embodiments of the present invention.

The bracket 1300 can include at least one starburst connector 1302. The starburst connector 1302 can allow for positional adjustment of the reference frame 1200 relative to the patient and/or base 110 of trajectory frame 1100. FIGS. 22, 24 and 25A illustrate that the at least one starburst connector 1302 can include a starburst connector that resides closer to the reference frame 1200 than the base 110. The rotational or swivel axis A-A (FIG. 24) can extend perpendicular to the length dimension of the arm or link 1303.

The trajectory frame 1100 can have three concentric ears 1117$_1$, 1117$_2$, 1171$_3$ (FIG. 27C), positioned about the base 110 and can have two that reside closer together than a third, e.g., the ears 1117 can be asymmetrically oriented about a circle drawn through the centers of the ears 1117.

As shown in FIG. 22, the trajectory frame 1100 can have one or more attachment ears 1117 that extend outside the base 110, above the base 110 and under the X-Y support table 132 and/or platform 130. The one or more ears 1117 can be a plurality of ears 1117 that extend outside a perimeter of the base. The ears 1117 can be the surfaces that support MRI fiducials 117 (FIG. 3A) when used in MRI-image guided systems. The ears 1117 can have upper and lower surfaces, 1117*u*, 1117*b* (FIG. 25A), respectively, one or both of which can be planar.

Figure 26A:
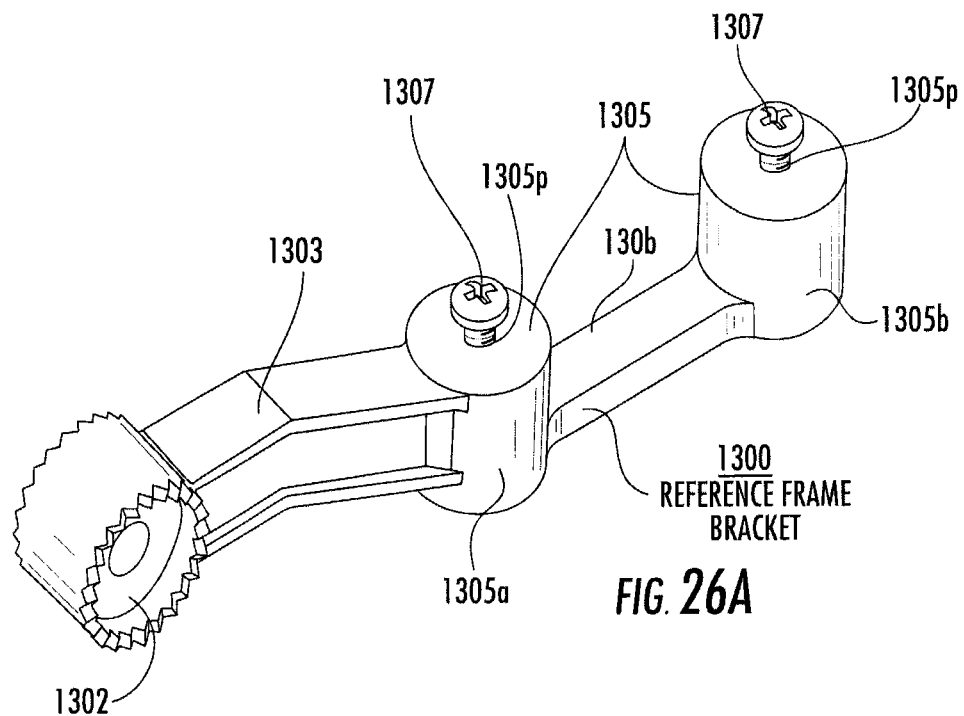
FIG. 26A is a top perspective view of an exemplary bracket for attaching a reference frame to the trajectory frame according to embodiments of the present invention.

As shown in FIGS. 22 and 25A, the bracket 1300 can have at least one upright segment 1305 that is attached to a respective ear 1117. As shown in FIGS. 22 and 25A, a pin or screw 1307 can be used to attach the upright segment 1305 to the ear 1117 and the pin or screw 1307 can extend down through the ear 1117, typically through a pin or screw aperture 1117*p* and connector aperture 1305*p* (FIGS. 26A, 27A). However, the upright segment 1305 can also be bonded, glued and/or ultrasonically inserted into or moldably attached or otherwise integrated into a respective ear 1117.

The upright segment 1305 can have a top surface that abuts the bottom surface of a respective ear 1117*b*. Although not shown, the upright segment 1305 can have prongs or overlying wall segments that reside above and below the ear 1117 with a channel that receives and holds the ear 117 therebetween for attachment or the upright segment 1305 can reside on the upper surface of the ear and be attached to the ear 1117. The upright segment 1305 can support an outwardly extending linkage or arm 1303 that places the reference frame 1200 at a desired closely spaced apart position from the base 110. The arm or linkage 1303 can have a length that is typically between about 0.25 inches to about 3 inches and can raise up as it extends outward away from the base 110.

FIGS. 25A, 25B, 26A and 26B illustrate one example of a bracket 1300. In this embodiment, the bracket 1300 can have two upright segments 1305, e.g., first and second segments 1305*a*, 1305*b*, each of which can attach to spaced apart ears 1117. Typically, the upright segments 1305*a*, 1305*b* are connected by a laterally extending straight arm 1306 that is at a level below the upper surface of the first and second segments 1305 and that can be below that of the outwardly extending arm or linkage 1303. The bridging or connecting arm 1306 can extend proximate to but under the arcuate arm 116. The dual upright supports may provide a more stable attachment for the arm 1303 and/or cantilevered reference frame 1200.

Figure 25B:
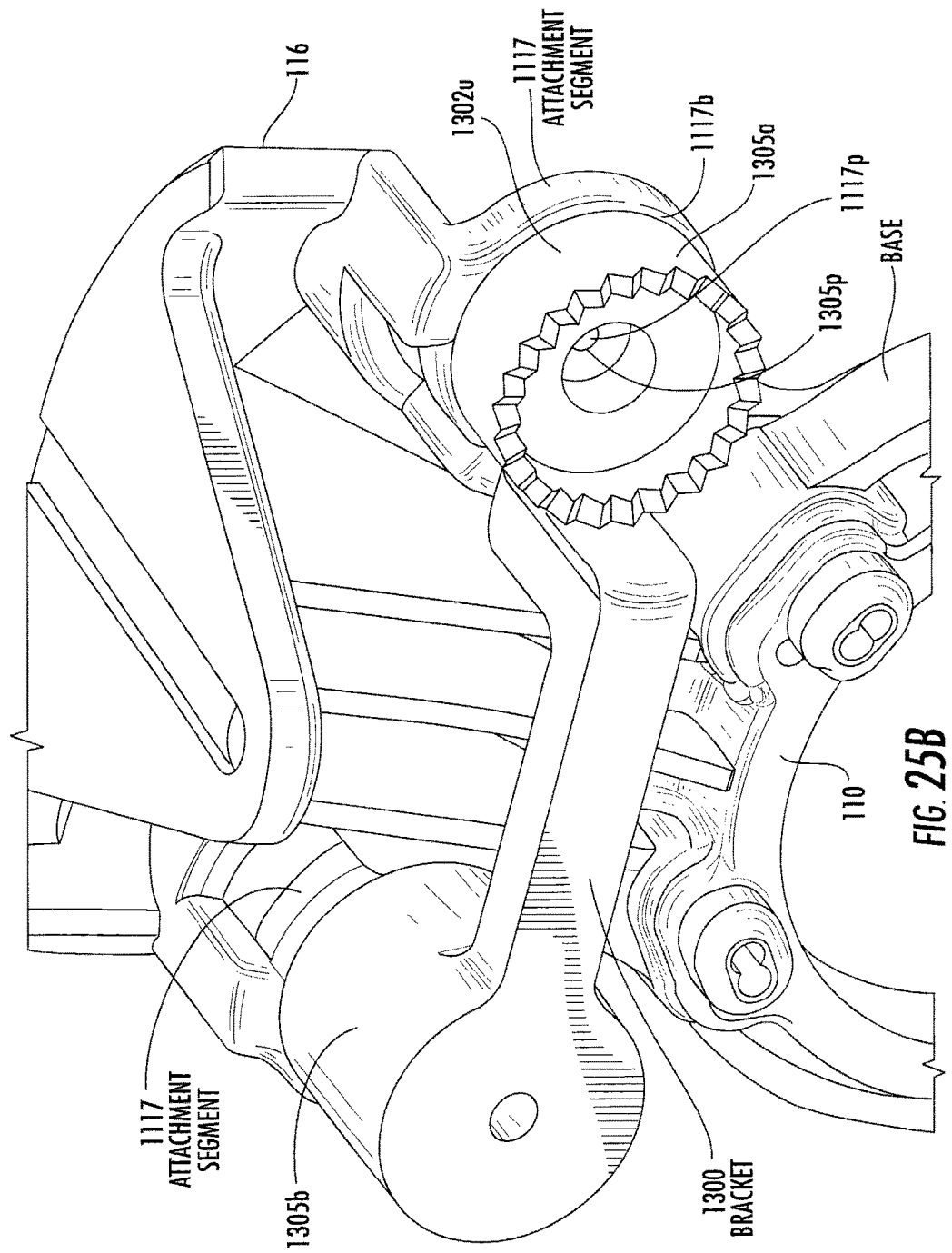
FIG. 25B is a greatly enlarged partial bottom perspective view of the bracket shown in FIG. 25A.

The bracket 1300 can include a plurality of the starburst connectors 1302, including one forming part of the upright segment 1305 proximate the base 110 and one residing further away from the base 110 and proximate the reference frame 1200. FIG. 25B shows the upper component of the starburst connector 1302*u* attached to the underside of the ear 1117*b*. Each can have an axis A-A that is perpendicular to the other. The axis A-A of the upright segment 1305 can allow for front to back or right to left positional adjustment. The axis A-A of the connector 1302 proximate the reference frame 1200 can allow up and down adjustment of the arm 1303 and thus, the reference frame 1200.

Figure 26B:
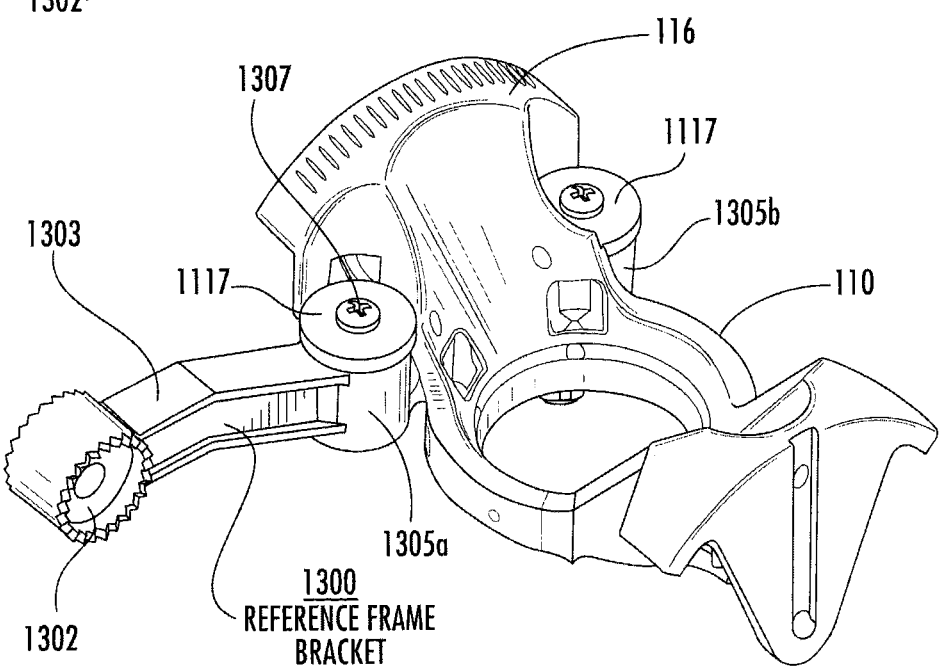
FIG. 26B is an assembled view of the bracket shown in FIG. 26A to attachment segments of the trajectory guide according to embodiments of the present invention.

FIGS. 26A and 26B illustrate that the upright segments 1305 are not required to have starburst connectors 1302. However, where used, typically only the upright segment closest to the arm or linkage 1303 will have the starburst connector 1302 for rotational adjustability of the arm or linkage 1303. In any event, the bracket segments 1305*a*, 1305*b* can be reversed to attach to the other ears 1117 so that the link 1303 extend from a desired side of the trajectory frame.

FIGS. 27A-27C illustrate another exemplary bracket 1300'. In this embodiment, a single upright segment 1305 is used to attach to a single ear 1117. FIG. 27A illustrates the bracket 1300' with the lower component of the starburst connector 1302*b* while FIG. 27B illustrates the upper component 1302*u* attached to an underside 1117*b* of the ear 1117 of the trajectory frame 1100. Again the two axis of rotations A-A can be orthogonal to each other. The upright segment 1305 can be attached to the first, second or third ear 1117$_1$-1117$_3$.

Figure 28:
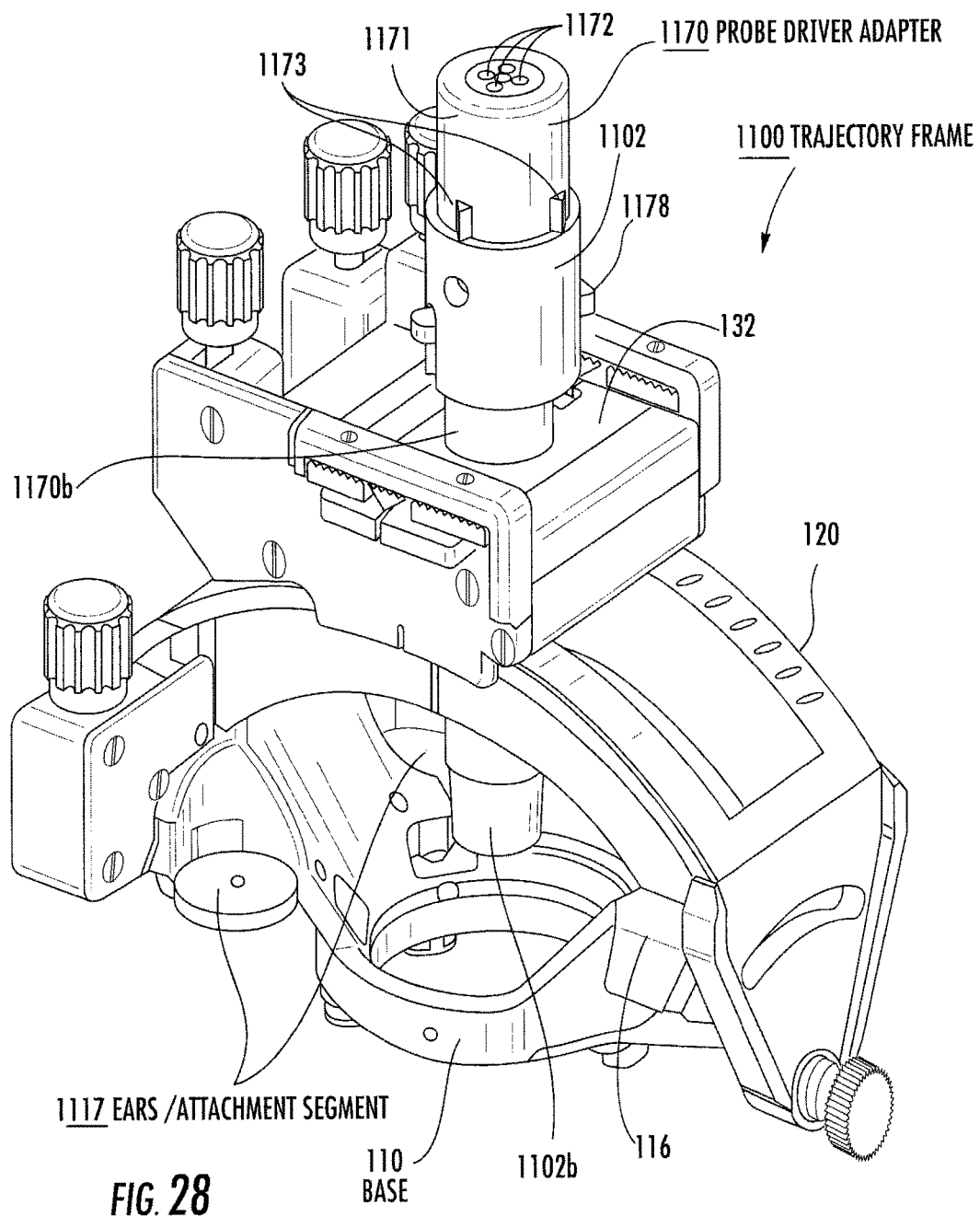
FIG. 28 is a side perspective view of the trajectory frame shown in FIGS. 21 and 22 illustrating the support column releasably holding a microelectric (MER) probe drive adapter, typically for awake deep brain surgeries, according to embodiments of the present invention.
Figure 29A:
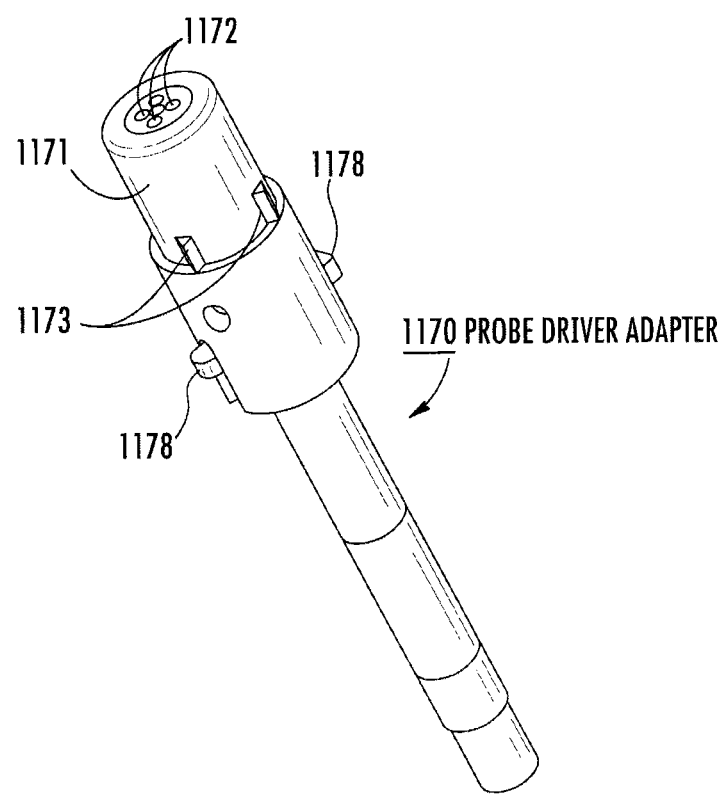
FIG. 29A is a side perspective view of the MER probe drive adapter shown in FIG. 28 according to embodiments of the present invention.
Figure 29B:
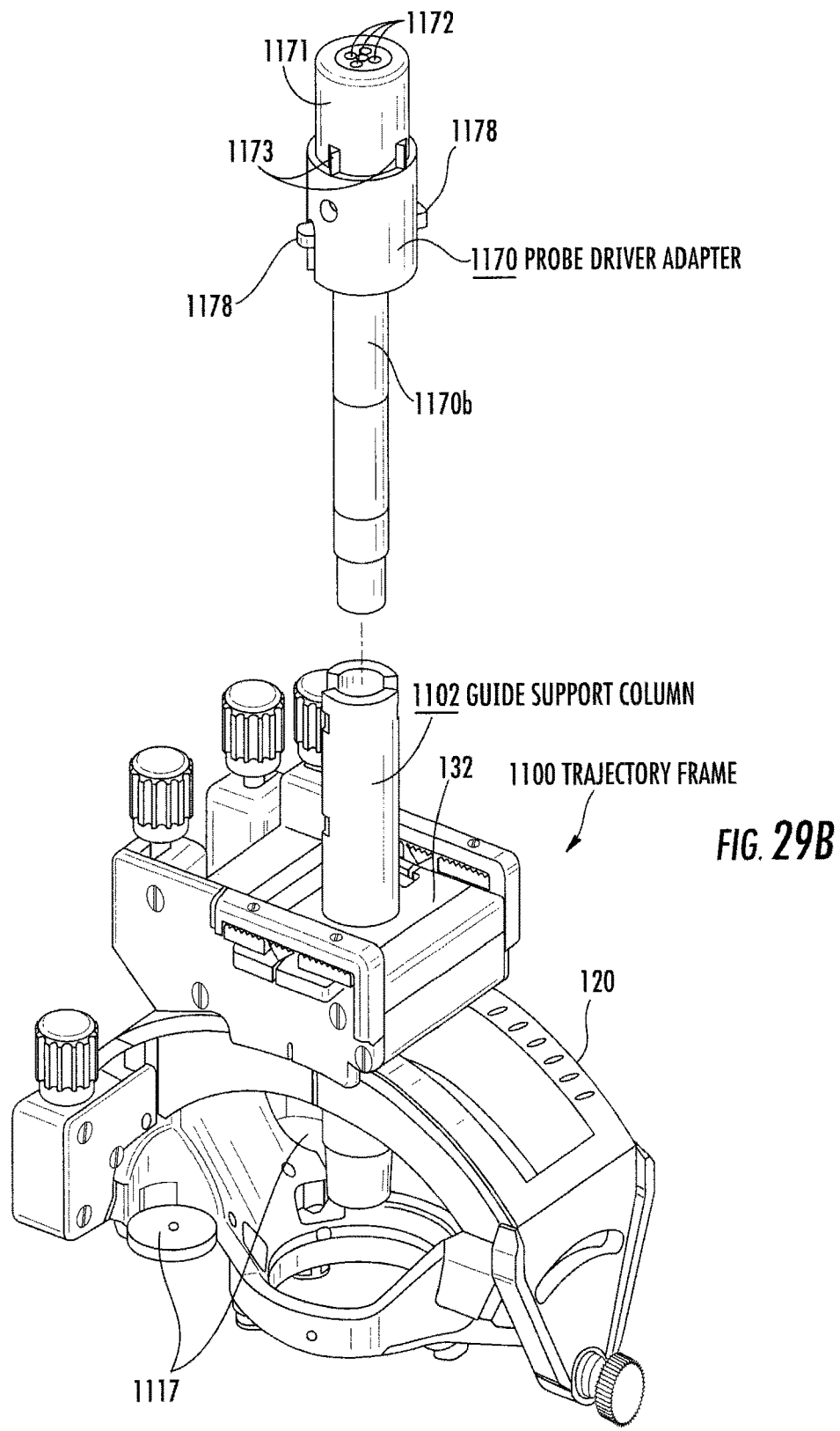
FIG. 29B is a partial exploded view of the MER probe drive adapter and trajectory frame shown in FIG. 29A according to embodiments of the present invention.
Figure 30:
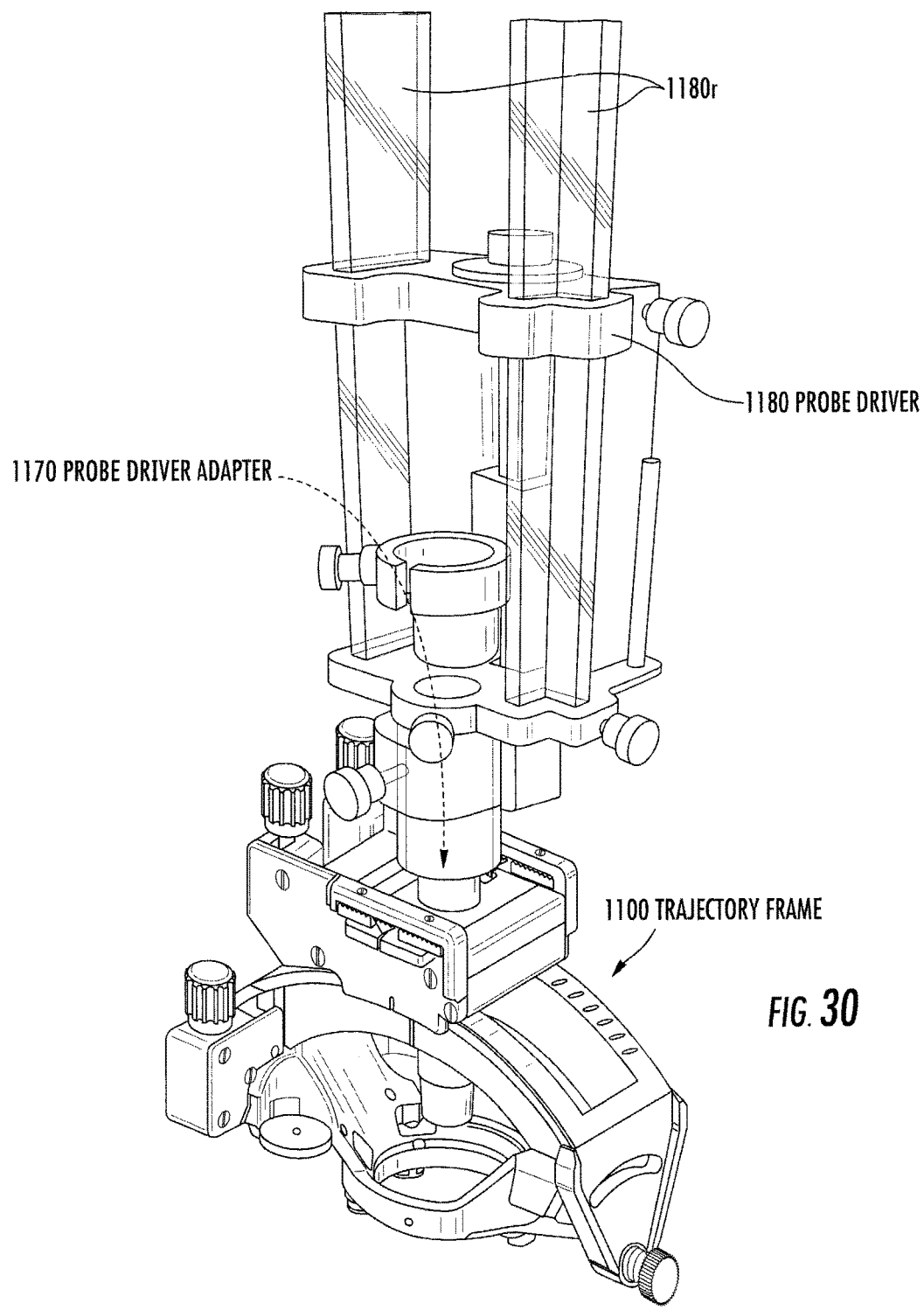
FIG. 30 is a side perspective view of a trajectory frame holding a probe driver using the MER probe driver adapter shown in FIGS. 28, 29A, 29B, according to embodiments of the present invention.

FIGS. 28, 29A and 29B show the trajectory frame 1100 with the guide/support column 1102 releasably holding a microelectric (MER) probe driver adapter 1170, typically used for "awake" brain surgeries, according to embodiments of the present invention. The probe driver adapter 1170 can hold the MER probe driver adapter body 1171 with microelectrode (entry) ports 1172 at a location that positions the microelectrode ports 1172 exposed above the adapter body 1170*b*. The adapter body 1170*b* can have outwardly extending lugs 1178 that engage the slots in the guide 1102. The MER probe drive adapter body 1171 can have radially extending tabs 1173 that define a stop for the upper portion of the adapter body 1171 so that it extends a desired distance above the lugs 1178 and/or so that the driver engages the probe drive adapter at a desired position. The MER probe drive adapter body 1171 can matably engage a drive system 1180 (FIG. 30) such as the NEXDRIVE® drive system with upwardly/outwardly extending rails 1180*r* (FIG. 30) from Medtronics, Inc. As shown in FIG. 30, the probe drive adapter 1170 resides between the rails 1180*r* attached to a support frame of the probe driver system 1180.

Figure 31A:
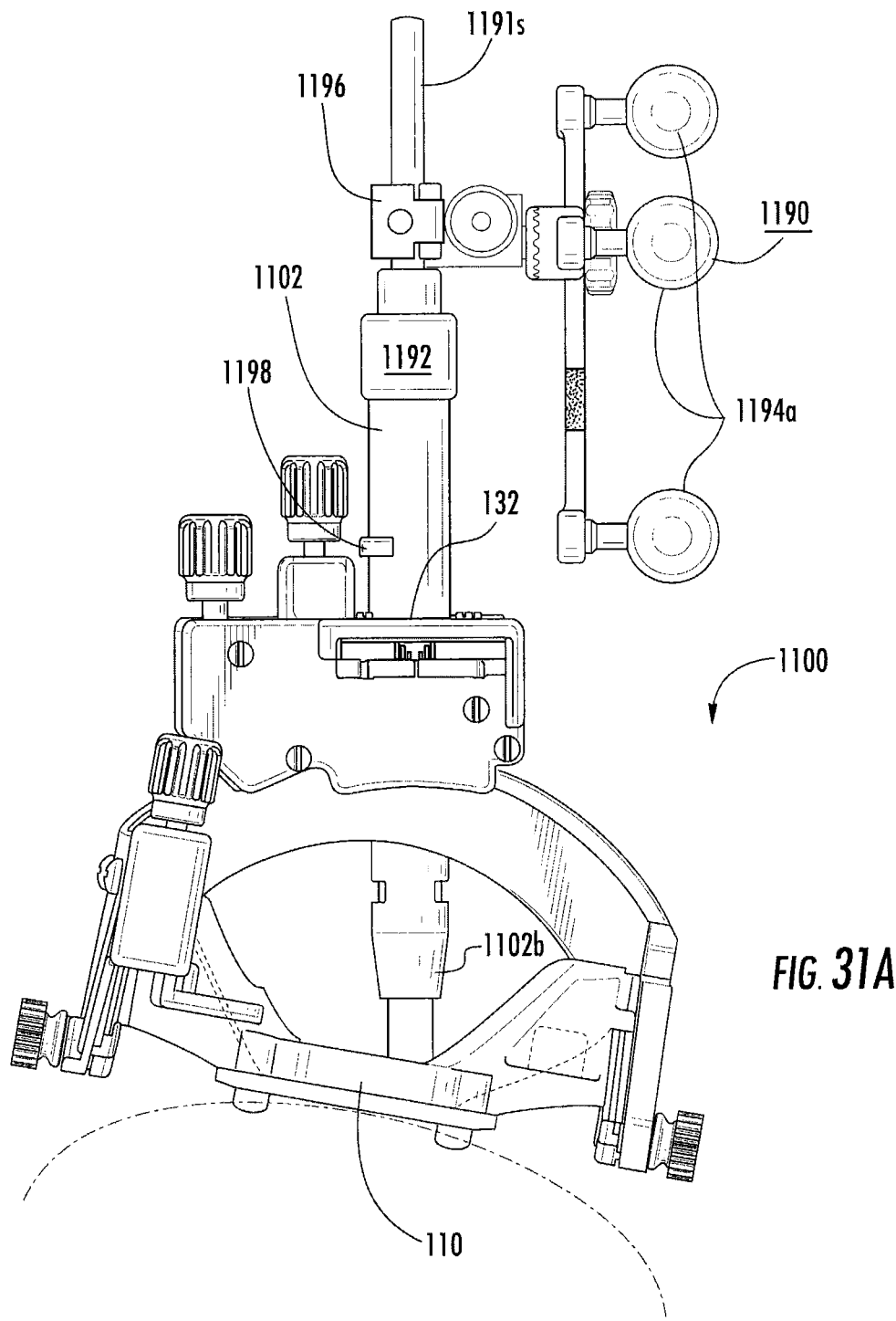
FIG. 31A is a side perspective view of a trajectory frame holding a universal tracker according to embodiments of the present invention.
Figure 31B:
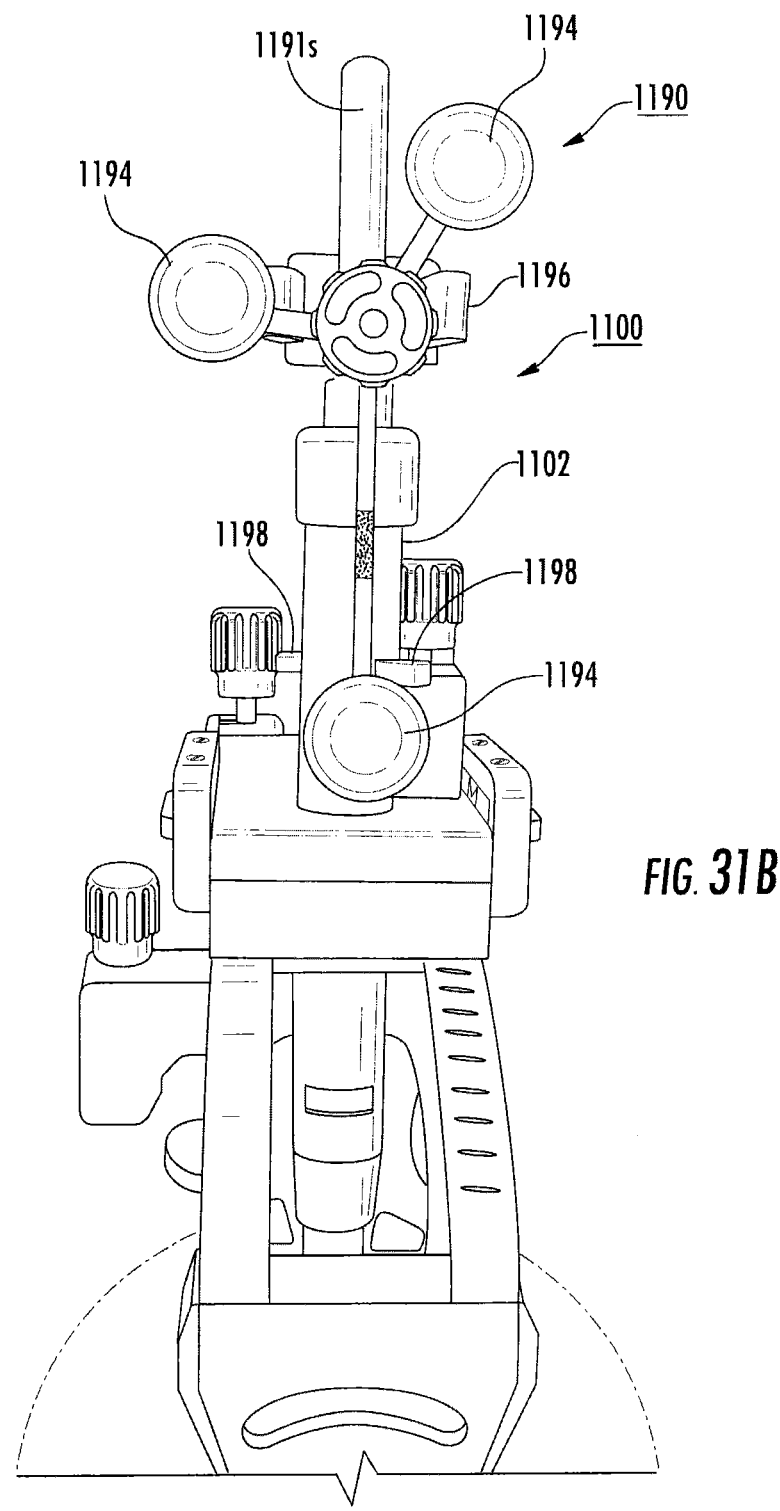
FIG. 31B is a side/front view of the assembly shown in FIG. 31A.

FIGS. 31A and 31B illustrate the trajectory frame 1100 holding a universal tracker 1190 according to embodiments of the present invention. The universal tracker 1190 typically includes an array 1194*a* of two, three, four or more (typically between about 2-10) (shown as three) reflective members. The reflective members 1194 are shown by way of example as spherical reflective members. As discussed with the other tracking probe 1162 above, the reflective members 1194 can have a reflective coating, tape and/or other reflective feature detectable by a camera or other tracking system and may be passive spheres such as those available from Northern Digital Inc. (ndigital.com) as NDI passive spheres that attach via snap-on posts.

The universal tracker 1190 can be held in an elongate tracking probe mount 1190*m* that can include lugs 1198 that releasably attach to the guide 1102 that is attached to the platform 130. The tracking probe mount 1190*m* includes upper and lower ends, 1190*a*, 1190*b*, respectively. The lower end 1190*b* is typically held in the guide 1102 so that it is positioned to extend below the bottom or distal end of the guide 1102*b* to be able to bottom out or contact the skull or scalp of the patient to define a desired trajectory. The optical universal tracker reflective members 1190 can be held external of the mount 1190*m*.

Figures 31C, 31D:
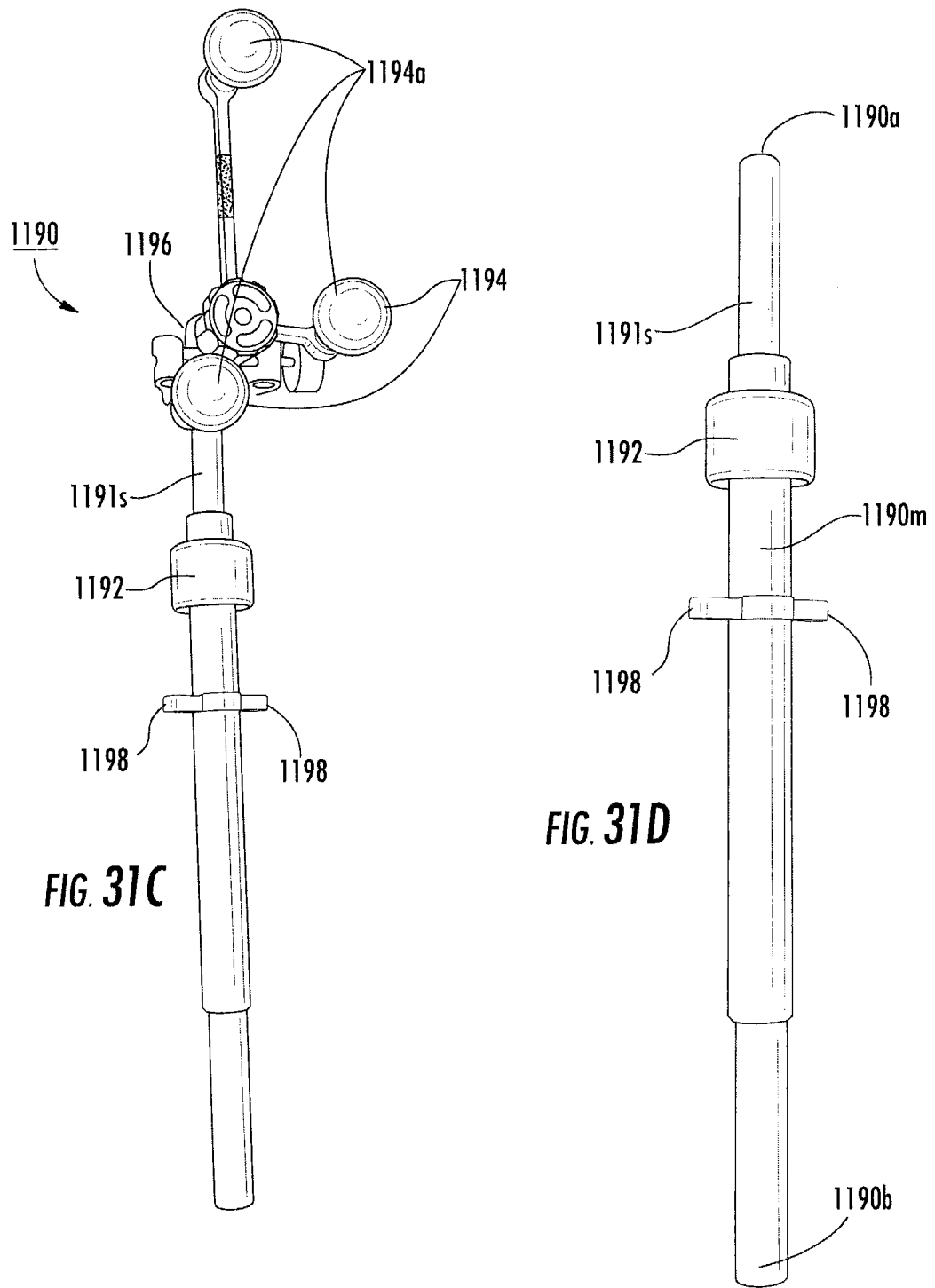
FIG. 31C is a front view of a tracker guide holding the universal tracker for releasable attachment to a support column/guide of the trajectory frame according to embodiments of the present invention.
FIG. 31D is a front view of the tracker guide without the universal tracker shown in FIGS. 31A-C according to embodiments of the present invention.

FIG. 31C shows the universal tracker 1190 with the optical (reflective member) array 1194*a* for releasable attachment to a support column of the trajectory frame 1100. The lowest of the reflective members (e.g., shown as spheres) 1194*a* can be held at between about 5-6 mm above the lugs 1198, in some embodiments.

FIG. 31D is a front view of the universal tracker 1190 without the optical (reflective members) array 1194*a*. The tracker mount 1190*m* includes an upwardly extending stem 1191*s* that holds the optical array bracket 1196 and a collar 1192 that can engage the top of the guide 1102.

Figure 32:
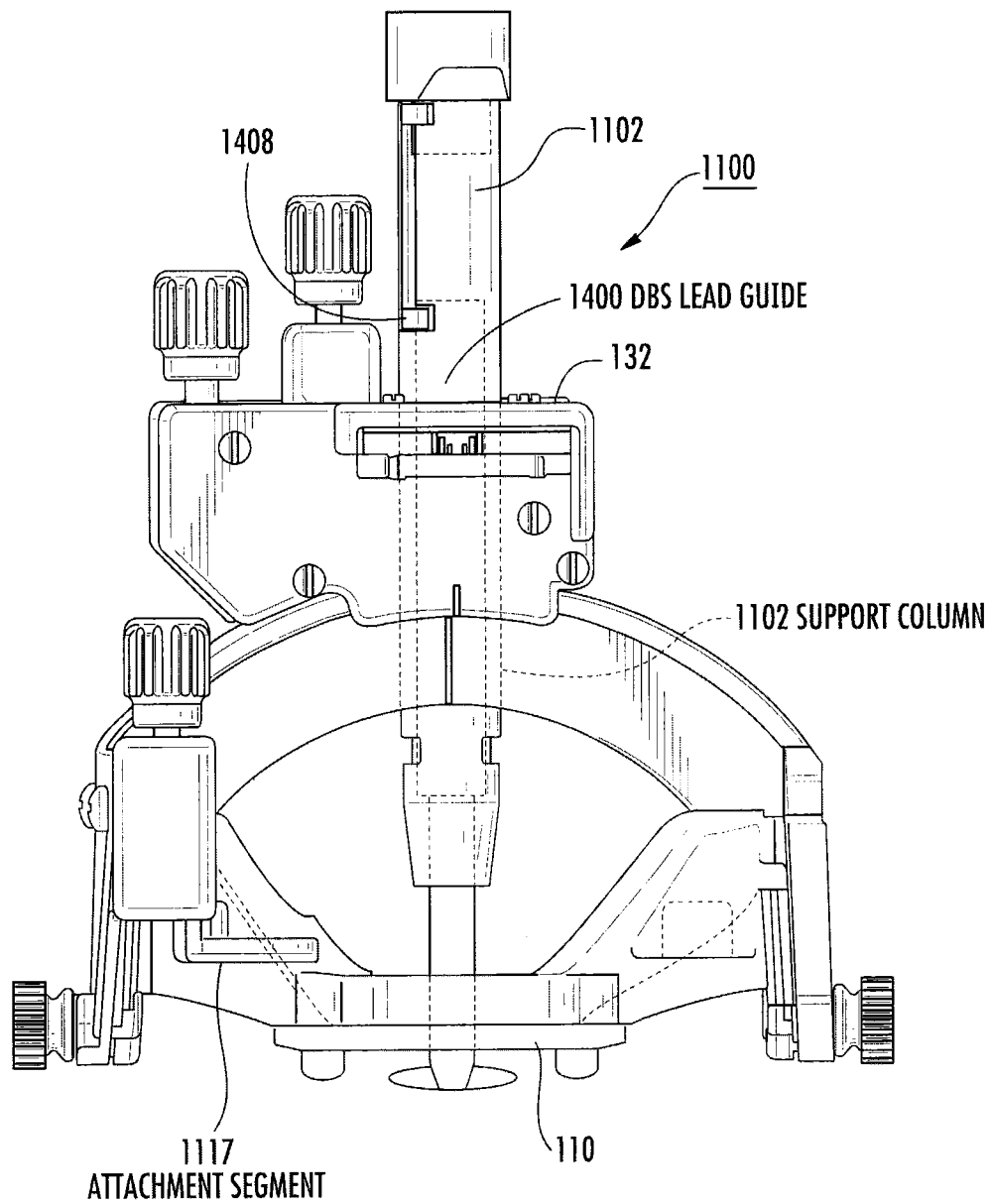
FIG. 32 is a side view of a trajectory frame illustrating the tracking guide shown in FIGS. 31A-31D, replaced by a device (DBS lead) guide according to embodiments of the present invention.

FIG. 32 is a side view of a trajectory frame 1100 illustrating the universal tracker 1190 shown in FIGS. 31A-D, replaced by a device (DBS lead) guide 1400 with lugs 1408 that engage guide (e.g., support column) 1102 according to embodiments of the present invention.

FIG. 33 is a schematic illustration of a camera-based image guided system S with a software imaging/tracking module and camera tracking system C that can be used with the trajectory frame 1100 and various components discussed herein according to embodiments of the present invention.

Figure 34B:
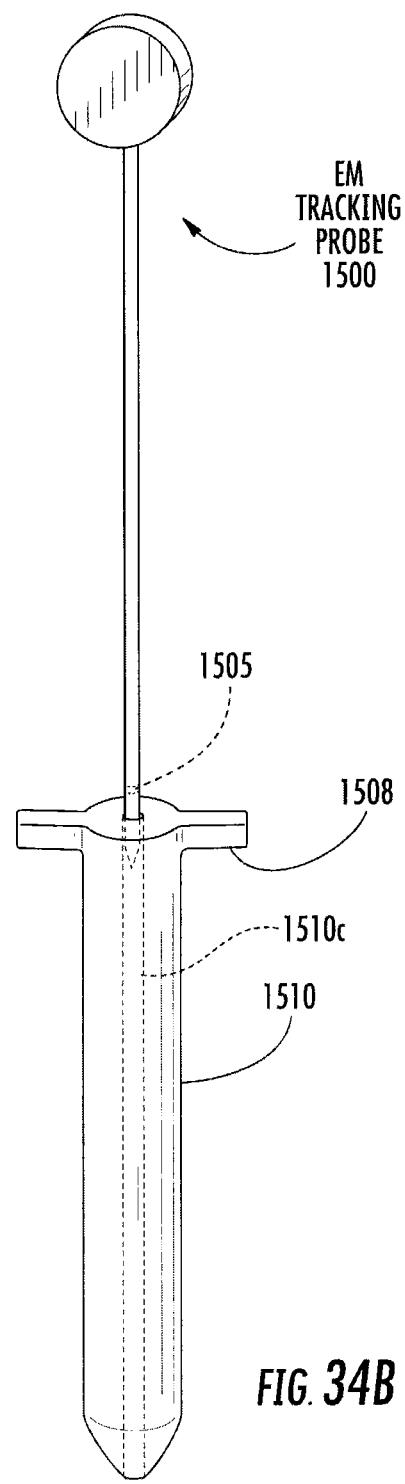
FIG. 34B is a schematic illustration of a tracking probe with a cooperating mount to attach to the trajectory frame shown in FIG. 34A according to embodiments of the present invention.

FIG. 34A illustrates a trajectory frame 100 cooperating with a EM tracking probe 1500 for EM-based tracking systems 10EM. The tracking probe 1500 can releasably attach to the guide 1102 (e.g., support column) of the trajectory frame 100. As shown in FIGS. 34A and 34B, the EM tracking probe 1500 can comprise a mount 1510 with outwardly extending lugs 1508 that engage the slots 1103 of the guide 1102. The EM-based tracking system 10EM can be any suitable system, such as, but not limited to, the Stealth-Station® AxiEM™ surgical navigation system with electromagnetic (EM) tracking technology by Medtronic, Inc. The EM tracking can use a single-coil or multiple coil design. The at least one coil 1505 can include a coil 1505 that resides at a distal end portion or tip of the probe 1500 or at a location above the distal end. The mount 1510 can include a closed channel or an open channel 1510c that is sized to slidably snugly hold a (typically rigid or semi-rigid) stem of the tracking probe 1500.

Generally stated, the EM tracking system 10EM can generate an electromagnetic field around the patient's target anatomy and/or the trajectory frame 100 using a tracking probe 1500 with the at least one EM coil 1505 that can be used to triangulate the position of instruments, e.g., the guide 1102 of the trajectory frame 100 and/or patient-tracking devices during surgical navigation procedures. See, e.g., U.S. Pat. No. 8,543,189, the content of which is hereby incorporated by reference as if recited in full herein. EM tracking can be configured so that it does not rely on line-of-sight between the emitter E (FIG. 35) and the surgical instruments, such as the tracking probe 1500. The emitter E can be draped and kept outside of the sterile field and the staff can move in and out of the EM field with minimal or no disruption to the surgical navigation information. Algorithms of the EM system 10EM can monitor the electromagnetic field, including metal disturbance, to ensure surgical navigation precision. FIG. 35 also illustrates that the EM surgical navigation system 10EM can employ external EM markers 90 on patient anatomy.

The guide 1102 of the trajectory frame 100 can be configured to serially, interchangeably receive the optical and EM tracking/navigation probes 1162, 1190, 1500 to allow for use in different navigation systems.

It is contemplated that a pre-op image of a patient's brain can be imported into the EM or camera based system "S" and displayed on the display with tracking information from the tracking probe 1162, the universal tracker 1190 and/or the reference frame 1200 or the EM system 10EM. Patient images can be obtained the day of surgery with the trajectory frame 100 mounted to facilitate registration (aligning orbs or anatomical features between the image sets). The trajectory frame 100 can be tracked using the EM and/or camera navigation system.

In some embodiments, for "asleep" procedures, the reference frame 1200 can be attached to a head fixation frame (not shown). For "awake" procedures, the reference frame 1200 can be attached to the trajectory frame as discussed above. CT images can be obtained at various points during the procedure, such as at final lead implantation, for example, without requiring constant imaging during a procedure.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A trajectory assembly for use with a surgical system, comprising:
   a base having a patient access aperture formed therein, wherein the base is configured to be secured to a body of a patient, the base comprising a circular perimeter with a plurality of ears spaced apart about the circular perimeter, the ears extending laterally outward from the base;
   a yoke movably mounted to the base and rotatable about a roll axis;
   a platform movably mounted to the yoke and rotatable about a pitch axis;
   a support column secured to the platform, wherein the support column comprises opposing axially spaced apart proximal and distal ends with a bore therethrough, wherein the proximal end resides a distance above the platform;
   a tracking probe removably secured to the support column and comprising a plurality of reflective members arranged in a spaced apart geometric relationship; and
   a bracket attached to at least one of the ears of the base and supporting an arm that extends laterally outwardly therefrom a distance between about 0.25 and about 3 inches with laterally spaced apart first and second ends, the second end of the arm comprising a first starburst connector that is attached to a reference frame with an array of reflective members thereon for tracking by a camera based tracking system.

2. The trajectory assembly of claim 1, wherein the tracking probe comprises a cylindrical body with a first diameter extending through the bore of the support column that merges into a lower segment with a second smaller diameter, and wherein a proximal end of the cylindrical body is attached to a planar member that holds the reflective members of the tracking probe in the spaced apart geometric relationship with a plurality of the reflective members at a location that is above the support column.

3. The trajectory assembly of claim 1, wherein the reflective members of the tracking probe are also detectable by the camera-based tracking system, and wherein the tracking probe has a tubular body with a proximal diameter that is larger than a diameter at a distal end thereof.

4. The trajectory assembly of claim 1, wherein the support column is configured to releasably, serially and interchangeably, secure a microelectrode probe driver adapter with a plurality of spaced apart downwardly extending microelectrode ports, wherein the microelectrode probe drive adapter has an elongate cylindrical body with opposing upper and lower ends, and wherein, in position in the support column, the upper end of the cylindrical body holds the ports above the support column and has a larger outer diameter that the lower end.

5. The trajectory assembly of claim 1, wherein the support column has a top with an open circular perimeter and a downwardly extending slot that directly contacts the tracking probe and/or a microelectrode probe driver adapter.

6. The trajectory assembly of claim 4, wherein the microelectrode probe driver adapter is releasably secured to the support column and holds a microelectrode probe driver at the upper end of the cylindrical body above the platform.

7. The trajectory assembly of claim 1, further comprising a plurality of actuators operably connected to the yoke and/or platform that are configured to translate and rotate the support column relative to the body of the patient, the ears having upper and lower planar surfaces, the first upright segment attached to one of the upper or lower planar surfaces of one ear.

8. The trajectory assembly of claim 1, wherein the base is configured to be secured to the scalp and/or skull of the body of a respective patient about a burr hole formed therein, wherein the support column is configured to interchangeably releasably secure a device guide in place of the tracking probe for intra-brain placement of at least one device in vivo, wherein the circular perimeter of the base surrounds an open center space.

9. The trajectory assembly of claim 1, wherein the platform comprises an X-Y support table movably mounted to the platform that is configured to move in an X-direction and Y-direction relative to the platform, wherein the support column is secured to the X-Y support table, and wherein the tracking probe has a length greater than a length of the support column and further comprises a planar upper member that holds the reflective members above the X-Y support table with one or more of the reflective members above one or more of the others.

10. The trajectory assembly of claim 1, wherein the bracket comprises a first upright segment attached to at least one of the ears that supports the arm, wherein the first upright segment of the bracket has an axially extending centerline that is parallel to an axially extending centerline of the circular perimeter of the base, and wherein the first starburst connector has an axially extending centerline that is orthogonal to the axially extending centerline of the first upright segment.

11. The trajectory assembly of claim 1, wherein the bracket includes a second upright segment residing under and attached to a different ear and a bridging arm extending between the first and second upright brackets.

12. The trajectory assembly of claim 1, wherein the first starburst connector has a first swivel axis that allows positional adjustment of an end portion of the arm, wherein the first end of the arm has a first upright segment that has a starburst member attached to a planar primary surface of one ear, the starburst member having a perimeter that is attached to a perimeter of an aligned second starburst connector at the first end of the arm, wherein the second starburst connector is attached to the first starburst member using a fixation member that extends through the ear and axially extending centerlines of the first starburst member, and wherein the second starburst connector that has a second swivel axis that is orthogonal to the first swivel axis.

13. The trajectory assembly of claim 1, wherein the tracking probe further comprises image fiducials electronically detectable as regions with increased signal to noise ratios in MRI and/or CT images thereof.

14. A surgical assembly, comprising:
(i) a trajectory frame, comprising:
a base having a patient access aperture formed therein, wherein the base is configured to be secured to a body of a patient, wherein the base has a circular perimeter defining a patient access space and comprises a plurality of spaced apart ears extending outwardly from the circular perimeter of the base and arcuate arms rising above the base;
a yoke movably mounted to the base and rotatable about a roll axis;
a platform movably mounted to the yoke and rotatable about a pitch axis; and
a support column secured to the platform, wherein the support column comprises opposite proximal and distal ends, wherein the support column distal end is positioned above the patient access aperture, wherein the support column comprises a bore therethrough that extends from the proximal end to the distal end; and
a bracket with a bracket arm comprising a first end attached to at least one of the ears of the base, the bracket arm extending laterally outward from the base a distance between about 0.25 inches and about 3 inches, below one of the arcuate arms, wherein the bracket arm holds a reference frame with a plurality of spaced apart reflective members, and wherein the reference frame and reference frame reflective members are held above the circular perimeter of the base and below the platform; and
(ii) a tracking probe and a microelectrode probe driver adapter that are removably, serially, secured to the support column to extend through the bore of the support column,
wherein the tracking probe comprises an elongate body with opposing proximal and distal ends, a plurality of reflective members arranged in a geometric relationship that reside above the base,
wherein the microelectrode probe driver adapter with a plurality of downwardly extending microelectrode ports, wherein the microelectrode probe driver adapter has an elongate body with an upper end and a lower end, and wherein the upper end has a diameter that is greater than the lower end.

15. The assembly of claim 14, wherein the base is configured to be secured to a scalp and/or skull of the patient about a burr hole formed therein, wherein the bore of the support column is configured to guide intra-brain placement of at least one device in vivo, wherein at least one of the ears comprises an upper and/or lower planar primary surface, and wherein the first end of the bracket arm is attached to the planar primary surface of at least one of the ears.

16. The assembly of claim 14, wherein the platform comprises an X-Y support table movably mounted to the platform that is configured to move in an X-direction and Y-direction relative to the platform, and wherein the support column is secured to the X-Y support table.

17. The assembly of claim 14, wherein the bracket arm comprises a first upright segment as the first end that resides beneath one of the arcuate arms and that is attached to one ear with a starburst connector on an opposing laterally spaced apart end portion of the bracket arm configured to engage the reference frame with the array of reflective members thereon for tracking by a camera based tracking system.

18. The assembly of claim 17, wherein the bracket includes a second upright segment residing under and attached to a different ear and a bridging arm extending between the first and second upright brackets.

19. The assembly of claim 17, wherein the starburst connector has a first swivel axis, and wherein the first upright segment has a second starburst connector that has a second swivel axis that is orthogonal to the first swivel axis.

20. A surgical method, comprising:
providing a camera system;
affixing a trajectory frame with a cooperating support column with an open through bore to a skull of a patient so that an open center of a circular perimeter of a base of the trajectory frame defines a patient access space and the support column is above the base, wherein the base comprises a plurality of ears extending outward from the perimeter of the base; wherein the trajectory frame is configured to translate and rotate such that a device held by the support column can be positioned to a desired intrabody access path trajectory;

attaching a bracket to one or more of the ears of the base to extend outward from the perimeter of the base a distance between about 0.25 inches and 3 inches, the bracket comprising an array of reflective members;

removably securing a tracking probe with an array of reflective members to the support column such that the tracking probe extends down through the bore to place a lower end of the tracking probe above the skull of the patient;

identifying a trajectory using the camera system and positions of the array of reflective members of the tracking probe;

removing the tracking probe from the support column of the trajectory frame; then inserting a microelectrode probe driver adapter with a plurality of microelectrode ports and a downwardly extending cylindrical body into the support column of the trajectory frame;

attaching a microelectrode probe driver to the microelectrode probe driver adapter; then driving microelectrodes into the patient's brain through the microelectrode ports using the probe driver attached to the probe driver adapter held by the support column; and tracking movement of a head of the patient using the camera system and the array of reflective members held by the bracket attached to the one or more ears of the base.

21. A trajectory frame assembly for use with a surgical system, comprising:

a base having a patient access aperture formed therein, wherein the base is configured to be secured to a body of a patient, wherein the base comprises a circular perimeter with a plurality of ears spaced apart about the circular perimeter, the ears extending laterally outward from the base;

a yoke movably mounted to the base and rotatable about a roll axis;

a platform movably mounted to the yoke and rotatable about a pitch axis;

an elongate support column secured to the platform, wherein the support column comprises opposite proximal and distal ends, wherein the support column comprises a bore therethrough that extends from the proximal end to the distal end, wherein the support column is configured to serially receive and removably secure at least one elongate device guide and an elongate tracking probe so that the tracking probe and device guide extend through the bore, wherein the device guide has a cylindrical body, and wherein the tracking probe holds at least one electromagnetic tracking coil above the support column for an electromagnetic surgical navigation; and a bracket attached to at least one of the ears of the base and supporting an arm that extends laterally outwardly therefrom a distance between about 0.25 and about 3 inches with laterally spaced apart first and second ends, the second end of the arm comprising a starburst connector.

22. The assembly of claim 21, wherein the platform comprises an X-Y support table moveably mounted to the platform that is configured to move in an X-direction and Y-direction relative to the platform, and wherein the column support is secured to the X-Y support table, and wherein the base of the trajectory frame is configured to be secured to the scalp or skull of a patient about a burr hole formed therein.

* * * * *

UNITED STATES PATENT AND TRADEMARK OFFICE
CERTIFICATE OF CORRECTION

PATENT NO. : 10,307,220 B2
APPLICATION NO. : 15/250590
DATED : June 4, 2019
INVENTOR(S) : Piferi et al.

Page 1 of 1

It is certified that error appears in the above-identified patent and that said Letters Patent is hereby corrected as shown below:

In the Claims

Column 28, Line 5, Claim 14:
Please correct "comprising, a first" to read -- comprising a first --

Signed and Sealed this
Seventeenth Day of September, 2019

Andrei Iancu
*Director of the United States Patent and Trademark Office*